United States Patent
Chang

(12) 
(10) Patent No.: US 6,248,721 B1
(45) Date of Patent: Jun. 19, 2001

(54) METHOD OF USING MOUSE MODEL FOR EVALUATION OF HIV VACCINES

(76) Inventor: Lung-Ji Chang, 3102 NW. 57th Ter., Gainesville, FL (US) 32606

( * ) Notice: Subject to any disclaimer, the term of this patent is extended or adjusted under 35 U.S.C. 154(b) by 0 days.

(21) Appl. No.: 08/848,760

(22) Filed: May 1, 1997

Related U.S. Application Data

(63) Continuation-in-part of application No. 08/838,702, filed on Apr. 9, 1997.

(51) Int. Cl.$^7$ .................. A61K 31/713; A61K 48/00; C12N 15/867; A01K 67/027

(52) U.S. Cl. ................... 514/44; 424/932; 800/8; 800/11; 435/320.1; 435/235.1; 435/375

(58) Field of Search ............ 424/4, 93.2; 435/235.1, 435/172.1, 320.1, 375; 800/8, 11; 514/44; 536/23.5

(56) References Cited

U.S. PATENT DOCUMENTS 5,851,813 * 12/1998 Desrosiers .................. 435/235.1

OTHER PUBLICATIONS

Shibata et al. Comparative studies on tat mutants of three primate lentiviruses. Archives of Virology, vol. 114, pp. 243–250, 1990.*

Agatsuma et al. Protection of hu–PBL–SCID/beige mice from HIV–1 infection by a modified oligonucleotide, RKS–1443. Antiviral Research, vol. 30, No. 1, A35. Presented Orally May 19–24, 1996.*

McBride et al. Human Immunodeficiency virus infection of xenografted SCID–beige mice. Journal of Medical Virology, vol. 47, No. 2, pp. 130–138, Oct. 1995.*

Levy, J. A. Pathogenesis of Human Immunodeficiency Virus Infection. Microbiology and Molecular Reviews, vol. 57, No. 1, pp. 183–289, Mar. 1993.*

* cited by examiner

Primary Examiner—Deborah J. Clark
(74) Attorney, Agent, or Firm—Saliwanchik, Lloyd & Saliwanchik

(57) ABSTRACT

The present invention provides animals and methods for the evaluation of vaccines. In particular, the present invention provides humanized animal models for the evaluation of vaccines designed to confer immunity against human pathogens, including vaccines directed against the human immunodeficiency virus. The present invention further relates to HIV vaccines. In particular, the present invention provides attenuated replication-competent HIV vaccines and replication-defective HIV vaccines. In addition, the invention provides modified Leishmania cells expressing HIV proteins.

5 Claims, 19 Drawing Sheets

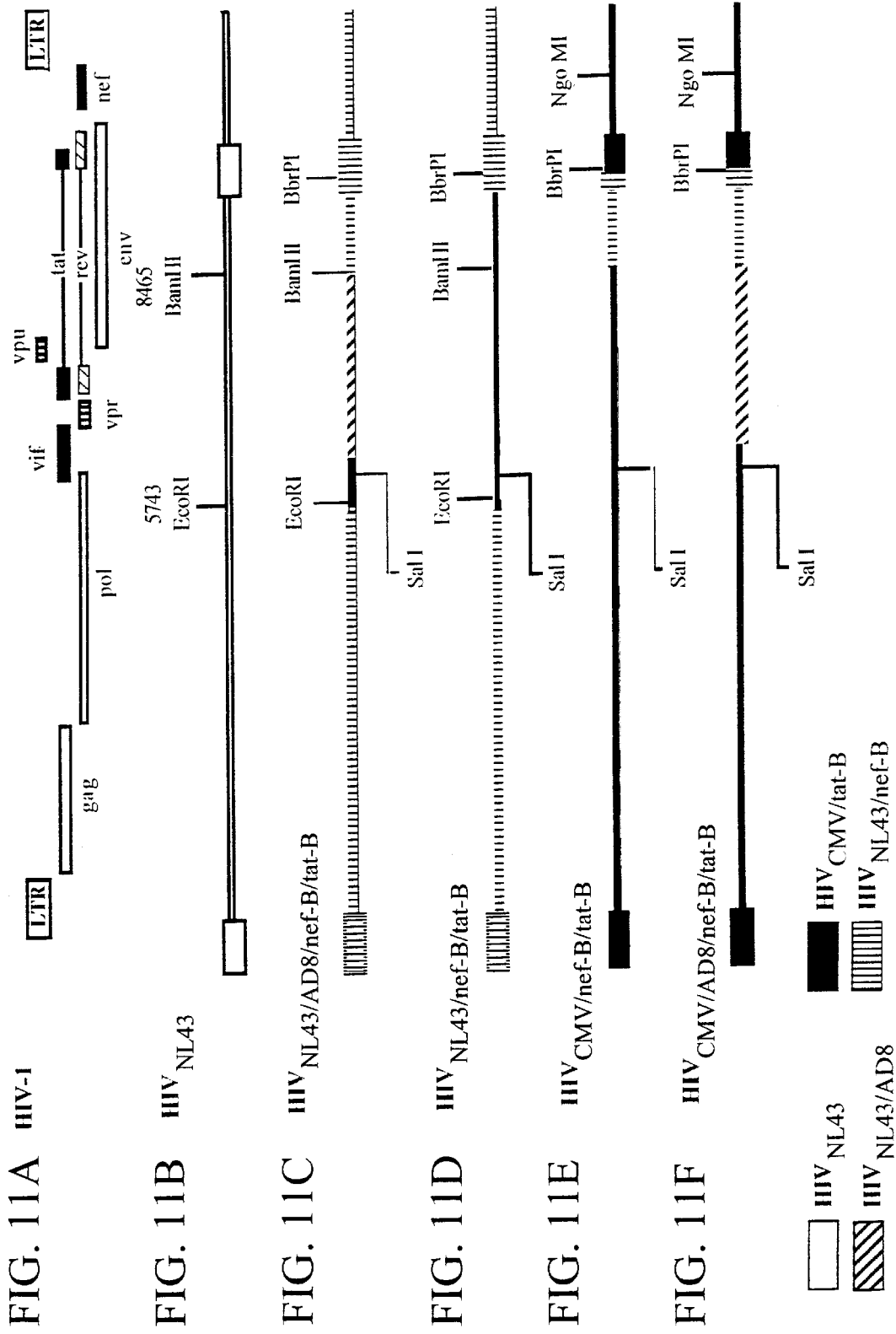

FIG. 12A
FIG. 12B

METHOD OF USING MOUSE MODEL FOR EVALUATION OF HIV VACCINES

This is a Continuation-In-Part of application Ser. No. 08/838,702, filed Apr. 9, 1997 the disclosure of which is herein incorporated by reference.

FIELD OF THE INVENTION

The present invention relates to the evaluation of vaccines. In particular, the present invention provides humanized animal models for the evaluation of vaccines designed to confer immunity against human pathogens, including vaccines directed against the human immunodeficiency virus. The present invention further relates to HIV vaccines. In particular, the present invention provides attenuated replication-competent HIV vaccines and replication-defective HIV vaccines.

BACKGROUND OF THE INVENTION

The development of effective vaccines for the prevention of human immunodeficiency virus (HIV) infection has been hampered by the lack of suitable in vivo HIV-1 infection animal models. Given the complex interaction of HIV with the immune system, there is no substitute for in vivo models for HIV infection and HIV vaccine evaluation. Existing animal models employed for HIV infection and vaccine development include chimpanzees infected with HIV-1, macaques infected with either SIV or HIV-2, cats infected with feline immunodeficiency virus and scid/scid mice reconstituted with human cells and infected with HIV. None of these models are ideal for the evaluation of HIV vaccines. The replication of HIV in chimpanzees is more restricted than in humans; therefore, vaccines shown to be protective in chimpanzees may fail to protect humans as chimpanzees may be more easy to protect from HIV infection. In addition, the number of chimpanzees available for research is small and therefore, it is difficult to obtain statistically significant experimental results, these animals are costly to maintain and once exposed to HIV these animals must be confined for the rest of their lives at a cost of greater than $100,000.00/ chimp [Stott and Almond (1995) Nat. Med. 1:295]. While the supply of macaques is greater than that of chimpanzees, these animals are also costly to maintain. Most importantly, macaques cannot be infected with HIV-1 and thus, infection with HIV-2 or SIV must be used as a surrogate model for HIV-1 infection. Scid/scid mice reconstituted with human lymphocytes (hu-PBL-SCID mice), while permitting infection of the human cells with HIV-1, have failed to provide a model in which HIV vaccines and HIV immunity can be evaluated. This failure is due to the fact that most of the human T lymphocytes in the reconstituted scid/scid mice exhibit activated cell phenotypes soon after reconstitution, and almost all (>99%) human T cells exhibit mature memory phenotypes in a state of reversible anergy [Rizza et al. (1996) J. Virol. 70:7958; Tarry-Lehmann and Saxon (1992) J. Exp. Med. 175:503; Tarry-Lehmann et al. (1995) Immunol. Today 16:529]. Therefore, the lack of sufficient numbers of immature naive T cells after reconstitution renders the hu-PBL-SCID model unsuitable for the evaluation of anti-HIV immunity following administration of a HIV vaccine.

The ultimate system for the study of HIV vaccines is, of course, the human. However, given the fact that HIV infection is almost invariably fatal in humans, ethical considerations limit the use of human volunteers in HIV vaccine evaluation. The art needs animal models in which anti-HIV immunity can be assessed to permit the evaluation of HIV vaccines.

SUMMARY

The present invention provides novel humanized animal models that permit the identification of immune-modulating genes and combinations thereof useful for the treatment of human tumors. In addition, the present invention provides methods of treating subjects having a tumor with one or more immune-modulating genes and provides tumor cell vaccines comprising tumor cells modified to express immune-modulating genes. The novel animals of the present invention provide a means of evaluating vaccines, including cancer vaccines and vaccines directed against human pathogens (e.g., HIV, malaria, Leishmania, etc.). In addition, the invention provides HIV vaccines including live attenuated HIV vaccines and HIV DNA vaccines.

Accordingly, the present invention provides an immunodeficient mouse comprising human T lymphocytes expressing the CD45 antigen wherein at least 5% of the human T lymphocytes expressing the CD45 antigen represent immature naive T lymphocytes. The invention is not limited by the nature of the immunodeficient mouse strain employed. In a preferred embodiment, the immunodeficient mouse is a SCID/beige mouse.

In another preferred embodiment, the immunodeficient mouse comprising human T lymphocytes further comprising human tumor cells. The invention is not limited by the nature of the human tumor cells employed. The human tumor cells may be established tumor cells, primary tumors cells or tumor cells (established or primary) modified to express one or more immune-modulating genes, genes encoding cell cycle regulators and genes encoding inducers of apoptosis.

In another embodiment, the present invention provides a SCID/beige mouse comprising human immune cells. The invention is not limited by the nature of the human immune cells, these cells may be human PBLs, splenocytes, cells isolated from lymph nodes and/or peritoneal lavage. In a preferred embodiment, the SCID/beige mouse comprising human immune cells further comprising human tumor cells. The invention is not limited by the nature of the human tumor cells employed. The human tumor cells may be established tumor cells, primary tumors cells or tumor cells (established or primary) modified to express one or more immune-modulating genes, genes encoding cell cycle regulators and genes encoding inducers of apoptosis. In a preferred embodiment, the tumor cells are derived from central nervous system cells, most preferably glioblastoma cells. In another preferred embodiment, the tumor cells are malignant melanoma cells.

The present invention further provides a method comprising: a) providing: i) a SCID/beige mouse; ii) human tumor cells; iii) human peripheral blood lymphocytes; b) introducing a first dose of the tumor cells into said mouse; c) reconstituting the mouse containing said tumor cells with the lymphocytes; and d) monitoring the reconstituted mouse for the growth of the tumor cells. The invention is not limited by the nature of the human tumor cells employed. The human tumor cells may be established tumor cells, primary tumors cells or tumor cells (established or primary) modified to express one or more immune-modulating genes, genes encoding cell cycle regulators and genes encoding inducers of apoptosis. In a preferred embodiment, the tumor cells are derived from central nervous system cells, most preferably glioblastoma cells. In another preferred embodiment, the tumor cells are malignant melanoma cells.

In a preferred embodiment, the method further comprises identifying at least one immune modulating gene (or gene encoding a cell cycle regulator or inducer of apoptosis)

whose expression prevents the growth of the introduced tumor cells in the reconstituted mouse. In another preferred embodiment, the method comprises, following the reconstitution, the additional step of vaccinating the reconstituted mouse with a second dose of tumor cells. In a preferred embodiment, the first dose of tumor cells comprises unmodified tumor cells and the second dose of tumor cells comprises irradiated tumor cells. In a particularly preferred embodiment, the irradiated tumor cells express at least one immune-modulating gene (or gene encoding a cell cycle regulator or inducer of apoptosis).

In one embodiment of the methods of the present invention, the tumor cells and the lymphocytes come from the same donor. In another embodiment, the tumor cells and the lymphocytes come from different donors.

The present invention further provides a method comprising: a) providing: i) a SCID/beige mouse; ii) irradiated and unirradiated human tumor cells; iii) human peripheral blood lymphocytes; b) reconstituting said mouse with the lymphocytes; c) vaccinating the mouse with the irradiated tumor cells; d) introducing the unirradiated tumor cells into the vaccinated mouse; and e) monitoring the vaccinated mouse for the growth of the unirradiated tumor cells. The invention is not limited by the nature of the irradiated tumor cells. The irradiated tumor cells may be established tumor cells, primary tumors cells or tumor cells (established or primary) modified to express one or more immune-modulating genes, genes encoding cell cycle regulators and genes encoding inducers of apoptosis. In a preferred embodiment, the irradiated and modified tumor cells are derived from central nervous system cells, most preferably glioblastoma cells. In another preferred embodiment, the irradiated and modified tumor cells are malignant melanoma cells.

In a preferred embodiment, the method further comprises identifying at least one immune modulating gene (or gene encoding a cell cycle regulator or inducer of apoptosis) whose expression prevents the growth of said unirradiated tumor cells in said vaccinated mouse.

The present invention also provides a tumor cell vaccine comprising a tumor cell expressing B7-2 and at least one additional immune modulator or a cell cycle regulator or inducer of apoptosis. The vaccines of the present invention are not limited by the nature of the immune modulator or a cell cycle regulator or inducer of apoptosis employed. In a preferred embodiment, the additional immune modulator is a cytokine. The invention is not limited by the nature of the cytokine employed. In a preferred embodiment, the cytokine is selected from the group consisting of interleukin 2, interleukin 4, interleukin 6, interleukin 7, interleukin 12, granulocyte-macrophage colony stimulating factor, granulocyte colony stimulating factor, interferon-gamma, tumor necrosis factor-alpha.

The present invention provides a method of treating a tumor comprising: a) providing: i) a subject having a tumor of the central nervous system; ii) an expression vector encoding the human B7-2 protein and at least one additional immune modulator or a cell cycle regulator or inducer of apoptosis; b) transferring the expression vector into the tumor under conditions such that the B7-2 protein and the immune-modulator (and/or a cell cycle regulator or inducer of apoptosis) are expressed by at least a portion of the tumor. In a preferred embodiment, the method further comprises, prior to transfer of the expression vector, the step of removing at least a portion of the tumor from the subject and following the transfer of said expression vector, irradiating the tumor cells expressing the B7-2 protein and the immune-modulator (and/or a cell cycle regulator or inducer of apoptosis) and introducing the irradiated tumor cells back into the subject to create an immunized subject. In another embodiment, the method further comprises introducing at least one additional dose of irradiated tumor cells expressing the B7-2 protein and the immune-modulator (and/or a cell cycle regulator or inducer of apoptosis) into the immunized subject.

The invention further provides a method comprising: a) providing: i) a SCID/beige mouse comprising human immune cells; ii) an injectable preparation comprising at least one component derived from a human pathogen; iii) a composition comprising an infectious human pathogen; b) injecting the mouse with the injectable preparation to produce an injected mouse; c) exposing the injected mouse to the composition; and d) monitoring the exposed mouse for the presence of infection of the human immune cells by the infectious human pathogen. In a preferred embodiment, the injecting of step b) is repeated at least once prior to exposing the mouse to the composition. The injectable preparation comprises a candidate vaccine; a candidate vaccine may comprise proteins or peptides or nucleic acids and may be immunogenic. However, as this method offers a means to evaluate candidate vaccines, some candidate vaccines are expected to be immunogenic (i.e., capable of invoking an immune response directed against the pathogen from which the protein, peptide or nucleic acid was derived) and some are expected to not be immunogenic (and would therefore be rejected as a vaccine for use in subject such as a human). In a preferred embodiment, the injectable preparation is immunogenic. The injectable preparation may comprise pharmacological carriers and excipients such as aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions. Further, the injectable preparation may comprise as adjuvant (e.g., alum, complete or incomplete Freund's, SAF-1).

The invention is not limited by the nature of the human pathogen. In a preferred embodiment, the human pathogen is selected from the group comprising human immunodeficiency virus, Leishmania, Mycobacterium (e.g., *M. tuberculosis*), and Plasmodium (the causative agent of malaria).

The invention is not limited by the nature of the component of the human pathogen present in the injectable composition. In a preferred embodiment, the component of the human pathogen comprises at least a portion of a protein derived from the pathogen; the component may be a complete protein molecule or a peptide derived from the complete protein (and may be produced by peptide synthesis, recombinant DNA methodologies or protease digestion of the intact protein). In another preferred embodiment, the component of the human pathogen comprises DNA. In a particularly preferred embodiment, the DNA comprises proviral DNA encoding a human immunodeficiency virus genome capable of expressing viral structural genes but incapable of being packaged into viral particles. In a preferred embodiment, the DNA comprises plasmid DNA selected from the group consisting of pHP-1, pHP-2 and pHP-3.

In another embodiment, the injectable preparation comprises an attenuated replication-competent human immunodeficiency virus (i.e., capable of producing only a limited infection and preferably incapable of producing the pathological changes associated with infection by a non-attenuated HIV). The invention is not limited by the nature of the change which renders the virus attenuated. In a preferred embodiment, the attenuated virus comprises a mutated tat gene; preferably, the genome of the attenuated virus cannot express a functional Tat protein. In another preferred embodiment, the genome of attenuated virus genome further comprises a mutated nef gene; preferably, the genome of the attenuated virus cannot express either a functional Tat protein or Nef protein. In a preferred embodiment, the attenuate virus is selected from the group consisting of $HIV_{CMV/tat-B}$, $HIV_{CMV/AD8/nef-B/tat-B}$, $HIV_{NL43/AD8/tat-B/nef-B}$ and $HIV_{NL43/nef-B/tat-B}$.

In another embodiment, the injectable preparation comprises attenuated Leishmania cells. The invention is not limited by the nature of the change which renders the Leishmania cell attenuated. In a preferred embodiment, the attenuated Leishmania cell comprises heterologous DNA encoding a cysteine protease gene. The cysteine protease gene may be a leishmanial cysteine protease gene or a cysteine protease gene from another organism. When a leishmanial cysteine protease gene is employed it is preferably placed in operable combination with promoters and optionally enhancers functional in a Leishmania cell. As the leishmanial cysteine protease gene is not present in its native configuration (i.e., chromosomal configuration), it comprises heterologous DNA. Most preferably, the leishmanial cysteine protease gene is present on an expression vector such as pALT-Neo or pX. As shown herein, the overexpression of cysteine protease in Leishmania cells attenuates the Leishmania cell and provides an effective vaccine for the prevention of leishmaniasis. In another preferred embodiment, the heterologous DNA further comprises DNA encoding a human immunodeficiency virus gene selected from the group consisting of the env gene, the gag gene, the pol gene, the tat gene, the rev gene, the vif gene, the vpu gene, the vpr gene and the nef gene. Leishmania cells infect macrophages and therefore, Leishmania cells expressing HIV proteins provide a means to present HIV antigens to a host in the context of an APC (i.e., provides an HIV vaccine).

The invention is not limited by the nature of the monitoring employed to detect the presence (or absence) of infection of the human immune cells in the SCID/bg mouse comprising human immune cells (e.g., a hu-PBL-SCID/bg mouse). Serum collected from the mouse following vaccination and challenge with the pathogen may be examined for the presence of human immunoglobulin directed against the pathogen (evidence of humoral immunity). Cell mediated immunity directed against the pathogen may be examined by a variety of means known to the art, including but not limited to in vitro ELISPOT analysis of γ-IFN production by lymphocytes (e.g., splenocytes) isolated from the vaccinated and challenged mice (using pathogen-infected PBLs as stimulators). Further, the mouse may be examined for the presence of infection in the sites expected to be infected by the pathogen employed for the challenge (e.g., immunostaining of lymphocytes collected from mice challenged with HIV to detect the presence of HIV proteins in and/or on lymphocytes and/or macrophages).

The present invention also provides a method comprising: a) providing: i) a SCID/beige mouse comprising human immune cells; ii) an injectable preparation comprising one or more components derived from a human immunodeficiency virus (HIV); iii) a composition comprising non-attenuated human immunodeficiency virus; b) injecting the mouse with the injectable preparation to produce an injected mouse; c) exposing the injected mouse to the composition; and d) monitoring the exposed mouse for the presence of infection of the human immune cells by the non-attenuated human immunodeficiency virus. The invention is not limited by the non-attenuated virus employed; any virus capable of causing an non-attenuated infection may be employed. Preferably, the non-attenuated virus is a virus isolated from a patient with AIDS (i.e., a clinical isolate) or is a virulent laboratory strain. Particularly preferred non-attenuated HIV strains include the NL4-3 strain, the ADA strain and HIV-1 primary isolates covering the different HIV clades (e.g., 92RW008, 92BR003, 92HT593, etc. available from the NIH AIDS Research and Reference Reagent Program of National Institutes of Health, Bethesda, Md.).

In a preferred embodiment, the injecting of step b) is repeated at least once prior to exposing the mouse to the composition. The injectable preparation comprises a candidate vaccine; a candidate vaccine may comprise proteins or peptides or nucleic acids and may be immunogenic. However, as this method offers a means to evaluate candidate vaccines, some candidate vaccines are expected to be immunogenic (i.e., capable of invoking an immune response directed against the pathogen from which the protein, peptide or nucleic acid was derived) and some are expected to not be immunogenic (and would therefore be rejected as a vaccine for use in subject such as a human). In a preferred embodiment, the injectable preparation is immunogenic. The injectable preparation may comprise pharmacological carriers, excipients and adjuvants as discussed above.

The invention is not limited by the nature of the component of the HIV present in the injectable composition. In a preferred embodiment, the component of the HIV comprises at least a portion of a protein derived from a HIV; the component may be a complete protein molecule or a peptide derived from the complete protein (and may be produced by peptide synthesis, recombinant DNA methodologies or protease digestion of the intact protein). In another preferred embodiment, the component of the HIV comprises DNA derived from HIV. In a particularly preferred embodiment, the DNA comprises proviral DNA encoding a HIV genome capable of expressing viral structural genes but incapable of being packaged into viral particles. In a preferred embodiment, the DNA comprises plasmid DNA selected from the group consisting of pHP-1, pHP-2 and pHP-3.

In another embodiment, the injectable preparation comprises an attenuated replication-competent HIV (i.e., capable of producing only a limited infection and preferably incapable of producing the pathological changes associated with infection by a non-attenuated HIV). The invention is not limited by the nature of the change which renders the virus attenuated. In a preferred embodiment, the attenuated virus comprises a mutated tat gene; preferably, the genome of the attenuated virus cannot express a functional Tat protein. In another preferred embodiment, the genome of attenuated virus genome further comprises a mutated nef gene; preferably, the genome of the attenuated virus cannot express either a functional Tat protein or Nef protein. In a preferred embodiment, the attenuate virus is selected from the group consisting of $HIV_{CMV/tat-B}$, $HIV_{CMV/AD8/nef-B/tat-B}$, $HIV_{NL43/AD8/tat-B/nef-B}$ and $HIV_{NL43/nef-B/tat-B}$.

In another embodiment, the injectable preparation comprises attenuated Leishmania cells. The invention is not limited by the nature of the change which renders the Leishmania cell attenuated. In a preferred embodiment, the attenuated Leishmania cell comprises heterologous DNA encoding a cysteine protease gene as described above. In another preferred embodiment, the heterologous DNA further comprises DNA encoding a HIV gene selected from the group consisting of the env gene, the gag gene, the pol gene, the tat gene, the rev gene, the vif gene, the vpu gene, the vpr gene and the nef gene.

The invention is not limited by the nature of the monitoring employed to detect the presence (or absence) of infection of the human immune cells in the SCID/bg mouse comprising human immune cells (e.g., a hu-PBL-SCID/bg mouse) as described above.

The invention also provides an attenuated human immunodeficiency virus wherein the genome of the virus comprises a mutated tat gene and a mutated nef gene. The invention is not limited by the nature of the mutation in the tat and nef genes; insertions, deletions, substitutions may be employed to mutate the tat and nef genes. Preferably, the genome of the attenuated virus comprising a mutated tat gene and a mutated nef gene cannot express a functional Tat protein or a functional Nef protein. In a preferred embodiment, the attenuated virus is selected from the group consisting of $HIV_{CMV/tat-B}$, $HIV_{CMV/AD8/nef-B/tat-B}$, $HIV_{NL43/AD8/tat-B/nef-B}$ and $HIV_{NL43/nef-B/tat-B}$.

The invention further provides a DNA construct comprising the provirus of a replication-defective human immunodeficiency virus, wherein the DNA construct is selected from the group consisting of pHP-1, pHP-2 and pHP-3.

The invention also provides a method comprising: a) providing: i) a SCID/beige mouse; ii) human fetal hematopoietic tissue comprising human immune cells (e.g., fetal liver, bone marrow, thymus, lymph node); iii) an injectable preparation comprising one or more components derived from a human immunodeficiency virus vaccine; iv) a composition comprising non-attenuated human immunodeficiency virus; b) inserting the hematopoietic tissue under the kidney capsule of the mouse to provide a transplanted mouse; c) injecting the transplanted mouse with the vaccine to produce an injected mouse; d) exposing the injected mouse to the composition; and e) monitoring the exposed mouse for the presence of infection of the human immune cells by the non-attenuated human immunodeficiency virus. The invention is not limited by the non-attenuated virus employed; any virus capable of causing an non-attenuated infection may be employed. Preferably, the non-attenuated virus is a virus isolated from a patient with AIDS (i.e., a clinical isolate) or is a virulent laboratory strain. Particularly preferred non-attenuated HIV strains include the NL4-3 strain, the ADA strain and HIV-1 primary isolates covering the different HIV clades (e.g., 92RW008, 92BR003, 92HT593, etc. available from the NIH AIDS Research and Reference Reagent Program of National Institutes of Health, Bethesda, Md.).

In a preferred embodiment, the injecting of step b) is repeated at least once prior to exposing the mouse to the composition. The injectable preparation comprises a candidate vaccine; a candidate vaccine may comprise proteins or peptides or nucleic acids and may be immunogenic. However, as this method offers a means to evaluate candidate vaccines, some candidate vaccines are expected to be immunogenic (i.e., capable of invoking an immune response directed against the pathogen from which the protein, peptide or nucleic acid was derived) and some are expected to not be immunogenic (and would therefore be rejected as a vaccine for use in subject such as a human). In a preferred embodiment, the injectable preparation is immunogenic. The injectable preparation may comprise pharmacological carriers, excipients and adjuvants as discussed above.

The invention is not limited by the nature of the component of the HIV present in the injectable composition. In a preferred embodiment, the component of the HIV comprises at least a portion of a protein derived from a HIV; the component may be a complete protein molecule or a peptide derived from the complete protein (and may be produced by peptide synthesis, recombinant DNA methodologies or protease digestion of the intact protein). In another preferred embodiment, the component of the HIV comprises DNA derived from HIV. In a particularly preferred embodiment, the DNA comprises proviral DNA encoding a HIV genome capable of expressing viral structural genes but incapable of being packaged into viral particles. In a preferred embodiment, the DNA comprises plasmid DNA selected from the group consisting of pHP-1, pHP-2 and pHP-3.

In another embodiment, the injectable preparation comprises an attenuated replication-competent HIV (i.e., capable of producing only a limited infection and preferably incapable of producing the pathological changes associated with infection by a non-attenuated HIV). The invention is not limited by the nature of the change which renders the virus attenuated. In a preferred embodiment, the attenuated virus comprises a mutated tat gene; preferably, the genome of the attenuated virus cannot express a functional Tat protein. In another preferred embodiment, the genome of attenuated virus genome further comprises a mutated nef gene; preferably, the genome of the attenuated virus cannot express either a functional Tat protein or Nef protein. In a preferred embodiment, the attenuate virus is selected from the group consisting of $HIV_{CMV/tat-B}$, $HIV_{CMV/AD8/nef-B/tat-B}$, $HIV_{NL43/AD8/tat-B/nef-B}$ and $HIV_{NL43/nef-B/tat-B}$.

In another embodiment, the injectable preparation comprises attenuated Leishmania cells. The invention is not limited by the nature of the change which renders the Leishmania cell attenuated. In a preferred embodiment, the attenuated Leishmania cell comprises heterologous DNA encoding a cysteine protease gene as described above. In another preferred embodiment, the heterologous DNA further comprises DNA encoding a HIV gene selected from the group consisting of the env gene, the gag gene, the pol gene, the tat gene, the rev gene, the vif gene, the vpu gene, the vpr gene and the nef gene.

The invention is not limited by the nature of the monitoring employed to detect the presence (or absence) of infection of the human immune cells in the SCID/bg mouse comprising human immune cells (e.g., a hu-PBL-SCID/bg mouse) as described above.

The invention also provides an attenuated human immunodeficiency virus wherein the genome of the virus comprises a mutated tat gene and a mutated nef gene. The invention is not limited by the nature of the mutation in the tat and nef genes; insertions, deletions, substitutions may be employed to mutate the tat and nef genes. Preferably, the genome of the attenuated virus comprising a mutated tat gene and a mutated nef gene cannot express a functional Tat protein or a functional Nef protein. In a preferred embodiment, the attenuated virus is selected from the group consisting of $HIV_{CMV/tat-B}$, $HIV_{CMV/AD8/nef-B/tat-B}$, $HIV_{NL43/AD8/tat-B/nef-B}$ and $HIV_{NL43/nef-B/tat-B}$.

DESCRIPTION OF THE DRAWINGS

In FIG. 3A, all mice were reconstituted with PBLs while in FIG. 3B half the mice from both groups were left unreconstituted.

FIGS. 4A and 4B represent data from two separate experiments.

FIGS. 8A–8D show immunostaining for HIV-1 infected cells in peritoneal lavage (8A and 8C) and splenocytes (8B and 8D) of mice reconstituted with PBLs from a LR (8C and 8D) or HR individual (8A and 8B). FIG. 8E shows the percentage of HIV-1 infected cells in the peripheral blood, spleen and peritoneal lavage of hu-PBL-SCID/bg mice reconstituted with PBLs from a LR or HR individual and challenged with T cell or macrophagic tropic HIV-1.

FIGS. 10A–10D show FACS analysis of splenocytes derived from the reconstituted mice (10A and 10C no anti-CD8 treatment; 10B and 10D after anti-CD8 treatment). FIG. 10E shows the percentage of HIV-1 infected cells in the spleen and peritoneal lavage of hu-PBL-SCID/bg mice reconstituted with PBLs from a LR or HR individual, with or without anti-CD8 treatment, and infected with $HIV_{NLAD8}$.

FIGS. 11A–11F provide schematics showing the organization of the HIV-1 genome (11A) and the organization of the $HIV_{NL4-3}$ virus, (11B) $HIV_{NL43/AD8/tat-B/nef-B}$ (11C), $HIV_{NL43/nef-B/tat-B}$ (11D), $HIV_{CMV/nef-B/tat-B}$ (11E) and $HIV_{CMV/AD8/nef-B/tat-B}$ (11F) clones.

FIGS. 12A–B provide schematics showing a portion of the wild type HIV-1 sequence as well as the tat-B (FIG. 12A; wild-type sequence provided in SEQ ID NO:26) and nef-B mutations (FIG. 12B; wild-type sequence provided in SEQ ID NOS:27 and 28).

DEFINITIONS

Figure 1:
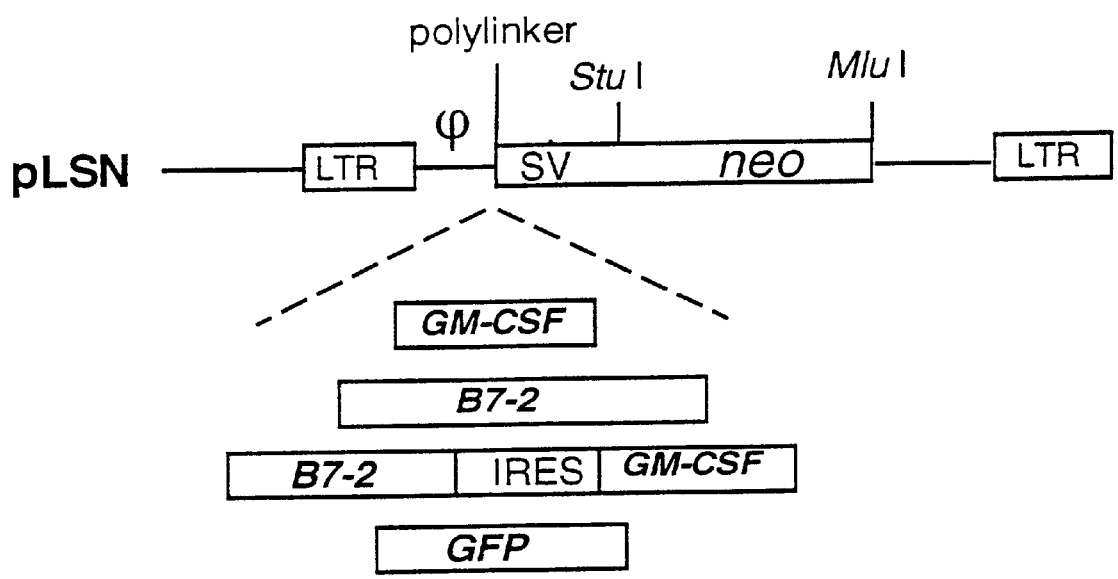
FIG. 1 provides a schematic showing the pLSN, pLSNB70, pLSNGM1, pLSN-BG9 and pLSN-GFP retroviral constructs.
Figure 2A:
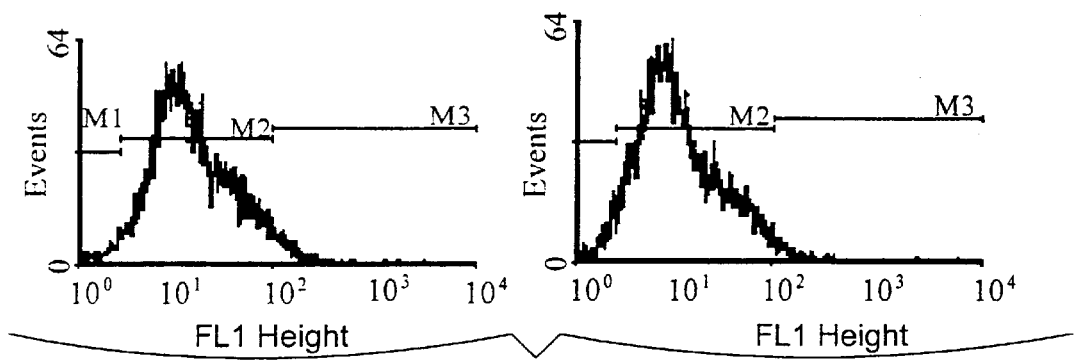
FIGS. 2A–E provide flow cytometry histograms for wild type D54MG cells (2A), B7-2-transduced D54MG cells (2B), GM-CSF-transduced D54MG cells (2C), B7-2 and GM-CSF-transduced D54MG cells (2D), and GFP-transduced D54MG cells (2E). For FIGS. 2A–2D, the histograms on the left represent D54MG cells stained with isotype matched control antibodies while the histograms on the right represent staining with monoclonal anti-human B7-2 antibodies. For FIG. 2E, the histogram on the left represents unstained wild type D54MG cells while the histogram on the right represents unstained GFP-transduced D54MG.
Figure 2B:
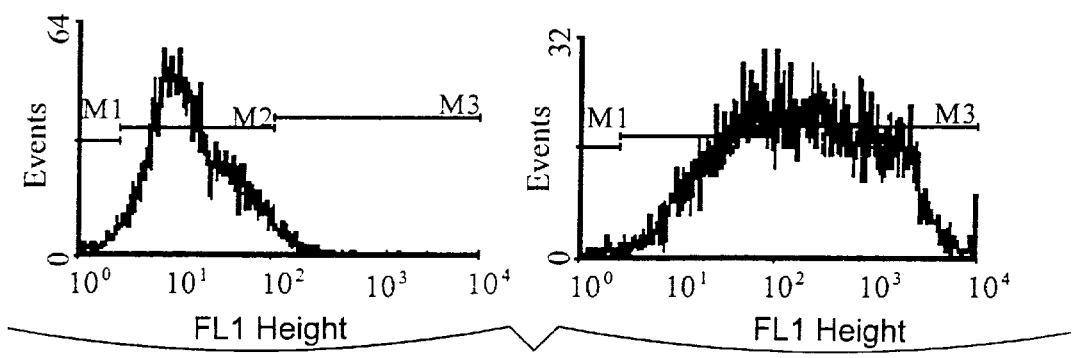
Figure 2C:
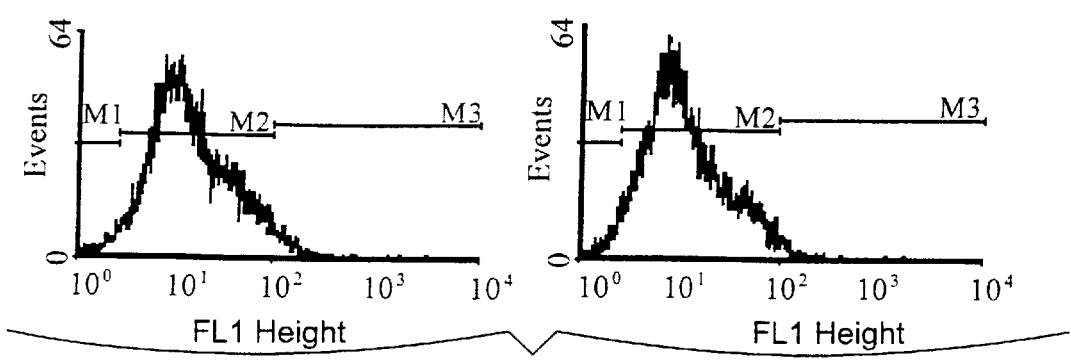
Figure 2D:
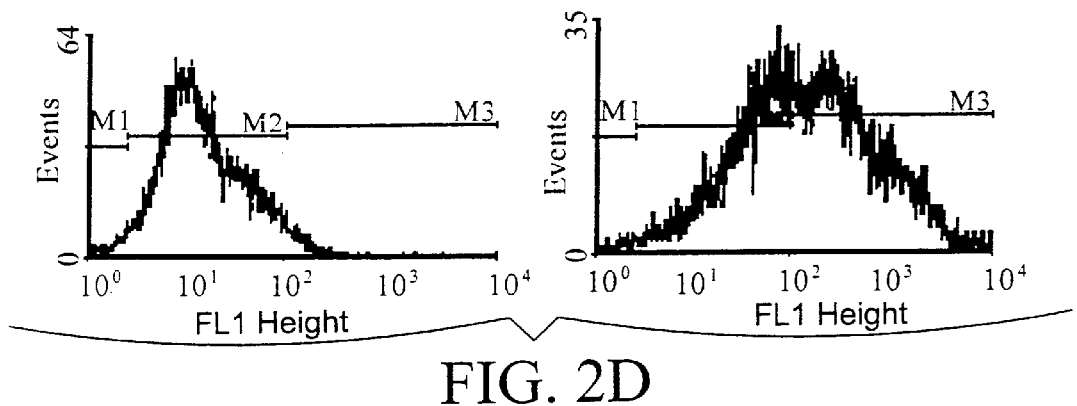
Figure 2E:
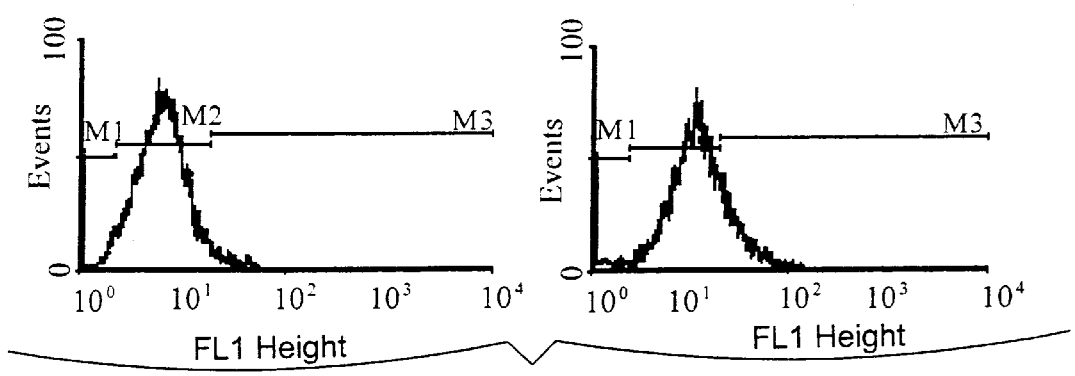

To facilitate understanding of the invention, a number of terms are defined below.

As used herein, "immunodeficient mouse" refers to a mouse or mouse strain which is deficient in immune system function, including at least a deficiency in function or presence of mature B and T lymphocytes. Examples of immunodeficient mouse strains include, but are not limited to the C.B-17-SCID-nod, C.B-17scid/scid and C.B-17-SCID-beige strains. Particularly preferred immunodeficient mice have a severe combined immunodeficiency characterized by a lack of mature T, B and natural killer (NK) lymphocytes (e.g., the C.B-17-SCID-beige mouse strain).

As used herein, "human T lymphocytes" refers to T lymphocytes of human origin. When present in a mouse reconstituted with human blood cells, the human T lymphocytes may be obtained from a variety of sources in the reconstituted mouse including blood (i.e., peripheral blood lymphocytes or PBLs), lymph nodes, spleen, peritoneal lavage, etc.

Human T lymphocytes are identified by the presence of certain markers or cell surface proteins including CD3, CD4, CD8, T cell antigen receptor (TCR) and CD45. The presence of these markers on a lymphocyte may be determined by standard immunocytological means such as incubation (or staining) of a cell suspension containing lymphocytes with antibodies specific for these markers; the antibodies may be directly labelled (e.g. with a fluorophore such as fluorescein, phycoerythrin, Texas Red, etc.) or the presence of the antibody bound to the surface of a lymphocyte may be detected using a secondary antibody (i.e., an antibody directed at the first antibody or a component thereof) that is labelled. The stained lymphocytes may then be analyzed using a fluorescence microscope or a FACS (fluorescence-activated cell sorter) analysis. "Mature human T lymphocytes" express either CD4 or CD8, CD3 and a TCR. "Immature human T lymphocytes" express both CD4 and CD8 (i.e., they are CD4+8+); these cells are also referred to as progenitor T cells. "Immature naive human T lymphocytes" are immature T lymphocytes that have not been activated (i.e., they have not engaged antigen specific for their TCR or been stimulated by a nonspecific mitogen) and are said to be naive. "Immature naive T lymphocytes" includes CD4+8+ T cells as well as CD45RA+ T cells.

A mouse comprising CD45+ T lymphocytes wherein at least 5% of the human CD45+ T cells represent immature naive T lymphocytes is a mouse in which 5% or more of the CD45+ T cells are either CD4+8+ or CD45RA+ or the sum of the % of CD45+ T cells that are CD4+8+ and CD45RA+ is at least 5%.

CD45 proteins are found on the surface all hematopoietic cells, except for erythrocytes [The Leukocyte Antigen Facts Book, Barclay et al. (1993), Academic Press, London, UK, pp. 202–204]. Different isoforms of CD45 are found on different lymphoid cell types; CD45RO is found on activated and memory T cells, whereas CD45RA is found on naive T cells.

The term "SCID/beige mouse" refers to the C.B-17-SCID-beige mouse strain. The terms SCID/beige, SCID-beige and SCID/bg are used interchangeably herein.

The term "human tumor cells" refers to tumor cells of human origin; a tumor cell is a neoplastic or cancerous cell. Tumor cells may be "established tumor cells," i.e., those which can be maintained indefinitely in tissue culture or may be "primary tumor cells," i.e., tumor cells freshly isolated or explanted from a patient. The term "primary tumor cells" encompasses primary tumor cells maintained in tissue culture for less than or equal to 5 passages.

The term "human immune cell" refers to cells of the immune system (e.g., T, B and NK lymphocytes, antigen presenting cells) that are of human origin.

The term "human peripheral blood lymphocytes" refers to nucleated, non-erythroid cells derived from the blood of a human. The terms peripheral blood lymphocytes (PBLs) and peripheral blood mononuclear cells (PBMCs) are used herein interchangeably.

The term "central nervous system cells" refers to cells derived from the central nervous system (i.e., cells derived from the brain and spinal cord).

A mouse "reconstituted with human peripheral blood lymphocytes" is a mouse in which human PBLs have been introduced (e.g., by intraperitoneal injection) and persist for a period of at least 4 weeks.

A "SCID/beige mouse comprising human immune cells" is a SCID/bg mouse that has been reconstituted with human PBLs or another source of human immune cells (e.g., human fetal hematopoietic tissues) and thus, contains human immune cells. SCID/beige mouse comprising human immune cells whose serum contains at least 100 μg/ml of human immunoglobulin (Ig) are preferentially employed for the evaluation of vaccines.

An "injectable preparation" is a preparation suitable for injection into an animal (e.g., a mouse).

An "immune-modulating gene" is a gene encoding a protein that modulates the immune response. Examples of immune-modulating genes include but are not limited to cytokines, costimulatory molecule and chemotactins. The product of an immune-modulating gene is said to be an "immune modulator." A "cytokine" is a hormone-like protein, typically of low molecular weight, that regulates the intensity and duration of the immune response and is involved in cell to cell communication. Examples of cytokines include but are not limited to the interleukins (e.g., interleukin 2, interleukin 4, interleukin 6, interleukin 7, interleukin 12), granulocyte-macrophage colony stimulating factor, granulocyte colony stimulating factor, interferon-gamma (IFN-γ) and tumor necrosis factor-alpha (TNF-α).

The term "cell cycle regulator" refers to any protein whose activity modulates progression of the cell cycle. Particularly preferred cell cycle regulators are those that block cell cycle progression. Examples include but are not limited to the HIV vpr gene product, p21, inhibitors of mammalian cyclins, etc.

The term "inducer of apoptosis" refers to any protein whose activity induces apoptosis in a cell. Inducers of apoptosis include but are not limited to apoptin (the product of the chicken anemia virus VP3 gene), BAX, BAD, a BCL-X derivative and the HIV vpr gene product.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

Transcriptional control signals in eucaryotes comprise "promoter" and "enhancer" elements. Promoters and enhancers consist of short arrays of DNA sequences that interact specifically with cellular proteins involved in transcription [Maniatis, et al., Science 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types [for review see Voss, et al., Trends Biochem. Sci., 11:287 (1986) and Maniatis, et al., supra (1987)]. For example, the SV40 early gene enhancer is very active in a wide variety of cell types from many mammalian species and has been widely used for the expression of proteins in mammalian cells [Dijkema, et al., EMBO J. 4:761 (1985)]. Two other examples of promoter/enhancer elements active in a broad range of mammalian cell types are those from the human elongation factor 1α gene [Uetsuki et al., J. Biol. Chem., 264:5791 (1989); Kim et al., Gene 91:217 (1990); and Mizushima and Nagata, Nuc. Acids. Res., 18:5322 (1990)] and the long terminal repeats of the Rous sarcoma virus [Gorman et al., Proc. Natl. Acad. Sci. USA 79:6777 (1982)] and the human cytomegalovirus [Boshart et al., Cell 41:521 (1985)].

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site [Sambrook et al., Molecular Cloning: A Laboratory Manual, 2nd ed., Cold Spring Harbor Laboratory Press, New York (1989) pp. 16.7–16.8]. A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation [Sambrook, supra, at 16.6–16.7]. This 237 bp fragment is contained within a 671 bp BamHI/PstI restriction fragment.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "stable transfection" or "stably transfected" refers to the introduction and integration of foreign DNA into the genome of the transfected cell. The term "stable transfectant" refers to a cell which has stably integrated foreign or exogenous DNA into the genomic DNA of the transfected cell.

The terms "selectable marker" or "selectable gene product" as used herein refer to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any mammalian cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with TK$^-$ cell lines, the carbamoyl-phosphate synthetase-aspartate transcarbamoylase-dihydroorotase (CAD) gene which is used in conjunction with CAD-deficient cells and the mammalian hypoxanthine-guanine phosphoribosyl transferase (hprt) gene which is used in conjunction with HPRT$^-$ cell lines. A review of the use of selectable markers in mammalian cell lines is provided in Sambrook et al., supra at pp. 16.9–16.15. It is noted that some selectable markers can be amplified and therefore can be used as amplifiable markers (e.g., the CAD gene).

DESCRIPTION OF THE INVENTION

The present invention provides humanized animal models suitable for the evaluation of anti-human tumor immunity. These animal models permit the identification of combinations of immune-modulating genes (IMGs) which when delivered to human tumor cells induce an effective anti-tumor response, including a systemic anti-tumor response. The Description of the Invention is divided into the following sections: I. Immunogene Therapy; II. Existing Animal Models For Immunogene Therapy; III. The Hu-SCID/beige Model For Immunotherapy; IV. Combination Immunogene Therapy; V. Evaluation Of Candidate Vaccines Using The Hu-PBL-SCID/beige Model; VI. HIV Vaccines and VII. Alternative Strategies For Cancer Therapy And vaccine Production.

I. Immunogene Therapy

Immunogene therapy involves the introduction of genes encoding proteins that regulate or modulate the immune response and particularly those that are involved with the activation of T cells. As discussed above, the majority of tumors are not immunogenic, i.e., they fail to provoke an immune response. Several reasons for the lack of immunogenicity of tumor cells have been proposed including the lack of cell surface molecules on the tumor cell that are required to transduce costimulatory signals that are required in order for T cells to secrete cytokines, proliferate, induce effector function and prevent anergy. As most tumor cells are not derived from professional APCs which normally present antigen and provide costimulatory signals to T cells, it is not surprising that the majority of tumor cells fail to induce a tumor-specific response even when the tumor cell bears a tumor-specific antigen.

In an attempt to increase the immunogenicity of tumor cells, genes encoding co-stimulatory proteins and/or cytokines have been introduced into tumor cells. The modified tumor cells are then examined for their ability to induce an anti-tumor response (in vivo or in vitro). As discussed below, these experiments have been carried out in animal models (e.g., in mice and rats) and the results have been conflicting leading some in the field to question the utility of existing animal models for the development of immunogene therapy protocols aimed at the treatment of humans.

II. Existing Animal Models For Immunogene Therapy

The majority of the existing animal models for immunogene therapy involve the use of immunocompetent syngeneic animals (e.g., mice and rats) and established tumor cell lines. Typically, one immunogene (e.g., mouse IL-2) is introduced into an established mouse tumor cell line, the tumor cells are selected in culture to identify cells expressing the transferred immunogene and the modified tumor cells are injected into recipient mice and the mice are examined for the presence of tumors. In some experiment, the mice receive irradiated modified tumor cells as a vaccine followed by a challenge with unmodified tumor cells (vaccination/challenge experiment). In some cases, the expression of certain immunogenes has been shown to increase the immunogenicity of the tumor cell (i.e., to reduce the tumorigenicity of the tumor cell). An experimentally induced animal tumor is said to be immunogenic if the tumor is rejected following transplantation into syngeneic animals previously immunized or vaccinated with irradiated cells of the same tumor. Nonimmunogenic tumors are not rejected under these conditions.

Overall the results of these syngeneic animal experiments have been conflicting. For example, the expression of the costimulatory molecule B7-1 in the mouse melanoma cell line B-16 was found to lead to the rejection of B7-1 expressing B-16 cells in syngeneic mice in one study [Wu et al. (1995) J. Exp. Med. 182:1415] while in another study B7-1-expressing B-16 cells were found to be tumorigenic [Chen et al. (1994) J. Exp. Med. 179:523]. In the case where B7-1 expression was found to increase the immunogenicity of B-16 cells, the authors reported that animals that rejected the modified B-16 cells did not develop an enhanced systemic immunity against unmodified or wild type B-16 cells [Wu et al., supra]. In another study, the expression of B7-1 or B-72 in mouse colorectal tumor or melanoma cells was found to confer a local anti-tumor response in immunocompetent mice [Chong et al. (1996) Human Gene Ther. 7:1771]. However, no systemic immunity was conferred by vaccination of mice with B7-1 or B7-2 expressing colorectal tumor cells and the expression of B7-1 or B7-2 in the melanoma cells was found to reduce the systemic immunity conferred by the B7-expressing cells relative to that conferred by vaccination with wild type melanoma cells even when the B7-expressing cells also expressed interferon-γ (Chong et al., supra).

It has been reported that the rejection of B7-1 expressing tumor cell lines is limited to highly immunogenic cell lines as B7-1 expression in poorly immunogenic fibrosarcomas (e.g., MAC101, MCA102 and Ag104) and the B-16 melanoma cell line does not reduce the tumorigenicity of these lines. As discussed above, expression of B7-1 in the B-16 melanoma cell line was found by one group to reduce the tumorigenicity of these cells (Wu et al., supra). This discrepancy may be explained by differences in the level of B7-1 expression achieved by different groups. However, tumor cells expressing only B7-1 have been found to be ineffective in inducing the rejection of established tumors.

The failure of B7-1 alone to induce the rejection of established tumors was postulated to be due to the induction of a state of anergy in potentially reactive T cells. Therefore, combinations of B7-1 and cytokines were tested to see if this state of anergy could be overcome. Combinations of costimulatory molecules and various growth factors or cytokines has proven to be more effective than the use of either category of molecules alone. For example, the expression of B7-1 in the mouse NC adenocarcinoma cell line was found to have no effect on the tumorigenicity of these cells in immunocompetent syngeneic mice [Gäken et al. (1997) Human Gene Ther. 8:477]. However, the expression of both B7-1 and IL-2 in the NC adenocarcinoma cell line substantially reduced the tumorigenicity of these cells in mice.

While existing animal models have demonstrated that in general a combination of costimulatory molecules and a cytokine and/or a chemokine is preferable to the use of any one of these groups alone, the data from different groups using combinations of these molecules is conflicting. For example, Dilloo et al. reported that mice immunized with A20 B cell lymphoma cells mixed with IL-2 and the chemokine lymphotactin developed a potent anti-tumor response while mice immunized with B cell lymphoma cells mixed with GM-CSF developed a much reduced anti-tumor response [Dilloo et al. (1996) Nature Med. 2:1090]. On the other hand Levitsky et al., reported that vaccination of mice with GM-CSF-expressing A20 B lymphoma cells lead to a complete rejection of pre-established A20 tumors while vaccination with either I1-2-expressing or B7-1-expressing A20 cells did not [Levitsky et al. (1996) J. Immunol. 156:3858]. This apparent conflict lead Dilloo and Brenner to remark that "it [is] difficult to be confident that current murine models can be used to pick the "best" cytokine for a particular human tumor." [Nature Med. (1997) 3:126]. Clearly the art needs improved models for determining which cytokines, costimulatory molecules and/or chemotactins, or which combination thereof is best suited for the treatment of particular human tumors.

III. The Hu-PBL-SCID/beige Model For Immunotherapy

The present invention provides novel humanized animal models for human immunogene therapy. As discussed above, most preclinical immunogene therapy studies have employed murine genes and murine tumor models. The applicability of such models to humans systems is unclear. Therefore, a humanized mouse model utilizing human tumor cells (either established cell lines or primary tumor cells), human immunogenes and human lymphocytes was developed and is provided herein.

The C.B-17 SCID/beige (SCID/bg) mouse, an immunocompromised mouse, was employed for the humanized mouse model as this strain of mice lacks T cell, B cell and natural killer (NK) cell function [Froidevaux and Loor (1991) J. Immunol. Methods 137:275]. As shown herein, the SCID/bg mouse supports the growth of a variety of established human tumor cell lines as well as primary human tumor cells. SCID/bg mice were efficiently reconstituted with human peripheral blood lymphocytes (PBLS) with CD45+ human cells constituting up to 60% of the splenocytes and 2–7% of the peripheral blood mononuclear cells in the reconstituted mice.

Importantly, the peripheral blood of the Hu-PBL-SCID/bg mice were found to contain high numbers of immature or progenitor T cells (i.e., CD4+8+ cells and CD45RA+ cells). These results are in contrast to the results obtained by reconstitution of C.B-17scid/scid mice (Hu-PBL-SCID). In human PBL-reconstituted C.B-17 scid/scid mice, most human lymphocytes exhibit activated cell phenotypes (HLA-DR+ and CD25+ or CD69+) soon after reconstitution, and almost all (>99%) human T cells exhibit mature memory phenotypes (CD45RO+) in a state of reversible anergy [Rizza et al., supra; Tarry-Lehmann and Saxon, supra; Tarry-Lehmann et al. (1995), supra]. Therefore, the lack of sufficient numbers of immature naive T cells after reconstitution renders the Hu-PBL-SCID model unsuitable for the evaluation of anti-tumor immunity. In contrast, the Hu-PBL-SCID/bg mice show evident levels of CD45RA+ and CD4+8+ cells 4–6 weeks after reconstitution. Thus, the Hu-PBL-SCID/bg mice of the present invention provide a suitable model for the evaluation of anti-tumor immunity.

The use of the Hu-PBL-SCID/bg mice as a model for human immunogene therapy is illustrated herein for the identification of a combination of immune-modulating genes (IMGs) effective in the treatment of human glioblastoma multiforme.

Glioblastoma multiforme is the most common primary central nervous system neoplasm in humans. Despite improvements in diagnosis and treatment of glioblastoma multiforme, mean survival from time of diagnosis remains less than one year [Chang et al. (1983) Cancer 52:997; McDonald and Rosenblum (1994) In: *Principles of Neurosurgery*, Regachary and Wilkins, eds., Wolfe Publishing, Toronto, pp. 26.21–26.32].

Although glioblastomas in situ are normally infiltrated to varying degrees by lymphocytes [Kuppner et al. (1989) J. Neurosurgery 71:211; Black et al. (1992) J. Neurosurgery 77:120], evidence indicates these lymphocytes are unactivated. This may be in part due to secretion of immunosuppressive factors such as prostaglandin $E_2$, transforming growth factor $\beta_2$, and interleukin-10, all of which inhibit lymphocyte activation [Fontana et al. (1982) J. Immunol. 129:2413; Siepl et al. (1988) Eur. J. Immunol. 18:593; Kuppner et al., supra; Sawamura et al. (1990) J. Neuro-Oncol. 9:125; Nitta et al. (1994) Brain Res. 649:122; Huettner et al. (1995) Am. J. Pathol. 146:317]. Immunogene therapy strategies were designed to overcome such local immunosuppression by promoting tumor antigen presentation and/or anti-tumor lymphocyte activation.

As discussed above, most preclinical immunogene therapy studies have used rodent genes and rodent tumor models. However, the applicability of such models to human systems is unclear. This is particularly true for glioblastoma models utilizing rodent tumors (rat 9L-glioma and C6-glioma) which have sarcomatous features that are significantly different from human glioblastoma multiforme [Benda et al. (1968) Science 161:370; Barker et al. (1973) Cancer Res. 33:976; Day and Bigner (1973) Cancer Res. 33:2362]. Therefore, the present invention provides a novel humanized mouse model utilizing a human glioblastoma cell line, human immunogenes and human lymphocytes.

Using retroviral vectors, genes encoding human GM-CSF and/or B7-2 were efficiently transferred in vitro into a human glioblastoma cell line. Thereafter, the effect of GM-CSF and/or B7-2 expression on glioblastoma growth in vivo was examined in a human tumor/human PBL/severe combined immunodeficiency mouse (hu-PBL-SCID) model. Human glioblastoma cells (with or without therapeutic gene transfer) and human PBLs were grafted into SCID/bg or SCID/nod mice and the effect on tumor growth locally and at distant sites was observed. SCID/bg and SCID/nod mice accept human tumor and lymphocyte grafts without rejection as they lack mature T, B, and NK lymphocytes.

As shown herein, inhibition of GM-CSF and B7-2-transduced tumors was seen in human lymphocyte-reconstituted SCID/bg mice demonstrating that expression of these genes by glioblastoma cells overcomes local immunosuppression and results in a significant antitumor immune response. Furthermore, inhibition of wild type challenge growth in mice vaccinated with irradiated tumor cells transduced with B7-2 and GM-CSF demonstrated that expression of these genes by glioblastoma cells induced a systemic immune response that inhibits tumor growth at distant sites. These results provide the first in vivo demonstration of human GM-CSF immunogene therapy in a human glioblastoma model.

The human glioblastoma-Hu-PBL-SCID/bg model employed herein represents an allogeneic system that comprises an established human glioblastoma cell line and lymphocytes from unrelated donors. This model has more similarities to autologous systems than may be immediately apparent. Unlike the classical immune-mediated rejection seen in allogeneic organ transplantation, this system is free of graft-origin "passenger lymphocytes." These lymphocytes are important in initiating allogeneic organ rejection responses by presenting antigen to host lymphocytes in the context of allogeneic Class II Major Histocompatibility Complex (MHC) [Larsen et al. (1990) Annals Surgery 212:308; Chandler and Passaro (1993) Archives Surg. 128:279; Moller (1995) Transplantation Proc. 27:24]. The D54MG glioblastoma cell line employed in this model expresses only Class I MHC and not Class II MHC in vitro. Therefore, the only Class II MHC molecules available for tumor antigen presentation in this model are those present on engrafted human PBLs. In other words, this model glioblastoma system is allogeneic for Class I MHC but autologous for Class II MHC.

As described herein, the human tumor/Hu-PBL-SCID/bg model can be used as an autologous model system comprising human tumor cells and PBLs from the same patient. Such an autologous model is preferred to an allogeneic model system; however, for certain rapidly progressing tumors it may be difficult to obtain PBLs from the same patient once the patient's tumor has been established in the Hu-PBL-SCID mice. In these cases, an allogeneic model, using PBLs from a donor unrelated to the tumor donor is employed.

The human tumor/Hu-PBL-SCID/bg model of the present invention provides a simple and powerful method to analyze human lymphocyte responses to human tumors in vivo and thus provides a means to determine which combination of IMGs are best suited for the treatment of specific tumors.

IV. Combination Immunogene Therapy

The human tumor/Hu-PBL-SCID/bg model of the present invention provides a simple and powerful method to determine which combination of IMGs or IMGs and/or cell cycle regulators, inducers of apoptosis and tumor suppressor genes (e.g., the wild type p53 gene) are best suited for the treatment of specific tumors.

Many immunomodulatory genes are potentially useful and more than one may be necessary for overcoming tumor immunosuppression. These include genes encoding cytokines, major histocompatibility complex molecules, and T cell costimulatory molecules [Dranoff et al. (1993) Proc. Natl. Acad. Sci. USA 90:3539; Gajewski et al. (1995) J. Immunol. 154:5637]. An ideal tumor vaccine should coexpress a combination of immunostimulatory genes from distinct immunomodulatory pathways (e.g., costimulators, cytokines, and chemoattractive adjuvants) and may also express cell cycle regulators, inducers of apoptosis and tumor suppressor genes.

In the illustrative example provided herein, a combination of the therapeutic cytokine granulocyte-macrophage colony stimulating factor (GM-CSF) and the T cell costimulatory molecule B7-2 was employed to increase the immunogenicity of a human glioblastoma cell line.

GM-CSF stimulates growth and differentiation of granulocytes, monocytes/macrophages, microglia, and other antigen presenting cells. It has recently come into widespread clinical use as a treatment of neutropenia due to its hematopoietic effects [Lieshcke and Burgess (1992) N. Engl. J. Med. 327:28; Aglietta et al. (1994) Seminars Oncol. 21:5; Engelhard and Brittinger (1994) Seminars Oncol. 21:1]. The importance of this cytokine in tumor immunogene therapy was recently demonstrated by Dranoff, et al. who showed that vaccination with irradiated GM-CSF-transduced tumor cells produced specific and marked growth inhibition of wild type tumor challenges in mouse models of adenocarcinoma and melanoma [Dranoff et al., supra]. Of 10 cytokine genes tested, GM-CSF resulted in the greatest tumor growth inhibition in this mouse model.

B7-2 is one of a family (B7-1, B7-2, and B7-3) of lymphocyte cell surface molecules that have recently been identified as costimulatory molecules necessary for T-cell activation in conjunction with antigen presentation in the context of a major histocompatibility complex molecule. The absence of costimulatory molecules on tumor cells may contribute to their failure to be detected and eliminated by the immune system [Galea-Lauri et al. (1996) Cancer Gene Ther. 3:202]. The specific roles of the various costimulatory molecules are yet to be clearly defined. It has been suggested that B7-1 expression promotes differentiation of intermediate $T_H$ cell precursors into $T_H1$ effector cells (cellular immune responses) while B7-2 expression leads to $T_H2$ differentiation (humoral immune responses) [Kawamura and Furue (1995) Eur. J. Immunol. 25:1913; Thompson (1995) Cell 71:979]. However, both B7-1 and B7-2 have been shown to promote cell mediated immune responses in animal models [Hodge et al. (1994) Cancer Res. 54:5552; Lanier et al. (1995) J. Immunol. 154:97; Plumas et al (1995) Eur. J. Immunol. 25:3332]. More recently, the effectiveness of B7-1 expression in promoting tumor rejection has been questioned (Wu et al., supra). Furthermore, T cells must receive costimulatory signals from APCs within the first 12 hours of T cell receptor stimulation for maximal interleukin-2 production [Mondino and Jenkins (1994) J. Leuckocyte Biol. 55:805]. Therefore, the rapid induction of B7-2 (not B7-1) on APC's after antigen stimulation suggests that B7-2 is the preferable costimulatory molecule to promote antitumor cell-mediated immune responses (Galea-Lauri et al., supra).

Other IMGs to be examined for their effectiveness in treating human tumors in the novel animal models of the present invention include, but are not limited to, APO-1 (Fas), APO-1 ligand (FasL) [Hahne et al. (1996) Science 274:1363; Seino et al. (1997) Nature Med. 3:165; Strand et al. (1996) Nature Med. 2:1361], IL-12A and IL-12B, IL-2, IL-4, IL-6, IL-7, IL-10, GM-CSF, G-CSF, IFN-γ, CD40 and TNF-α. In addition, genes encoding cell cycle regulators or inducers of apoptosis may be employed in combination with IMGs for the modification of tumor cells. Expression vectors, including retroviral vectors, containing one or more IMG (and/or cell cycle regulators or inducers of apoptosis)

are constructed as described herein. When more than one IMG (or genes encoding cell cycle regulators or inducers of apoptosis) is to be contained on the same construct, each IMG is preferably separated from the other(s) using an IRES as described herein. A particularly preferred IRES is the poliovirus IRES.

Once an effective combination of IMGs has been identified for a particular human tumor, those IMGs are delivered to a patient's tumor cells in vivo or in vitro followed by a return of the modified tumor cells (typically the modified cells will be irradiated prior to introduction) to the patient. As described more fully in the examples below, a variety of means may be employed for the delivery of IMGs to human tumor cells (e.g., biolistic transformation of tumor cells in situ, cationic liposomes, retroviral infection, etc.).

a. Combination Immunogene Therapy For Glioblastoma Using B7-2 and GM-CSF

As shown in the examples below, the human tumor/Hu-PBL-SCID/bg model of the present invention was employed to determine that tumor growth was markedly inhibited when these animals were vaccinated with glioblastoma cells transduced with genes encoding the T cell costimulatory molecule B7-2 and the proinflammatory cytokine GM-CSF.

Treatment of patients having glioblastoma multiforme tumors is conducted as follows. One to three grams of tumor are harvested when patients originally present and undergo surgery. The tissue is harvested and treated as described in Ex. 11. Tumor cells are grown until sufficient numbers are present to allow retroviral gene transfer and selection.

The primary tumor cells are transfected with pLSNBG9 (encodes both B7-2 and GM-CSF) and selected by growth in the presence of G418 as described below. Briefly, virus stock is thawed from −80° C. at 37° C. Polybrene is added to the thawed virus solution at a final concentration of 4 $\mu$g/ml. Culture medium is added to the virus solution to bring the final volume to 1.5 ml. Logarithmic growth phase tumor cells in T25 flasks are incubated in the virus supernatant at 37° C., 5% $CO_2$ for 3 hours. The same volume of medium containing polybrene but lacking virus is used as a control. After 3 hours, a further 3 ml of culture medium is added to each flask and the cells are incubated overnight. Medium is changed the next morning. Twenty-four hours after retroviral transduction, 200 $\mu$g/ml (final concentration) of the neomycin analog G418 is added to the culture medium. Medium is changed every 2 to 3 days until complete selection has taken place (i.e., all cells in the control flask are dead). After selection, cells are cultured in growth medium containing reduced concentrations of G418 (100 $\mu$g/ml) and are allowed to grow to confluence.

Transduced tumor cells are split into a new T25 culture flask at a density of $1 \times 10^6$ cells. the amount of GM-CSF secreted into the culture medium is determined by ELISA (Quantikine, R&D Systems) 24 hr later. B7-2 expression is evaluated by flow cytometry using a monoclonal antibody specific for the human B70 antigen (i.e., B7-2). Aliquots of transduced cells to be used as vaccines are tested for the presence of bacteria, fungi, mycoplasma, HIV, Hepatitis B and Hepatitis C and replication-competent retrovirus (using the standard S+L-assay; Bassin et al. (1971) Nature 229:564).

Tumor cells that have been transduced with GM-CSF and B7-2 genes, selected and expanded are cyropreserved for future use. Briefly, cells are aliquoted in small volumes into cryopreservation tubes at $1 \times 10^6$ cells/tube. Total volume is made up to 0.5 ml with a mixture of DMEM/F12, FCS and DMSO to make a final concentration of 10% FCS and 20% DMSO. Cells are placed in an insulated styrofoam rack and placed at −80° C. for 24 hr, then placed in liquid nitrogen for long term storage. When cells are needed, they are thawed from liquid nitrogen at 37° C., washed twice in fresh medium and plated.

Transduced tumor cells are irradiated prior to their reinjection into patients to render the cells replication incompetent. Cells are irradiated with 20,000 Rad in a $^6$Cobalt machine.

Patients are given three subcutaneous injections in total. Each vaccination comprises $2 \times 10^6$ irradiated autologous tumor cells modified to express B7-2 and GM-CSF. Injections are given on alternating lumbar flank regions which are marked immediately above the injection site with India ink to allow accurate localization later in the event that a local reaction is not apparent. Patients receive 0.1 ml of vaccine injected SC at each site using a 1 ml syringe fitted with a 23 gauge needle. All vaccinations are prepared by resuspension of cells in sterile Ringer's lactate solution. Patients having recurrent glioblastomas, the first injection is given on the first or second post-operative day. For patients with treatment resistant melanomas (discussed below), the timing of the first injection is not as critical as these patients are not undergoing any further surgical resection of their tumors. All patients receive a second and third vaccination 14 and 28 days, respectively after the first vaccination.

With the exception of the first vaccination in patients with recurrent glioblastomas (who are likely post-operative inpatients at the time), all subjects are treated as outpatients. Vital signs are monitored prior to immunization and every half hour for 3 hours after the SC injections. Patients are examined every hour for 3 hours for inflammation at the injection site and for evidence of rash, wheezing or edema. Provided there are no contraindications, subjects are discharged 3 hours after treatment. Should significant reactions occur, the patient is hospitalized for constant monitoring.

Patients are assessed in the clinic 3 days after vaccination and are evaluated weekly for 8 weeks and thereafter monthly for 4 months, every 3 months for 1 year and yearly thereafter. Blood samples are obtained for standard blood chemistries and histology at each visit. In addition, blood id drawn one week after each vaccination for replication-competent retrovirus assays.

Patients are observed for any toxicities. Patients' immunologic reaction to immunogene therapy is monitored locally and systemically. Local immune response is monitored by symptoms and signs of delayed type hypersensitivity (DTH) responses at the vaccination sites. In addition, punch biopsies are performed at injection sites 2 weeks after each vaccination (i.e., days 14, 28 and 42). These biopsies are compared to a biopsy taken from normal lumbar flank skin on day 1 (prior to initiation of therapy). Biopsies undergo standard pathological examination for evidence of tumor cells and inflammation. In addition, immunohistochemical staining for CD45, CD4, CD8 and NK cell markers is performed.

Systemic immune responses are measured using two separate assays. Blood samples (20 ml each) are obtained on days 0, 7, 21, 35 and 49. These samples are used to isolate peripheral blood mononuclear cells (PBMC or PBLs) by centrifugation on a density (Hystopaque) gradient. The PBMC are then stimulated in vitro by co-incubation for 5 days with irradiated (20,000 Rad) autologous tumor cells. The stimulated PBMC are then used in the following two assays. First, a standard $^{51}$Chromium release cytotoxic T lymphocyte (CTL) assay is performed vs. autologous tumor cells. Second, an ELISPOT assay for interferon-$\gamma$ production after exposure to autologous tumor cells is performed

[Zhang et al. (1996) Proc. Natl. Acad. Sci. USA 93:14720]. The $^{51}$Chromium release CTL assay is a standard assay for cell mediated immunity. This assay gives direct information concerning the ability of stimulated PBMC to kill tumor cells; however it has a relatively low sensitivity. To overcome this, the much more sensitive ELISPOT assay for interferon-γ production is also used. The ELISPOT assay determines the concentration of PBMC present that produce interferon-γ in response to exposure to autologous tumor cells. Since interferon-γ production is closely associated with $T_H1$ (cell mediated) immune responses, the number of PBMC producing interferon-γ in response to exposure to autologous tumor provides a measure of cell mediated immunity.

The clinical status of patients is followed by history, physical and laboratory parameters. In addition, appropriate diagnostic imaging tests (e.g., MRI scans with and without gadolinium enhancement) are obtained at 8 and 24 weeks, every 3 months for the following year, and yearly thereafter.

b. Combination Immunogene Therapy For Malignant Melanoma Using B7-2 and GM-CSF

Malignant melanoma is rapidly rising in North America. In contrast to other forms of skin cancers which are usually curable with surgery, malignant melanoma is often fatal due to its aggressive nature and tendency of early spread to distant organs. the treatment of primary melanoma is surgical while chemotherapy is indicated in patients with metastatic disease. Unfortunately, clinical response to chemotherapy is approximately 25% and 5 year survival is approximately 5%.

Treatment of patients having malignant melanoma is conducted using tumor cells modified to express B7-2 and GM-CSF as described above. Tumor cells are harvested from patients when patients originally present and undergo surgery and the cells are treated as described in Ex. 11.

Combinations of other IMGs (and/or genes encoding cell cycle regulators or inducers of apoptosis) shown to be effective at reducing tumorigenicity and or at inducing local or systemic immunity in the human tumor/Hu-PBL-SCID/bg model of the present invention are employed to treat human tumors, including glioblastoma and malignant melanoma.

In addition to the method of treatment described above wherein the patient's tumor cells are transduced with retroviruses encoding immune-modulators (e.g., B7-2 and GM-CSF) (and/or cell cycle regulators or inducers of apoptosis) and the tumor cells are selected in culture prior to reintroduction into the patient, the patient's tumor cells may be modified by introduction of DNA encoding the desired gene(s) (e.g., plasmid DNA transferred by biolistics or other physical means, recombinant adenoviruses, liposomes, direct injection of naked DNA). The cells are then allowed to express the transduced genes for a few days (or less), irradiated and used to immunize the patient. Subsequent boost immunizations may employ retrovirally transduced and selected tumor cells. The use of plasmid DNA (delivered by liposomes, biolistics, adenovirus vectors or as naked DNA) to modify tumor cells is preferred to the use of recombinant retroviruses in those cases where the patient's tumor cells take a lengthy period to grow in cell culture as retroviral transduction and selection takes a period of several weeks and for certain tumors (e.g., glioblastomas) it is desirable to vaccinate the patient with modified tumor cells within a few days (e.g., ~3) of the initial surgery. Vaccination within ~3 days of tumor debulking may permit the capture of the "alarm signal" required for costimulator activation on APCs and enhancement of activated macrophage and T cell traffic across the blood-brain barrier [Fuchs and Matzinger (1992) Science 258:1156 and Matzinger (1994) Annu. Rev. Immunol. 12:991].

V. Evaluation Of Candidate Vaccines Using The Hu-PBL-SCD/beige Model

As discussed above, the present invention provides humanized animal models that are useful for the evaluation of tumor cell vaccines. The hu-PBL-SCID/beige mice of the present invention also provide animal models for the evaluation of vaccines designed to confer immunity against a variety of human pathogens. The examples below provide detailed protocols for the establishment of hu-PBL-SCID/bg mice and humanized SCID/bg mice (i.e., SCID/bg mice comprising transplanted human fetal hematopoietic tissues). These animals contain human immune cells and are used to evaluate candidate vaccines (e.g., HIV vaccines, malaria vaccines, Leishmania vaccines, *M. tuberculosis* vaccines, etc.). Both cellular anti-pathogen immunity and humoral anti-pathogen immunity is assessed in the reconstituted and vaccinated animals.

The immunization efficacies of heterologous vaccines of human pathogens can be evaluated in SCID/beige mice intraperitoneally injected with human peripheral blood mononuclear cells (PBMCs) or receiving human fetal thymus/liver tissue transplants. In vivo human immune cell reconstitution in these animals has been demonstrated by analyzing the expression of different human leukocyte markers, including markers for naive T cells (CD45RA), memory T cells (CD45RO), activation (HLA-DR) and CD4 and CD8 cells. The in vivo immune functions of the human cells in the reconstituted animals have been demonstrated using an HIV-1 protective immunity model (see e.g., Ex. 16), and an attenuated Leishmania cell vaccine model (see Ex. 19). Other examples including immunization against malaria and tuberculosis with DNA vaccines encoding malaria multistage antigens or antigens of Bacille Calmette-Guerin (BCG) strains. SCID/beige mice are injected with freshly isolated PBMCs as described and one week later, human Ig levels are determined by ELISA. Hu-PBL-SCID/bg mice whose serum contains greater than 100 microgram/ml of human Igs are immunized via intramuscular injection with naked DNA vaccines or with dendritic cells (DCs) transfected with naked DNA vaccines which express appropriate pathogen antigens. The immunized mice are re-immunized 1–2 weeks later. The immunized mice are challenged with wild type pathogens such as HIV-1, malaria, *Mycobacterium tuberculosis* or Leishmania major one week after the last dose of vaccine. The control mice receive DNA vaccines lacking genes encoding the pathogen antigens. After wild type pathogen challenge, infection and/or disease development is examined according to standard methodology. The human immune cell-originated anti-pathogen immunity is analyzed, for cell-mediated immune (CMI) responses using reconstituted mouse splenocytes, and for humoral immune responses using antisera.

VI. HIV Vaccines

The examples below provide details for the production of HIV vaccines, including live attenuated HIV vaccines, HIV proviral DNA vaccines and modified Leishmania cells expressing HIV proteins. The ability of these HIV vaccines to induce cellular anti-HIV immunity and humoral anti-HIV immunity is assessed in hu-PBL-SCID/bg mice (reconstituted with PBLs or transplanted with fetal hematopoietic tissue) as described above and in the examples below.

VII. Alternative Strategies For Cancer Therapy and Vaccine Production

In addition to the approaches outlined above for the induction of immune responses to tumor cells and human pathogens, the following alternative approaches are provided.

a) Use Of Replication-Competent Viruses Comprising Suicide Genes

As discussed above replication-incompetent MoMLV-based vectors can be employed to deliver therapeutic genes to tumor cells (section IV). Another approach to delivering genes to tumor cells for the purpose of cancer therapy is the use of replication-competent retroviral vectors (e.g., MoMLV-based vectors) carrying "suicide" genes [e.g., the Herpes simplex virus thymidine kinase (HSV tk) gene]. A suicide gene is a negative selectable marker whose expression can be selected against. That is under certain conditions, cells expressing the suicide gene are selectively killed. For example, cells expressing the HSV tk gene are killed when they are grown in the presence of gancyclovir. The HSV tk gene has been employed for cancer gene therapy. Expression vectors containing the HSV tk gene were injected into the brains of patients having brain tumors and the patients were given gancyclovir. These experiments have met with little success as expression of the HSV tk gene was limited to cells along the injection track only; that is the HSV tk gene could not be delivered to enough of the tumor cells using this approach to kill enough tumor cells to make a difference in the outcome of the disease.

To deliver a suicide gene to a large percentage of the tumor cells in a patient, a replication-competent retroviral vector is employed. Retroviruses, such as MoMLV, preferentially infect rapidly dividing cells; as tumor cells are generally the most rapidly dividing cells in a patient, retroviruses may be employed to deliver genes to the tumor cells. The use of a replication competent retroviral vector permits the spread of the therapeutic gene to tumor cells outside of cells located at the site of injection of the vector. Replication-competent MoMLV vectors suitable for the delivery of HSV tk include, but are not limited to, Moloney leukemia virus (MLV) vectors [RNA Tumor Viruses (1995) *Molecular Biology of Tumor Viruses*, Cold Spring Harbor Laboratory Press, Cold Spring Harbor, N.Y.]. The HSV tk gene is inserted into the MoMLV vector using standard recombinant DNA techniques to create a suicide vector and DNA comprising the suicide vector is prepared. The suicide vector DNA is injected into the patient's tumor (intratumor injection) and the patient is then given gancyclovir (i.v. injection) to permit the killing of tumor cells expressing the HSV tk gene.

b) In Situ Production Of Producer Cells

In addition to the use of replication-defective retroviral vectors, attenuated viruses as a means of delivering vaccines for cancer therapy or the prevention of pathogenic infections, the present invention contemplates the injection of DNA constructs encoding the components necessary for the packaging of a retroviral vector along with a therapeutic vector into the tumor cells of a patient. Three separate DNA constructs are injected: 1) a DNA expression vector encoding the gag-pol genes of a retrovirus (e.g., MoMLV); 2) a DNA expression vector encoding the envelope gene of a retrovirus or a vesicular stomatitis virus G protein; and 3) a replication-defective retroviral vector (e.g., a vector lacking packaging signals and gag, pol and/or env genes) comprising a therapeutic gene(s) (e.g., GM-CSF, B7-2, etc.). Cells receiving all three DNA constructs will package and shed pseudotyped viral particles comprising RNA derived from the retroviral vector containing the therapeutic gene(s). In this manner, packaging cell lines are created in situ in the patient's tumor. Such an approach is superior to the injection of packaging cell lines into a patient. When packaging cell lines (typically mouse fibroblast cell lines shedding a replication defective virus) are injected into a patient, the patient's immune response is often directed against the foreign cellular proteins rather than against the desired target (the tumor cell). In contrast, the injection of DNA comprising the components of the packaging cell line, rather than the cell line itself, permits the immune response to be directed at the desired target.

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); $\mu$M (micromolar); mol (moles); mmol (millimoles); $\mu$mol (micromoles); nmol (nanomoles); g (gravity); gm (grams); mg (milligrams); $\mu$g (micrograms); pg (picograms); L (liters); ml (milliliters); $\mu$l (microliters); cm (centimeters); mm (millimeters); $\mu$m (micrometers); nm (nanometers); hr (hour); min (minute); msec (millisecond); ° C. (degrees Centigrade); AMP (adenosine 5'-monophosphate); cDNA (copy or complimentary DNA); DTT (dithiotheritol); ddH$_2$O (double distilled water); dNTP (deoxyribonucleotide triphosphate); rNTP (ribonucleotide triphosphate); ddNTP (dideoxyribonucleotide triphosphate); bp (base pair); kb (kilo base pair); TLC (thin layer chromatography); tRNA (transfer RNA); nt (nucleotide); VRC (vanadyl ribonucleoside complex); RNase (ribonuclease); DNase (deoxyribonuclease); poly A (polyriboadenylic acid); PBS (phosphate buffered saline); OD (optical density); HEPES (N-[2-Hydroxyethyl]piperazine-N-[2-ethanesulfonic acid]); HBS (HEPES buffered saline); SDS (sodium dodecyl sulfate); Tris-HCl (tris[Hydroxymethyl]aminomethane-hydrochloride); rpm (revolutions per minute); ligation buffer (50 mM Tris-HCl, 10 mM MgCl$_2$, 10 mM dithiothreitol, 25 $\mu$g/ml bovine serum albumin, and 26 $\mu$M NAD+, and pH 7.8); EGTA (ethylene glycol-bis($\beta$-aminoethyl ether) N, N, N', N'-tetraacetic acid); EDTA (ethylenediaminetetracetic acid); ELISA (enzyme linked immunosorbant assay); LB (Luria-Bertani broth: 10 g tryptone, 5 g yeast extract, and 10 g NaCl per liter, pH adjusted to 7.5 with 1N NaOH); superbroth (12 g tryptone, 24 g yeast extract, 5 g glycerol, 3.8 g KH$_2$PO$_4$ and 12.5 g, K$_2$HPO$_4$ per liter); DME or DMEM (Dulbecco's modified Eagle's medium); ABI (Applied Biosystems Inc., Foster City, Calif.); ATCC (American Type Culture Collection, Rockville, Md.); Beckman (Beckman Instruments Inc., Fullerton Calif.); Becton Dickinson (Becton Dickinson, San Jose, Calif.); BM (Boehringer Mannheim Biochemicals, Indianapolis, Ind.); Bio-101 (Bio-101, Vista, Calif.); BioRad (BioRad, Richmond, Calif.); Brinkmann (Brinkmann Instruments Inc. Wesbury, N.Y.); BRL, Gibco BRL and Life Technologies (Bethesda Research Laboratories, Life Technologies Inc., Gaithersburg, Md.); Caltag (Caltag Laboratories Inc., South San Francisco, Calif.); CRI (Collaborative Research Inc. Bedford, Mass.); Eppendorf (Eppendorf, Eppendorf North America, Inc., Madison, Wis.); Falcon (Becton Dickenson Labware, Lincoln Park, N.J.); Invitrogen (Invitrogen, San Diego, Calif.); New Brunswick (New Brunswick Scientific Co. Inc., Edison, N.J.); NEB or New England Biolabs (New England BioLabs Inc., Beverly, Mass.); Novagen (Novagen, Inc., Madision, Wis.); Pharmingen (PharMingen, San Deigo, Calif.); Pharmacia (Pharmacia LKB Gaithersburg, Md.); Promega (Promega Corporation, Madison, Wis.); R & D Systems (R & D Systems Inc., Minneapolis, Minn.); Sigma (Sigma Chemical Co., St. Louis, Mo.); and Stratagene (Stratagene Cloning Systems, La Jolla, Calif.).

Unless otherwise indicated, all restriction enzymes were obtained from New England Biolabs and used according to the manufacturers directions. Unless otherwise indicated, synthetic oligonucleotides were synthesized using an ABI DNA synthesizer, Model No. 391.

EXAMPLE 1

Construction Of Mono- and Bi-Cistronic Retroviral Vectors And Packaging Of Recombinant Virus Retroviral gene therapy vectors were constructed that contained the genes for GM-CSF, B7-2, GM-CSF and B7-2, or GFP gene as shown schematically in FIG. 1. FIG. 1 provides a schematic showing the map of the parental vector (pLSN), pLSNB70 (encodes human B7-2), pLSNGM1 (encodes human GM-CSF), pLSN-BG9 (encodes both B7-2 and GM-CSF) and pLSN-GFP (encodes GFP).

All genes were cloned into the polylinker region of the MLV-based pLSN plasmid [Robinson et al. (1995) Gene Therapy 2:269 and co-pending application Ser. No. 08/336, 132]. Therapeutic genes were inserted into pLSN such that their expression was under the control of the retroviral LTR (long terminal repeat) whereas a neomycin-resistance gene was under the control of an internal SV40 promotor. The vectors lacked the gag, pol, or env genes necessary for retroviral packaging in order to render them replication incompetent. These structural proteins were provided in trans by the retroviral packaging cell line PA317 [ATCC CRL 9078; Markowitz et al. (1988) J. Virol. 62:1120] or PG13 [ATCC CRL 10686; Miller et al. (1991) J. Virol. 65:2220]. For the bi-cistronic vector containing GM-CSF and B7-2 genes, the two genes were interposed with an internal ribosome entry site (IRES) derived from the Encephalomyocarditis Virus (EMCV) genome (pCITE-1, Novagen).

a) Construction Of pLSN pLSN is a derivation of pLNL6, a retroviral vector approved for clinical use in the United States of America. To construct pLSN an intermediate vector, pLLL, was first constructed.

pLLL was constructed using pLNL6 (SEQ ID NO: 1) as a starting point. pLNL6 contains the MoMuLV promoter in the 3' LTR and the murine sarcoma virus (MSV) promoter in the 5' LTR. For ease in subsequent cloning steps, the few cloning sites and the internal SV-neo gene present in pLNL6 were removed and replaced with a synthetic polylinker to generate pLLL.

To construct pLLL, pLNL6 was digested with ClaI and BclI and the vector fragment was gel purified using GeneClean (Bio-101) according to the manufacturer's instructions. A double-stranded insert containing the polylinker site was constructed using the following two oligonucleotides:
5'-GATCTAAGCTTGCGGCCGCAGATCT CGAGCCATGGATCCTAGGCCTGATCACGCGTCGAC TCGCGAT-3' (SEQ ID NO:2) and
5'-CGATCGCGAGTCGACGCGTGATCAGGCCTAGGA TCCATGGCTCG AGATCTGCGGCCGCAAGCTTA-3' (SEQ ID NO:3). These oligonucleotides were annealed, kinased and ligated to the gel purified pLNL6 vector fragment and the ligation mixture was used to transform competent DH5α cells (BRL). Proper construction of pLLL was confirmed by restriction enzyme digestion of plasmid DNA prepared from ampicillin-resistance bacterial colonies as well as by DNA sequencing near the site of insertion of the polylinker.

To generate a vector containing a selectable marker which allows for the isolation of cells which have incorporated the vector DNA, pLSN was created. pLSN contains the neo gene under the transcriptional control of the SV40 enhancer/promoter. To create pLSN, a BamHI/StuI fragment containing SV40 enhancer/promoter was isolated from pLNSX [Miller, A. D. and Rosman, G. J. (1989) BioTechniques 7:980]. pLNSX and pLLL were digested with BamHI and StuI and the digestion products were gel purified. A small fragment of approximately 350 bp which contained the SV40 promoter from pLNSX was cloned into the pLLL vector. The final product, designated pLLL/SV40, was confirmed by restriction enzyme digestion using BamHI and ClaI.

In order to insert a better translation initiation codon at the beginning of the neo gene, the neo gene was isolated from pLNSX using PCR. Pfu polymerase (Stratagene) was used to amplify the gene. This amplification was conducted in 5 μl of 10× Pfu reaction buffer, 0.5 μl of dNTP (15 mM), 0.5 mM of each of the following primers: 5'-AAGCTTGATCACCACCATGATTGAACAAGATGG-3' (SEQ ID NO:4) and 5'-CCGGATCCGTCGACCCCAGAGTCCCGCTC AGAAG-3' (SEQ ID NO:5), 0.5 μl of pLNSX (0.01 μg) and 38 μl of ddH$_2$O. These primers contain the modified translation initiation control sequence (-CCACC<u>ATG</u>-), as this modification was found to greatly increase the strength of the neo gene in tissue culture cells [Kozak, M. (1986) Cell 44:283].

The mixture was heated at 95° C. for 5 min and 1 μl of Pfu polymerase was added. This reaction mixture was cycled through 30 cycles at 94° C. for 1 min, 55° C. for 1 min, and 72° C. for 3 min. After amplification, the DNA comprising the neo gene was gel purified and ligated with the BclI-digested pLLL/SV40 vector to create pLSN. Confirmation of proper construction was made by restriction enzyme digestion as well as DNA sequencing.

b) Cloning Of The Human B7-2 And GM-CSF cDNAs

GM-CSF and B7-2 cDNAs were amplified from normal human lymphocyte RNA by RT-PCR as follows. In each case, the oligonucleotides used for PCR amplification comprised an optimized eukaryotic initiation sequence. For amplification of the GM-CSF cDNA, the following primer pair was used: 5' primer: 5'-CCCGGG AAGCTT CCACCATGTGGCTGCAGAGCCTG-3' (SEQ ID NO:6) and 3' primer: 5'-AATGGATCCTATCACTCCTGGACTGGCTC-3' (SEQ ID NO:7). The sequence of the human GM-CSF cDNA is available in GenBank accession no. M11220 and in SEQ ID NO:8. For amplification of the B7-2 cDNA, the following primer pair was used: 5' primer: 5'-TGTGGAT CCACCATGGGACTGAGTAACATT-3' (SEQ ID NO:9) and 3' primer: 5'-TTTGGATCCTTAAAAACATGTATCACTTTT GTCGC-3' (SEQ ID NO:10). The sequence of the human B7-2 cDNA is available in GenBank accession no. U04343 and in SEQ ID NO:11. RT-PCR was carried out using an RT-PCR kit (BRL and Promega) according to the manufacturer's instructions.

The PCR amplified B7-2 gene was cloned directly (i.e., blunt-end ligation) into HincII digested pT7T318U (Pharmacia) to generate pT7T318U-B7-2. The PCR amplified GM-CSF gene was digested with HindIII and BamHI and cloned into HindIII and BamHI digested pBluescript KS (−) (Stratagene) to generate pBS-GM-CSF. Proper amplification and cloning of the B7-2 and GM-CSF open reading frames was confirmed by partial DNA sequencing and by restriction enzyme digestion.

c) Construction Of Retroviral Vectors Containing B7-2, GM-CSF And GFP Genes

The B7-2 and GM-CSF cDNAs were subcloned into the retroviral vector pLSN to generate pLSNB70 and pLSNGM1, respectively. To generate pLSNB70, pT7T318U-B7-2 was digested with BamHI and the B7-2 fragment was gel purified and cloned into BglII-digested pLSN. To generate pLSNGM1, pBS-GM-CSF was digested with HindIII and BamHI and the GM-CSF fragment was gel purified and cloned into HindIII- and BamHI-digested pLSN.

In addition, cDNA for the reporter gene green fluorescent protein (GFP) was also inserted into the retroviral vector pLSN to generate pLSN-GFP. The GFP gene was PCR amplified using Pfu polymerase (Stratagene) from pGFP (Clontech) using the following primer pair: 5' primer: 5'-AAAAGCTTGGATCCACCATGAGTAAA GGA-3' (SEQ ID NO:12) and 3' primer: 5'-AATCTAGATTACTATTTGTATAGTT CATCC-3' (SEQ ID NO:13). The PCR amplified GFP gene was cloned directly into EcoRV-digested pBluescript KS(-) to generate pBS-GFP#1. pBS-GFP#1 was digested with NotI and XhoI and the GFP fragment was gel purified and inserted into NotI- and XhoI-digested pLSN to generate pLSN-GFP.

Each of the resulting vectors contained a neomycin resistance gene driven by an internal SV40 promoter.

d) Construction Of A Bi-Cistronic Retroviral Vector Encoding B7-2 And GM-CSF

A bi-cistronic retroviral vector, pLSN-BG9, containing the B7-2 and GM-CSF genes separated by an IRES was constructed as follows. The following three DNA fragments were gel purified: the EMCV IRES from XhoI- and HindIII-digested pGEM-IRES8 (described below); the GM-CSF gene from HindIII- and BamHI-digested PCR product (section b); and the B7-2 gene from NotI- and XhoI-digested pLSNB70. The three purified fragments were mixed together and ligated into NotI- and BamHI-digested pLSN to generate pLSN-BG9.

pGEM-IRES8 was constructed by isolating the EMCV IRES fragment from EcoRI- and MscI-digested pCITE-1 (Novagen) and inserting this fragment into EcoRI- and SmaI-digested pGEM-7Zf+ (Promega).

e) Generation Of Recombinant Retrovirus

Retroviral plasmid DNA was transfected into the packaging cell line PA317 [Miller, A. D. and Buttimore, C. (1986) Mol. Cell. Biol. 6:2895 and Miller, A. D. (1990) Hum. Gene Ther. 1:5] by lipofection as described (Robinson et al., supra). Briefly, PA317 cells were transfected with pLSNGM1, pLSNB70, pLSN-BG9, or pLSN-GFP using lipofectamine (Gibco/BRL). Lipofection was carried out according to the manufacturer's protocol.

PA317 cells were grown in DMEM containing 10% FBS and penicillin and streptomycin in an atmosphere containing 10% $CO_2$ at 37° C. Twenty hours prior to lipofection, PA317 cells were placed into a T25 flask (Falcon) at 50% confluency (approximately $1 \times 10^6$ cells/flask). To transfect the cells, DNA (4 µg) was added to 300 µl serum-free DMEM lacking antibiotics in a microcentrifuge tube (Eppendorf), and mixed gently. In a 15 ml polycarbonate tube (Falcon), 300 µl serum-free DMEM and 12 µl of lipofectamine were mixed gently. The two solutions were combined by adding the DNA-containing solution dropwise into the lipofectamine tube, and the mixture was incubated at RT for 45 min. Following this incubation, 2 ml of serum-free DMEM was added and mixed gently. The cells were washed with serum-free DMEM and the DNA/lipofectamine mixture was gently added to the cells. The cells were incubated at 37° C. in a 10% $CO_2$ incubator for 5 hr. After the 5 hr incubation, 2.5 ml of DMEM containing 20% FBS and antibiotics was added to the T25 flask and the cells were incubated overnight. Twenty hours after the 5 hr incubation, the medium was replaced with fresh DMEM containing 20% FBS and antibiotics. For vector titration, the medium was changed at 24 hr after the medium was replaced with fresh DMEM and virus was harvested 24 hr later. When cells were to be cloned (i.e., for the production of stable producer cell lines), the transfected PA317 cells were split at a 1:10 ratio into selective medium (i.e., DMEM containing 500 µg/ml G418 and 10% FBS).

Replication incompetent virus was harvested from supernatant of the transfected PA317 cultures 48 hrs after transfection of the PA317 cells and immediately frozen at −80° C. for later use.

EXAMPLE 2

Expression Of B7-2 And GM-CSF In The Human Glioblastoma Cell Line D54MG

Viral particles containing recombinant retroviral genomes encoding either GM-CSF, B7-2, B7-2/GM-CSF or GFP were used to transduce the human glioblastoma cell line D54MG.

a) Growth Of D54MG In Tissue Culture

The human glioblastoma cell line D54MG [obtained from Dr. D. Bigner, Duke University, Durham, N.C.; Bigner et al. (1981) J. Neuropathol. Exp. Neurol. 40:201] was cultured in Dulbucco's Modified Eagle's Media (DMEM) with 10% fetal bovine serum (Gibco), 0.2 units/ml penicillin-streptomycin solution (Sigma), and 0.2 mM glutamate at 37° C. in a humidified atmosphere containing 5% $CO_2$.

b) Retroviral Transduction

Frozen virus stock was thawed at 37° C. Polybrene was added to the thawed virus solution at a final concentration of 4 µg/ml. Culture media was added to the virus solution to bring the final volume to 1.5 ml. D54MG cells in logarithmic growth phase in T25 flasks (approximately $1 \times 10^6$ cells) were incubated in the virus supernatant at 37° C., 5% $CO_2$ for 3 hours. The same volume of media and polybrene without virus was used as control. After 3 hours, a further 3 ml of culture media was added to each flask and they were incubated overnight. Media was changed the next morning.

c) Selection Of Transduced Cells

Twenty-four hours after retroviral transduction, 500 µg/ml of the neomycin analog G418 was added to the culture media. Media was changed every two to three days until complete selection had taken place (i.e., all cells in the control flasks were dead). After selection, the cells were cultured in growth media containing reduced concentrations of G418 (250 µg/ml) and allowed to grow to confluence.

d) Analysis Of B7-2 Expression By Flow Cytometry

Transduced D54MG cells at approximately 70% confluence were harvested by scraping after room temperature incubation for 15 minutes in 0.02% EDTA in Phosphate-Buffered Saline (PBS). In aliquots of $10^6$ cells per 200 µl of immunofluorescence (IF) buffer (2% fetal calf serum, 0.02% sodium azide in PBS), samples were incubated on ice for 1 hour with 1 µg of RPE-conjugated monoclonal anti-human B7-2 antibody (Ancell) or 1 µg of RPE-conjugated isotype-control murine $IgG_1$ antibody (Pharmingen). Cells were washed four times in IF buffer, and fixed in 1% formalin in PBS. Samples were then read on a cytometer (B-D Flow Cytometer) using standard techniques.

e) Analysis Of GM-CSF Expression By ELISA

Transduced D54MG cells at approximately 70% confluence in T75 flasks were incubated in fresh media for 24 hours. After this period of incubation, media was harvested and centrifuged briefly to remove cells and debris. The cell number per flask was determined. GM-CSF levels in the harvested media was tested using a commercially available kit (Quantikine, R & D Systems) as per the manufacturer's instructions. The level of GM-CSF was converted to $\mu g/10^6$ cells/24 hours based on the cell number in the flasks from which the media originated.

f) Expression Of B7-2 And GM-CSF In D54MG Cells

Flow cytometry studies showed that B7-2 was expressed on the surface of B7-2- and B7-2/GM-CSF-transduced D54MG cells but not on wild type or GM-CSF-transduced cells (1–2 orders of magnitude fluorescence shift compared to isotype controls). Flow cytometry of GFP-transduced D54MG cells without staining revealed mildly increased autofluorescence compared to wild type D54MG. Representative flow cytometry histograms are shown in FIGS. 2A–E.

FIGS. 2A–E provide flow cytometry histograms for: wild type D54MG (2A), B7-2-transduced D54MG (2B), GM-CSF-transduced D54MG (2C), B7-2 and GM-CSF-transduced D54MG (2D), and GFP-transduced D54MG (2E). For FIGS. 2A–2D, the histograms on the left represent D54MG cells stained with isotype matched control antibodies while the histograms on the right represent staining with monoclonal anti-human B7-2 antibodies. For FIG. 2E, the histogram on the left represents unstained wild type D54MG cells while the histogram on the right represents unstained GFP-transduced D54MG.

GM-CSF production was significant for GM-CSF-transduced (30 ng/$10^6$ cells/day) and B7-2/GM-CSF-transduced (5 ng/$10^6$ cells/day) cells but not for wild type or B7-2-transduced cells. Gene expression in the transduced D54MG cells is summarized in Table 1.

TABLE 1

Therapeutic Gene Expression In Vitro In Wild Type And Transduced D54MG By ELISA (GM-CSF) Or Flow Cytometry (B7-2)

| Cell Line | Vector (Genes Transferred) | GM-CSF Production (ng/$10^6$ Cells/Day) | B7-2 Expression (Orders Of Magnitude Fluorescence Shift) |
|---|---|---|---|
| D54MG | None | 0.0 | 0 |
| D54MG | pLSNB70 (B7-2) | 0.0 | 2 |
| D54MG | pLSNGM1 (GM-CSF) | 30.0 | 0 |
| D54MG | pLSNBG9 (B7-2 and GM-CSF) | 5.0 | 1 |

The above results demonstrate that therapeutic gene expression in the D54MG human glioblastoma cell line was high after in vitro transduction with the pLSN-based retroviral vectors. Levels of GM-CSF production were comparable to those reported in other retrovirally transduced tumor cell lines [Dranoff et al. (1993) Proc. Natl. Acad. Sci. USA 90:3539 and Jaffee et al. (1993) Cancer Res. 53:2221].

Quantification of B7-2 expression is difficult using flow cytometry as expression is essentially a binary system (either present or absent on the cell surface). However, B7-2 molecules were clearly present on the surface of D54MG cells transduced with retroviral vectors containing the B7-2 gene and absent on wild type or GM-CSF-transduced cells. These results demonstrate that the above-described retroviral vectors provide simple, reliable tools for transferring GM-CSF and/or B7-2 genes into human glioblastoma cells in vitro.

EXAMPLE 3

Tumor Growth Efficiency And Human PBL Reconstitution In SCID/beige And SCID/nod Mice This example describes the reconstitution of SCID/nod and SCID/beige mice with human PBL and the engraftment of human tumor cells in these mouse strains.

a) Animals And Human PBL Reconstitution

For most experiments, four to five week old female C.B-17-SCID-beige mice were purchased from Taconic (Germantown, N.Y.). For the first vaccination/challenge experiment, four to five week old female SCID/nod mice were obtained from Dr. L. Pilarski (Cross Cancer Institute, University of Alberta, Edmonton, Alberta). The mice were maintained in filtered cages in a virus free environment and received cotrimoxazole in their drinking water twice per week.

Hu-PBL-SCID mouse reconstitution was carried out as previously described [Zhang et al. (1996) Proc. Natl. Acad. Sci. USA 93:14720]. Briefly, each mouse was intraperitoneally (IP) injected with $2-3\times10^7$ PBLs resuspended in 0.5 ml of Hanks' balanced salt solution. A near 100% success rate in reconstitution of SCID/bg mice was obtained when fresh PBLs were used. Five days to three weeks after reconstitution, mice were bled from the tail and the human Ig level was assessed by enzyme-linked immunosorbent assay (ELISA) using a monoclonal rabbit anti-human IgG/IgM antibody (Jackson Labs) and control human IgG (Sigma).

Preliminary results indicated that SCID/nod mice were not as reliably reconstituted with human peripheral blood lymphocytes as were SCID/bg mice. Unlike SCID/bg mice, reconstitution of SCID/nod mice with human PBLs appeared to vary both from PBL donor to PBL donor and from mouse to mouse. Furthermore, many hu-PBL-SCID/nod mice developed a disease characterized by cachexia, alopecia, and facial edema 3 to 6 weeks after reconstitution. This was not seen in unreconstituted SCID/nod mice or in SCID/bg mice with or without reconstitution. The etiology was unclear, though the possibilities of Graft vs. Host Disease and diabetes melitis were considered. Because of these difficulties, reconstituted SCID/bg mice are preferred for tumor growth and vaccination/challenge experiments.

b) Subcutaneous Tumor Growth Experiments

Five to seven week old SCID/bg mice were injected subcutaneously (SC) on the right flank with $2\times10^6$ retrovirally-transduced and selected D54MG cells. Control mice were injected SC on the right flank with wild type D54MG cells. Six days post injection, mice were reconstituted via IP injection as described above with $2\times10^7$ human peripheral blood lymphocytes isolated on a Histopaque gradient (Sigma) from the buffy coat layer of whole blood from healthy donors. Reconstitution was monitored by examination of sera (tail bleeds) for the presence of human Ig by ELISA. In all but one experiment, half of the mice from each group (transduced and untransduced) were left unreconstituted as controls. Tumor size was measured in three directions by calipers every 3 to 5 days. Comparison was made between transduced and untransduced tumor cells and between reconstituted and unreconstituted mice.

c) Statistical Analysis

Comparison between tumor sizes in different groups was performed using standard one-way analysis of variance (ANOVA).

d) Tumor Growth And Human PBL Reconstitution In SCID/beige And SCID/nod Mice

As described below, SCID/bg mice receiving human PBL via IP injection supported the growth of a human melanoma cell line with nearly 100% success and these animals demonstrated significant levels of human lymphocytes by flow cytometric analysis in spleen and peripheral blood 38 days post reconstitution. This example shows that both SCID/nod and SCID/bg mice supported the growth of wild type D54MG cells (human glioblastoma) subcutaneously with 100% efficiency (35/35) regardless of human lymphocyte reconstitution. D54MG tumors transduced with B7-2, GM-CSF, or both B7-2 and GM-CSF also grew with 100% efficiency in unreconstituted SCID/bg mice (4/4, 8/8, and 4/4 respectively). Growth of D54MG tumors transduced with B7-2 and GM-CSF was inhibited in human lymphocyte-reconstituted mice as detailed below.

Reconstitution with human PBLs was monitored by ELISA for the presence of human Ig using sera collected from the tail of the reconstituted mice. All SCID/bg mice receiving human PBLs (46/46) had significant levels (>100 µg/ml) of human Ig in serum within 14 days of reconstitution. However, 3 of 12 SCID/nod mice that received human PBLs failed to demonstrate human Ig on serial testing and were excluded from the study. Subsequent studies with SCID/nod mice revealed that the success of human PBL reconstitution also varied significantly from PBL donor to PBL donor. For these reasons, SCID/bg mice (not SCID/nod) were preferred for tumor growth and vaccination/challenge experiments.

EXAMPLE 4

Growth Suppression Of B7-2 And GM-CSF-Transduced D54MG But Not Wild Type D54MG In Hu-PBL-SCID/bg Mice In two separate experiments, growth of D54MG transduced with B7-2 in human PBL reconstituted SCID/bg mice was markedly inhibited compared to untransduced and/or unreconstituted controls. These results are summarized in FIGS. 3A and 3B.

Figure 3A:
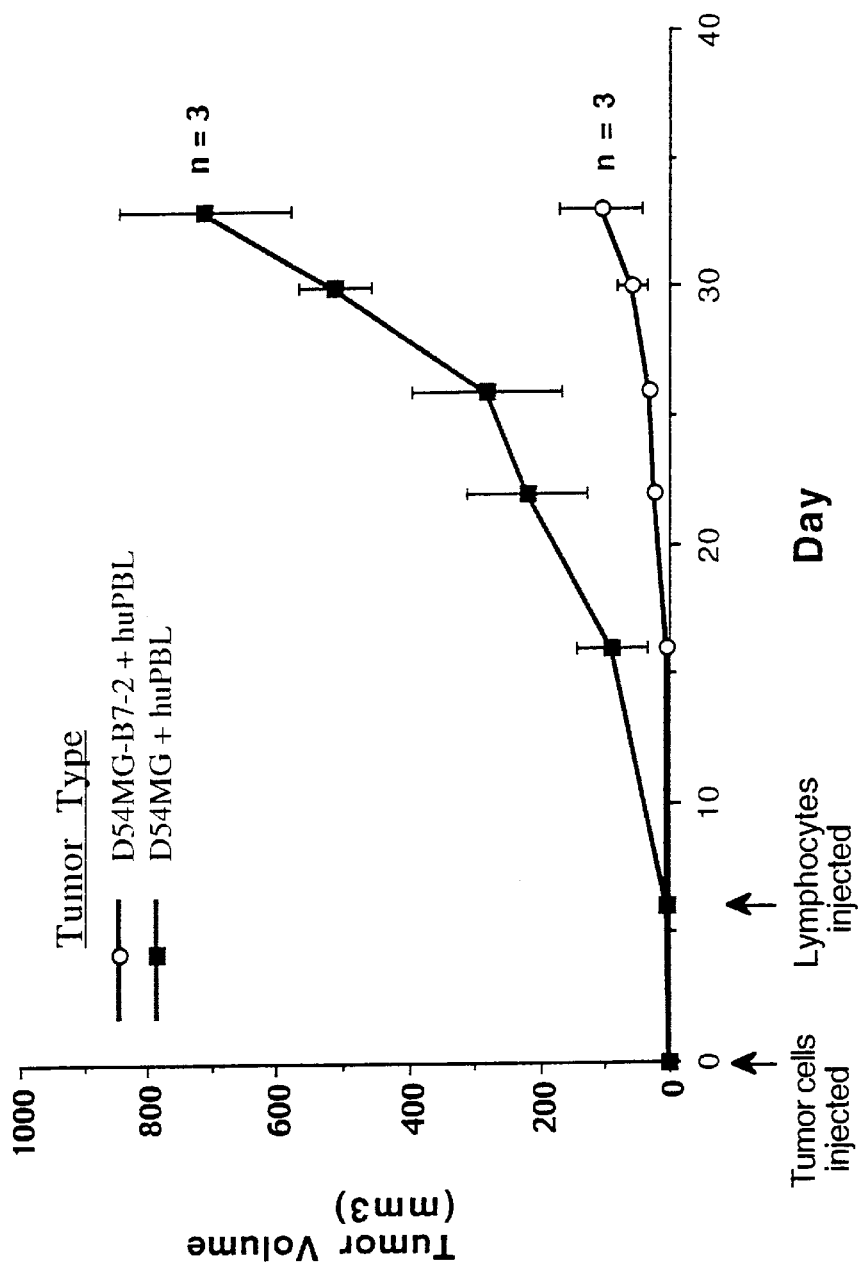
FIGS. 3A and 3B show the inhibition of growth of B7-2-transduced D54MG cells compared to unmodified D54MG cells in Hu-PBL-SCID/bg mice.
Figure 3B:
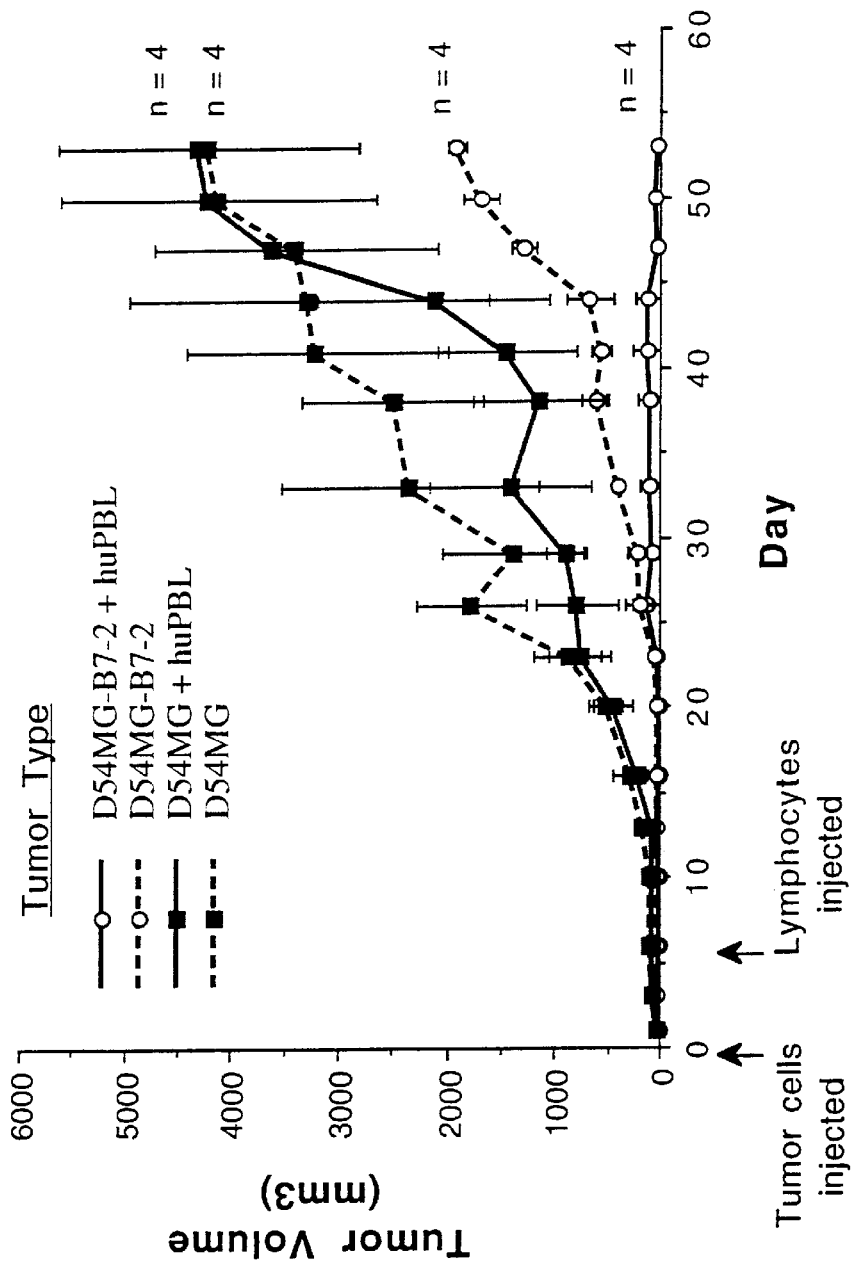

For the results shown in FIG. 3, all mice received $2 \times 10^6$ tumor cells (either D54MG or D54MG-B7-2) subcutaneously on the right flank on Day 0. Mice were injected IP with $2 \times 10^7$ human PBL six days after tumor cell injection. Reconstitution was confirmed by detection of serum human Ig levels >100 µg/ml. In the first experiment (3A), all mice were reconstituted with human PBLs. In FIG. 3A, tumor volume ($mm^3$) is plotted over time (days) for mice receiving untransduced D54MG cells (open circles; "D54MG") and D54MG cells transduced with pLSNB70 (solid squares; "D54MG-B7-2"). In the second experiment (3B), half the mice from both groups (D54MG and D54MG-B7-2) were left unreconstituted (hatched lines). In FIG. 3B, tumor volume ($mm^3$) is plotted over time (days) for mice receiving untransduced D54MG cells (solid squares) and D54MG cells transduced with pLSNB70 (open triangles). In FIG. 3, arrows are used to indicate the times at which the tumor cells and lymphocytes were injected.

A standard test for statistical significance in subcutaneous tumor growth models is comparison of tumor volumes by ANOVA at a point approximately two-thirds along the growth curve [Gallagher et al. (1993) Tumor Immunology: A Practical Approach, IRL Press, Oxford, UK]. By this criteria, the mean tumor volume for B7-2-transduced tumors in human lymphocyte-reconstituted mice was significantly less than the mean tumor volume for wild type (i.e., non-transduced) tumors by 22 days in the first experiment and by 35 days in the second experiment (p<0.05 in both). Interestingly, growth of D54MG-B7-2 tumors in unreconstituted mice was also mildly inhibited compared to wild type tumors (FIG. 3B). However, growth inhibition was much more marked in the reconstituted mice. These results suggests that, although a small portion of the growth inhibition seen for D54MG-B7-2 may be human lymphocyte-independent, the predominant effect is dependent on human lymphocytes.

Growth of GM-CSF-transduced D54MG in human lymphocyte reconstituted mice was moderately inhibited compared to untransduced and/or unreconstituted controls in two separate experiments. These results are summarized in FIGS. 4A and 4B.

Figure 4A:
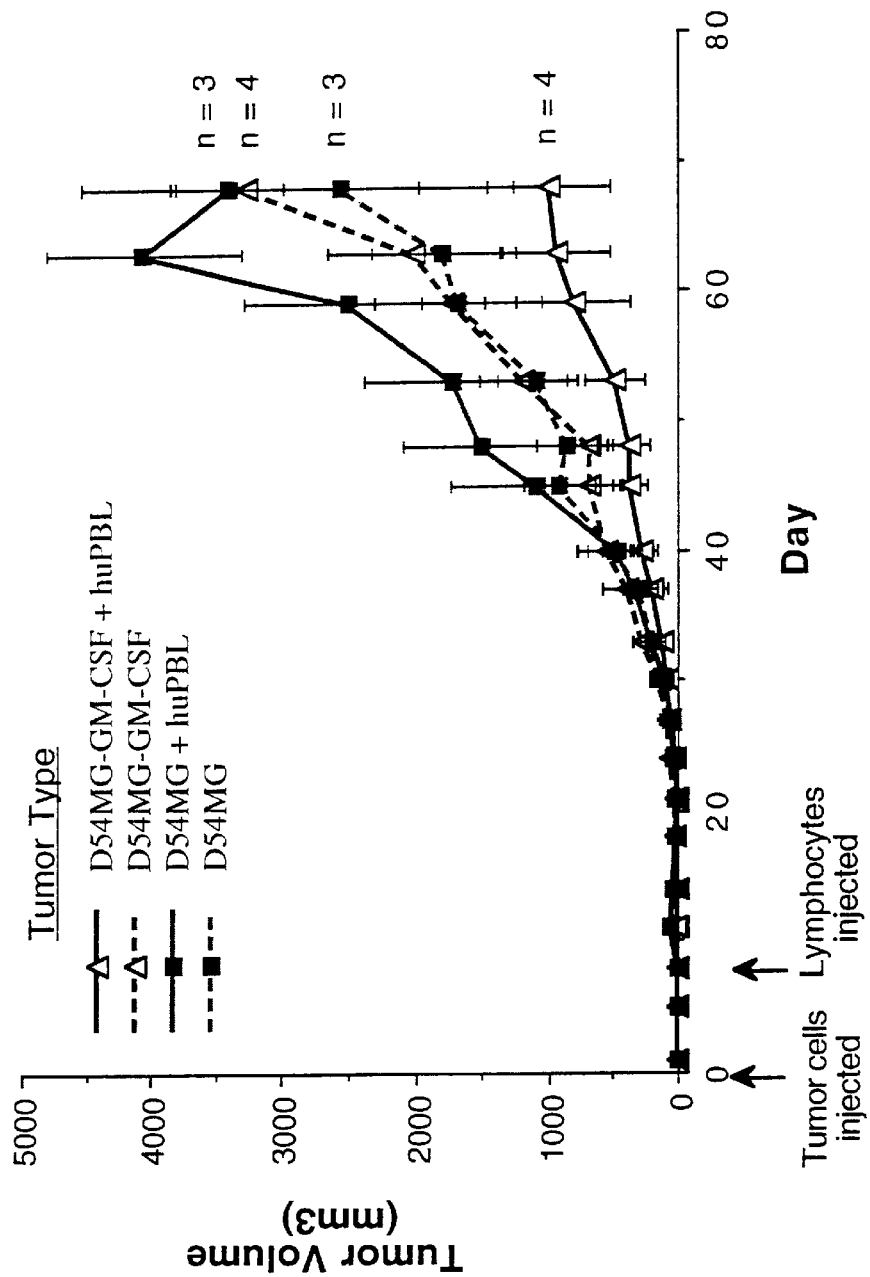
FIGS. 4A and 4B show the inhibition of growth of GM-CSF-transduced D54MG cells compared to unmodified D54MG cells in Hu-PBL-SCID/bg mice.
Figure 4B:
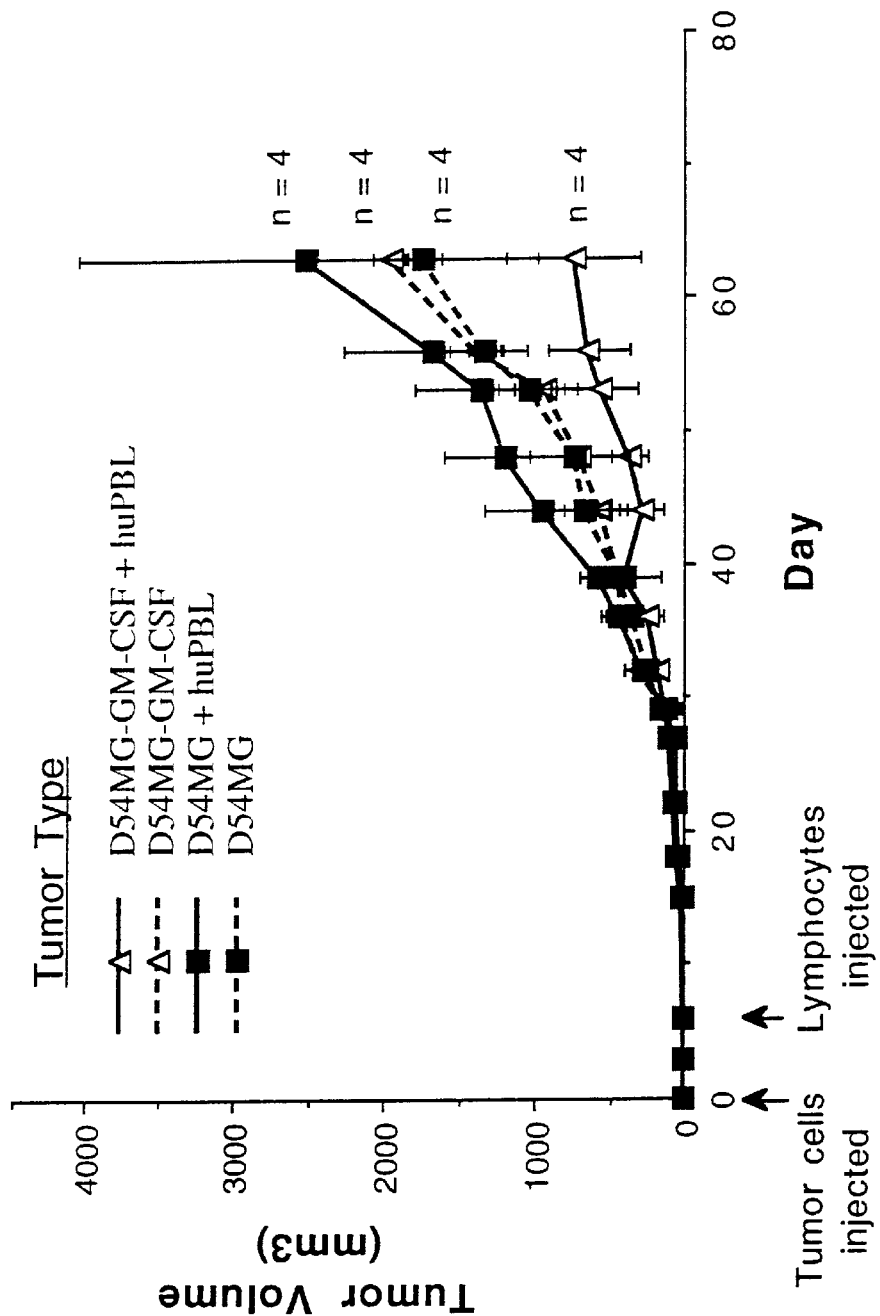

For the results shown in FIG. 4, all mice received $2 \times 10^6$ tumor cells (either D54MG or D54MG-GM-CSF) subcutaneously on the right flank on Day 0. Mice were injected IP with $2 \times 10^7$ human PBL six days after tumor cell injection. Reconstitution was confirmed by detection of serum human Ig levels >100 µg/ml in ELISAs. In both experiments shown in FIGS. 4A and 4B, half the mice from both groups (D54MG and D54MG-GM-CSF) were left unreconstituted (hatched lines). In FIG. 4A, tumor volume ($mm^3$) is plotted over time (days) for mice receiving untransduced D54MG cells (solid squares; "D54MG") and DM54MG cells transduced with pLSNGM1 (open triangles; "D54MG-GM-CSF"). In FIG. 4B, tumor volume ($mm^3$) is plotted over time (days) for mice receiving untransduced D54MG cells (solid squares) and D54MG cells transduced with pLSNGM1 (open triangles). In FIG. 4, arrows are used to indicate the times at which the tumor cells and lymphocytes were injected.

Neither of the experiments shown in FIGS. 4A and 4B achieved statistical significance by ANOVA on their own. However, when the results from the two experiments were pooled, GM-CSF-transduced tumors in human PBL-reconstituted mice were significantly smaller than wild type by 55 days (p<0.001). No inhibition of D54MG-GM-CSF tumor growth was observed in unreconstituted mice.

These results demonstrate that transduction of D54MG tumor cells with recombinant retroviral vectors encoding either B7-2 or GM-CSF resulted in an inhibition of tumor growth in human PBL-reconstituted SCID/bg mice (FIGS. 3 and 4). This demonstrates that the expression of either the human B7-2 gene or the human GM-CSF gene in glioblastoma cells overcomes local immunosuppression and results in a significant antitumor response. As demonstrated in the example below, the expression of both human B7-2 and GM-CSF genes in glioblastoma cells induces a systemic immune response that inhibits tumor growth at distant sites.

EXAMPLE 5

Efficacy Of Immunization Of Hu-PBL-SCID/nod And Hu-PBL-SCID/bg Mice With Therapeutic Gene-Modified D54MG Tumor Cells The ability to inhibit tumor growth in human PBL-reconstituted SCID mice by vaccination of the reconstituted mice prior to challenge with tumor cells was examined.

a) Vaccination/Challenge Experiments

In the first vaccination/challenge experiment, five to six week old female SCID/nod mice were reconstituted with $2 \times 10^7$ PBL from healthy donors via IP injection. Reconstitution was monitored by examination of sera (tail bleeds) for the presence of human Ig by ELISA. Five days after reconstitution, mice were vaccinated via IP injection of $1 \times 10^5$ irradiated (20,000 rad) D54MG cells (either wild type, GFP-transduced, or B7-2 and GM-CSF-transduced). Five days post-vaccination, all mice received SC injections of 1×10⁶ unirradiated wild type D54MG cells on the right flank. Tumor growth was measured as described above.

Figure 5A:
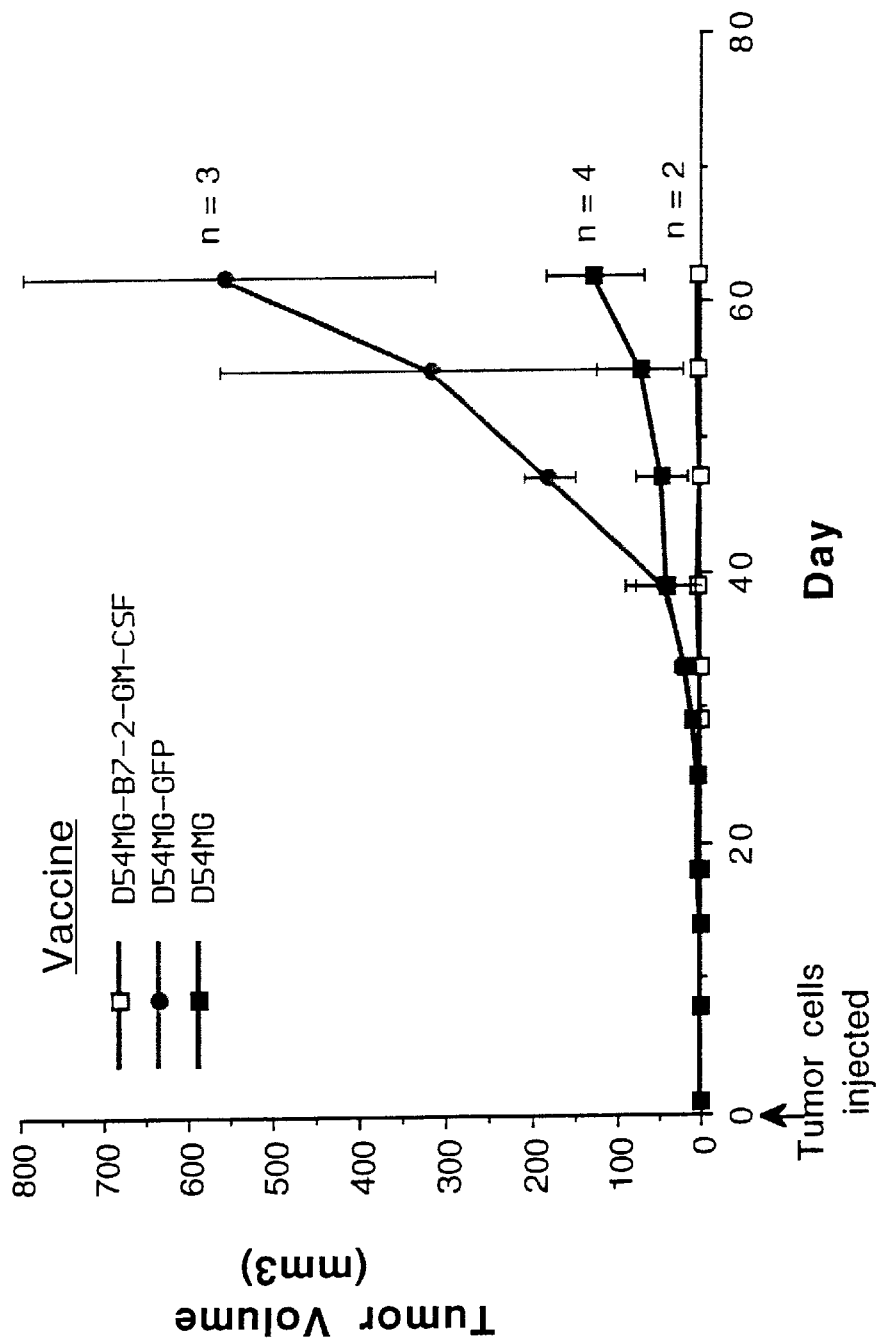
FIGS. 5A and 5B show the inhibition of unmodified D54MG cell challenges in Hu-PBL-SCID/nod mice (5A) and Hu-PBL-SCID/bg mice (5B) vaccinated with irradiated D54MG-B7-2/GM-CSF cells.

The second vaccination experiment was performed similarly, but in this instance, SCID/bg mice (Taconic) were used. In addition, the order of injections was slightly different. These mice first received SC injections of $1 \times 10^6$ wild type D54MG cells on their right flanks. Ten days later, they were reconstituted with $2 \times 10^7$ human PBL. Ten days after reconstitution, the mice were vaccinated with $1 \times 10^5$ irradiated tumor cells (either wild type, GFP-transduced, or B7-2/GM-CSF-transduced).

b) Vaccination Of Hu-PBL-SCID/bg Mice With D54MG Cells Expressing Therapeutic Genes Induces A Systemic Immune Response SCID/nod and SCID/bg mice were reconstituted, vaccinated and challenged with wild type D54MG cells as described above. As shown in FIG. 5A, growth of wild type D54MG tumors in human PBL-reconstituted SCID/nod mice which had been vaccinated with irradiated B7-2/GM-CSF-transduced D54MG was markedly inhibited compared to mice vaccinated with wild type or GFP-transduced D54MG. In FIG. 5A, tumor volume (mm³) is plotted over time (days) for mice vaccinated with either D54 cells transduced with pLSN-BG9 (open squares; "D54MG-B7-2-GM-CSF"), D54MG cells transduced with pLSN-GFP (solid circles; D54MG-GFP") or untransduced D54MG cells (solid squares; "DM54MG"). In FIG. 5A, an arrow indicates the time at which the tumor cells were injected.

While the results shown in FIG. 5A demonstrate that the growth of wild type D54MG tumors was inhibited in Hu PBL-SCID/nod mice vaccinated with irradiated B7-2/GM-CSF-transduced D54MG cells. However, small sample sizes due to the exclusion of several unsuccessfully reconstituted mice (3/12) prevented this effect from reaching statistical significance. This problem was subsequently overcome by performing all remaining studies with reconstituted SCID/bg mice.

Figure 5B:
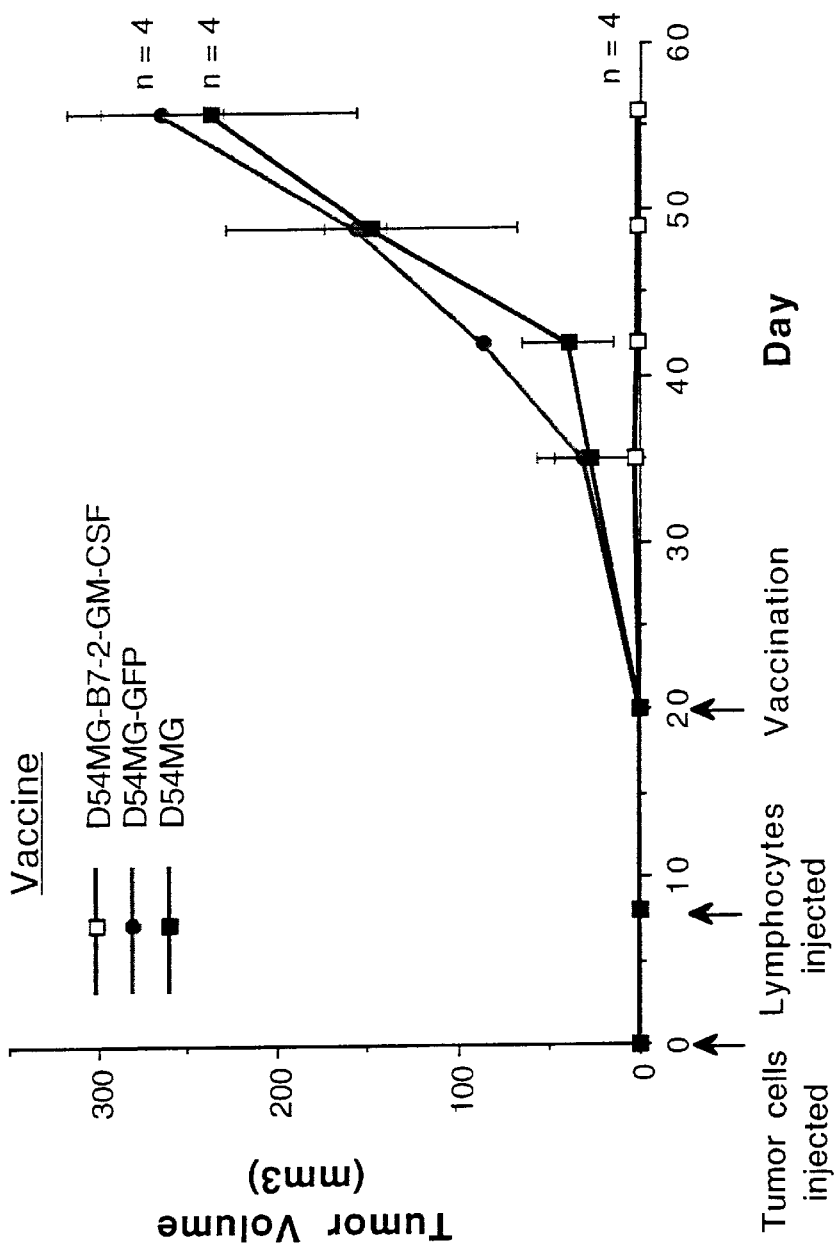

In a second vaccination experiment, wild type growth inhibition was seen in human PBL-reconstituted SCID/bg mice vaccinated with irradiated D54MG-B7-2/GM-CSF cells but not in mice vaccinated with either wild type D54MG or D54MG-GFP cells. In this second vaccination experiment all mice were successfully reconstituted with human PBLs as judged by ELISA (human Ig >100 μg/ml). The results are summarized in FIG. 5B. In FIG. 5B, tumor volume (mm³) is plotted over time (days) for mice vaccinated with either D54 cells transduced with pLSN-BG9 (open squares; "D54MG-B7-2-GM-CSF"), D54MG cells transduced with pLSN-GFP (solid circles; D54MG-GFP") or untransduced D54MG cells (solid squares; "DM54MG"). In FIG. 5B, arrows are used to indicate the times at which the tumor cells and lymphocytes were injected as well as the time at which the vaccination was given.

Unlike the first vaccination study (FIG. 5A), in the second vaccination study wild type D54MG cells were injected subcutaneously into the flank 20 days prior to vaccination. At the time of vaccination, tumors were palpable (1–2 mm³) on all mice. After vaccination, tumor growth continued exponentially in mice vaccinated with wild type or GFP-transduced D54MG. However, in mice vaccinated with GM-CSF/B7-2 transduced D54MG, tumor size increased slightly after vaccination (peaking at a mean of 8 mm³) and then regressed. Differences between the experimental and control groups achieved statistical significance by ANOVA (p<0.001) by day 42.

The above results demonstrate the inhibition of wild type tumor challenge growth in mice vaccinated with irradiated tumor cells transduced with retroviral vectors containing the B7-2 and GM-CSF genes and demonstrates that expression of these genes by glioblastoma cells induces a systemic immune response that inhibits tumor growth at distant sites.

It should also be noted that the present model, while an allogeneic system, has more similarities to autologous systems than may be immediately apparent. Unlike the classical immune-mediated rejection seen in allogeneic organ transplantation, this system is free of graft-origin "passenger lymphocytes." These lymphocytes are important in initiating allogeneic organ rejection responses by presenting antigen to host lymphocytes in the context of allogeneic Class II major histocompatibility complex (MHC) [Larsen et al. (1990) Annals of Surgery 212:308; Chandler and Passaro (1993) Archives of Surgery 128:279; Moller (1995) Transplantation Proc. 27:24]. The D54MG cell line expresses only Class I MHC and not Class II MHC in vitro. Although allogeneic Class I MHC molecules are expressed by the D54MG cells in this model, the absence of graft-origin Class II MHC-positive cells in the tumor renders this model more like an autologous system.

The use of the hu-PBL-SCID mouse model and a human glioblastoma tumor cell line has demonstrated the therapeutic utility and feasibility of in vivo immunogene therapy using GM-CSF or B7-2 genes (alone or in combination). The hu-PBL-SCID model provides a simple and powerful method to analyze human lymphocyte responses to human tumors in vivo. Early cancer immunotherapy studies using hu-PBL-SCID mice were limited by the influence of residual murine NK lymphocyte activity [Reddy et al. (1987) Cancer Res. 47:2456; Hill et al. (1991) FASEB J. 5:A965; Mueller et al. (1991) Cancer Res. 51:2193; Zhai et al. (1992) Cancer Immunol. Immunother. 35:237]. This problem has been overcome by the use of the SCID/bg and the SCID/nod mouse strains that are deficient in NK cells [Croy and Chapeau (1990) J. Reprod. Fert. 88:231; MacDougal et al. (1990) Cell. Immunol. 130:106; Prochazka et al. (1992) Proc. Natl. Acad. Sci. USA 89:3290; Mosier et al. (1993) J. Exp. Med. 177:191; Malkovska et al. (1994) Clin. Exp. Immunol. 96:158].

In conclusion, the retroviral gene therapy vectors provided herein demonstrated efficient bi-cistronic gene transfer (B7-2 and GM-CSF) to human glioblastoma cells in vitro. In an in vivo allogeneic human tumor/lymphocyte system, glioblastoma cells that express these genes result in lymphocyte-mediated responses that inhibit tumor growth locally and at distant sites. These results demonstrate the feasibility of immunogene therapy for glioblastoma multiforme using B7-2 and GM-CSF genes.

EXAMPLE 6

Transduction And Expression Of The B7-2 Gene In Established Tumor Cell Lines

To determine whether most of the human tumor cells are susceptible to retroviral transduction, and whether the T-cell costimulator gene B7-2 can be expressed in different tumors, a series of different types of human tumors were transduced with the B7-2 vector. Conditions for transduction were as described in Ex. 2. Twenty-four hrs after transduction, the cells were cultured in media containing different concentrations of G418. Results of this study are shown in Table 2.

TABLE 2

Transduction Of Tumor Cell Lines With pLSNB70

| Cell Type | Medium | Transduction Rate* / μg/ml (G418) |
|---|---|---|
| HeLa cervical epithelial carcinoma | DMEM | +++ / 500–1000 |
| SW480 colon adeno-carcinoma | DMEM or L15 | +++++ / 750–1000 |
| HT-29 colon adeno-carcinoma | McCoy's | +++++ / 500 |
| U87 MG/Glioblastoma-Astrocytoma | MEM+NaPy+NEa.a. or DMEM | +++++ / 1000 |
| SK-N-MC neuroblastoma | MEM++NaPy+NEa.a | +++ / 600 |
| SK-N-SH / neuro-blastoma | <MEM+NaPy+NEa.a. | ++ |
| A-431 epidermoid carcinoma | DMEM | ++ / 250 |
| RD embryonal rhabdomyosarcoma | MEM | +++ / 250 |
| HepG2 hepatoma | DMEM | +++++ / 750–1000 |
| Huh7 hepatoma | DMEM | ++ / 500–750 |
| PC3 prostate tumor | F12/DMEM | − / 250 no survivors |
| DU145 prostate tumor | MEM | ++++ / 600 |
| A375 melanoma | DMEM | ++++ / 1000 |
| SK-Mel-1 melanoma | MEM (suspension cells) | / 300 |

*1+: <10 scc; 2+: >30 scc; 3+: >50 scc; 4+: >80 scc; 5+: >100 scc; and scc: single cell clone. MEM (Minimal Esstential Medium); NaPy (sodium pyruvate); NE a.a. (non-essential amino acids).

The results shown in Table 2 demonstrate that most of the established human tumor cells were efficiently transduced by the pLSNB70 virus. Some of the tumor cells are more resistant to G418 than others. The transduction rate was determined by counting the number of G41 8-resistant cell colonies. Expression of the B7-2 gene was demonstrated by immunohistochemical staining using an anti-B7-2 mono-clonal antibody. Except for the few cell lines that were sensitive to low levels of G418 (e.g., PC3), most of the tumor cell lines tested were efficiently transduced with the B7-2 gene, and selected by G418 within two weeks.

EXAMPLE 7

Transduction And Expression Of B7-2 In Primary Tumor Cells

Retroviral transduction of established cell lines is generally more efficient than transduction of primary tumor cells. For in vivo or ex vivo gene transduction, however, the target cells are fresh (i.e., primary) tissues or tumors. It is thus important to demonstrate B7-2 transduction in freshly isolated primary tumor cells. To this end, several tumor specimens from surgery or biopsy were propagated in culture for less than 5 passages and transduced with the pLSNB70 virus as described in Ex. 2. After transduction, the cultures were selected with G418. The results are summarized in Table 3.

TABLE 3

Retroviral Transduction Of Primary Tumor Cultures

| Cell type | Medium | Transduction / Rate*/μg/ml |
|---|---|---|
| E81 (p11) | F12/DME | ++ / 250 |
| E82 (p3) | F12/DME | ++++ / 250 |
| E81 (p11) | F12/DME | + / 250 |
| Hepatoma (PC) | RPMI; F12/DME | − / 500 |
| Melanoma (DD) | RPMI | ++ / 250 |
| Melanoma (DJ) | RPMI | ++ / 250 |
| Adenocarcinoma (BP) | RPMI | +++ / 250 |
| Adenocarcinoma (LJ) | RPMI | +++ / 250 |

*(1+: <10 scc; 2+: >30 scc; 3+: >50 scc; 4+: >80 scc; 5+: >100 scc;scc, single cell clone).

As shown in Table 3, primary tumor cultures were found to be sensitive to low concentrations of G418 (approximately 250 μg/ml G418). Nevertheless, most of the transduced cells were selected within 10 days. The results shown in Table 3 illustrate the successful transduction of three primary gliomas, two melanomas and two adenocarcinomas with pLSNB70. B7-2 expression was also confirmed by immunohistochemical staining using a mouse anti-B7-2 antibody as the primary antibody and a FITC-labeled goat anti-mouse antibody as the secondary antibody. The majority of the selected cells (i.e, the transduced tumor cells that survived growth in the presence of G418) showed positive surface staining for B7-2.

EXAMPLE 8

Retroviral Transduction Of GM-CSF In Established And Primary Tumor Cells

In animal studies, a high level of GM-CSF expression has been shown to be related to its therapeutic efficacy [Jaffee et al. (1993) Cancer Res. 53:2221 and Dranoff et al. (1993) Proc. Natl. Acad. Sci. USA 90:3539]. Two different retroviral vectors were constructed that contained the human GM-CSF cDNA to examine the level of GM-CSF expressed in transduced tumor cells. The first vector pLSN, which contains the wild type MoMLV LTR, was described above in Ex. 1 as was the construction of pLSNGM1. The second vector, pLGCTSN (ATCC 97803; Robinson et al., supra), contains a modified LTR in which the MoMLV U3 region is replaced by the CMV-IE enhancer/promoter and the HIV TATA and TAR elements which leads to an increased level of expression in human cells; in addition, pLGCTSN contains an extended packaging signal and a 3' splice acceptor sequence from MoMLV. The human GM-CSF cDNA was inserted into pLGCTSN to create pLGCTSN-GM1 as follows. The GM-CSF gene was released from pBS-GM-CSF (Ex. 1) by digestion with HindIII and BamHI and this fragment was inserted into HindIII- and BamHI-digested pLGCTSN to generate pLGCTSN-GM1.

A human melanoma cell line (SK-MEL-1; ATCC HTB 67) and the primary adenocarcinoma (LJ) culture ["AD1 (LJ)"] were transduced with retroviruses derived from either pLSNGM1, pLGCTSN-GM, pLSNBG9 or pLSNB70, and selected with G418. The expression of GM-CSF was determined by ELISA using culture supernatants collected from the G418-selected cultures. Table 4 summarizes the amount of GM-CSF (ng/$10^6$ cells/24 hr) present in the culture supernatants.

TABLE 4

ELISA Of GM-CSF Expression In Established And Fresh Tumor Cell Cultures

| Vector | SK-MEL-1 | AD1(LJ) |
|---|---|---|
| Control (pLSNB70) | 0.1 | 0.03 |
| pLSNGM1 | 9 | 4 |
| pLGCTSN-GM | 9 | 8 |
| pLSNBG9 | 9 | 0.65 |

The virus derived from pLSNB70 (encodes B7-2) was used as a negative control for the expression of GM-CSF in the transduced cells; pLSNB70-transduced melanoma cells expressed GM-CSF at <0.1 ng/ml/$10^6$ cells in 24 h which was close to the background level of the ELISA. The pLSNGM1- and the pLGCTSN-GM-transduced cells expressed 9 ng/ml/$10^6$ cells of GM-CSF in 24 hr. This study used an established human melanoma cell line (SK-MEL-1) and the level of GM-CSF expression was determined 3 months after cells were selected by G418.

A similar study was performed using a primary human adenocarcinoma culture AD1(LJ). The primary culture was prepared as follows. The tumor tissue was surgically removed, placed in HBSS on ice immediately after surgery and transferred to a biosafety hood. Ten milliliters of HBSS was placed in a sterile petri dish and the tumor tissue was added. Using forceps and a scalpel, normal tissue surrounding the tumor was removed and the tumor was transferred to a second petri dish containing 5–10 ml HBSS and the tumor was minced. Ten ml of a suspension containing the minced tumor was transferred to a 15 ml tube and the cells were collected by centrifugation at 100×g for 8 min. at room temp. The cells were resuspended in 2 ml of DMEM containing 20% FCS. The resuspended cells (2–3 ml) were transferred to a 50 ml tube and the following enzymes were added: 1 mg/ml collagenase type V, 10 μg/ml hyaluronidase type V, 300 U/ml DNase type IV and 10 μg/ml gentamycin sulfate. The cells suspension was then incubated at 37° C. with shaking for 60 min. The cells were then plated in tissue culture flasks containing DMEM containing 10% FCS, 10 μg/ml gentamycin sulfate, penicillin/streptomycin/glutamine solution (Gibco/BRL) and 1.25 μg/ml amphotericin (growth medium) and grown overnight in an incubator containing 5% $CO_2$ at 37° C. On the second day, non-adherent cells were removed by washing the flasks with 3 ml growth medium. The medium was changed every 3–7 days depending upon the growth rate of the cells. The cells were transduced with the pLSNB70 virus and grown in the presence of G418 as described above.

As shown in Table 4, the transduced and selected primary human tumor cells [AD1(LJ)] produced GM-CSF in the range of 1–8 ng/ml/$10^6$ cells/24 hr (GM-CSF expression was determined 2–3 weeks after the cells were selected using G418). Thus, the un-modified retroviral vector pLSN is capable of producing high levels of GM-CSF in primary human tumor cells. The level of GM-CSF expression may be cell-type dependent, and further modification of the vector (e.g., use of cell-type- or tissue-specific enhancers and/or promoters) may further increase the level of expression in specific tumor cells.

EXAMPLE 9

Bi-Cistronic Expression Of B7-2 And GM-CSF In Established And Primary Tumor Cells To express both the B7-2 and GM-CSF therapeutic genes simultaneously in tumor cells, the bi-cistronic retroviral vector pLSNBG9 (Ex. 1) was employed. The plasmid DNA was transfected into PA317 cells and virus was harvested and used for transduction as described in Ex. 1. Both the established melanoma cell line SK-MEL-1 and the primary adenocarcinoma cell culture AD1(LJ) were transduced and selected by G418. After selection (typically 2 weeks after applying G418), the expression of GM-CSF and B7-2 in these two cell types was determined by ELISA (Table 4) and flow cytometry, respectively. Table 4 shows that the level of GM-CSF expression for the bi-cistronic vector was similar to the mono-cistronic vector pLSN-GM in SK-MEL-1 cells but was ten times less than the mono-cistronic vector in the primary AD1(LJ) culture. The FACS analysis indicated that the mono-cistronic (pLSNB70) and bi-cistronic (pLSNBG9) vectors expressed B7-2 in both cell types. These results demonstrate that both B7-2 and GM-CSF can be expressed simultaneously following transduction of established and primary tumor cultures with virus derived from the bi-cistronic pLSNBG9 vector.

EXAMPLE 10

Construction Of Expression Vectors For The High Level Expression Of Therapeutic Genes The promoter strength of the retroviral vector determines the expression level of the transduced gene in eukaryotic cells. To increase the level of gene expression, we have modified the MLV vector and generated a series of vectors with enhanced promoter strength (Robinson et al., supra). To further improve the promoter strength, the strength of several promoters was examined in the human tumor cell line, HeLa (ATCC CCL 2), using a reporter CAT assay. Plasmids in which the CAT gene was placed under the transcriptional control of either the CMV-IE promoter/enhancer, the EF1α promoter/enhancer with or without intron 1, the MCT promoter (the modified MoMLV LTR present in pLGCTSN), and the HIV LTR (a number of these CAT constructs are described in Robinson et al., supra). The plasmids were transfected into HeLa cells and 48 hr later cell lysates were prepared and assayed for CAT activity as described (Robinson et al., supra). Constructs containing plasmids comprising the HIV-1 TAR element (i.e., the HIV LTR and the pMCT promoters) were also co-transfected along with a tat expression construct. The results are summarized in Table 5. In Table 5, the promoter activity is expressed relative to the activity of the CMV-IE promoter. In Table 5, the following abbreviations are used: EF1α+intron (the 1.442 kb EF1α enhancer/promoter element comprising intron 1); EF1α–intron (a 475 bp fragment containing the EF1α enhancer/promoter corresponding to map units 125 to 600 of the human EF1α gene) HIV+Tat (the pHIV-1/LTR-cat construct co-transfected with the tat expression construct); MCT (pMCT-cat); and MCT+Tat (pMCT-cat co-transfected with the tat expression construct).

TABLE 5

| Promoter | Relative Activity |
|---|---|
| CMV – IE | 1.0 |
| EF1α + Intron | 2.16 |
| EF1α – Intron | 0.02 |
| HIV + Tat | 0.13 |
| MCT | 0.32 |
| MCT + Tat | 1.2 |

The results shown in Table 5 indicate that the human EF1α promoter plus its intron has the strongest activity compared with all other promoters tested. Thus, the EF1α promoter may be used to drive the expression of therapeutic genes in tumor cells. Retroviral and plasmid constructs in which the EF1α+intron promoter/enhancer is used to drive the expression of therapeutic genes is described below.

a) Construction Of A Plasmid Expression Vector Containing The EF1α Enhancer/Promoter The human EF1α enhancer/promoter is abundantly transcribed in a very broad range of cell types including L929, HeLa, CHU-2 and COS cells [Uetsuki, T. et al., J. Biol. Chem., 264:5791 (1989) and Mizushima, S. and Nagata, S., Nuc. Acids. Res., 18:5322 (1990)]. A 1.442 kb fragment containing the human EF1α enhancer/promoter and a splice donor and acceptor from the human EF1α gene was isolated from human genomic DNA as follows. The 1.442 kb fragment corresponds to map units 125 to 1567 in the human elongation factor 1α gene (SEQ ID NO:14).

Genomic DNA was isolated from the MOU cell line (GM 08605, NIGMS Human Genetic Mutant Cell Repository, Camden, N.J.) using standard techniques [Sambrook, J. et al., *Molecular Cloning: A Laboratory Manual*, 2nd. ed., Cold Spring Harbor Laboratory Press, (1989) pp. 9.16–9.23]. Two synthetic oligonucleotide primers were used to prime the polymerase chain reaction (PCR) for the isolation of the 1.442 kb fragment containing the human EF1α enhancer/promoter. U.S. Pat. Nos. 4,683,195, 4,683,202 and 4,965,188 cover PCR methodology and are incorporated by reference.

The 5' primer, designated HEF1αL5, contains the following sequence: 5'-AAGCTTTGGAGCTAAGCCAGCAAT-3' (SEQ ID NO:15). The HEF1αL5 primer generates a HindIII site at the 5' end of the 1.442 kb fragment. The 3' primer, designated HEF1αL3B, contains the following sequence: 5'-TCTAGAGTTTTCACGA CACCTGA-3' (SEQ ID NO: 16). The HEF1αL3B primer generates a Xba I site at the 3' end of the 1.442 kb fragment. PCR conditions were as reported in Saiki, R. K. et al., Science 239:487 (1988). Briefly, 10 μg MOU genomic DNA and 1 μM final concentration of each primer were used in a 400 μl PCR reaction. Reaction conditions were 94° C. for 1 minute, 60° C. for 1 minute, 72° C. for 1.5 minutes, 30 cycles. Taq DNA polymerase was obtained from Perkin-Elmer Cetus; the reaction buffer used was that recommended by the manufacturer. The PCR reaction products were electrophoresed on a low melting agarose the 1.442 kb fragment was gel purified and digested with HindIII and XbaI. The HindIII/XbaI fragment was then inserted into pSSD5 (described below) to generate pHEF1αBSD5.

pSSD5 was constructed by digestion of the plasmid pLI [Okayama, H. and Berg, P., Mol. Cell. Biol., 3:280 (1983)] with PstI and EcoRI. Synthetic oligonucleotides (Operon) were ligated onto the PstI and EcoRI ends of pLI to generate the polylinker of pSSD5 (the SD5 polylinker). The sequences of the oligonucleotide pair used to create the polylinker are: SD5A 5'-TCTAGAGCGGCCG CGGAGGCCGAATTCG-3' (SEQ ID NO:17) and SD5B 5'-GATCCGAATTCGGCC TCCGCGGCCGCTCTAGATGCA-3' (SEQ ID NO:18). The ligation of this oligonucleotide pair into pLI destroyed the PstI site. Following the addition of the polylinker, the plasmid was digested with HindIII and partially digested with BamHI.

The 572 bp HindIII/BamHI fragment containing the SV40 enhancer/promoter, the 16S splice junction and the SD5 polylinker was isolated by electrophoresis of the digestion products on a low melting temperature agarose gel (SeaPlaque, FMC BioProducts, Rockland, Me.). The 572 bp fragment was cut out of the gel and the agarose was removed by digestion with β-Agarase I (New England Biolabs) followed by isopropanol precipitation according to the manufacturer's directions.

The 572 bp fragment was inserted into the plasmid pcDV1 [Okayama and Berg, supra] as follows: pcDV1 was digested with HindIII and BamHI and the 2.57 kb fragment containing the SV40 poly A sequences and the pBR322 backbone was ligated to the 572 bp fragment containing the SV40 enhancer/promoter, 16S splice junction and polylinker. The resulting plasmid was named pSSD.

The 671 bp BamHI/PstI fragment containing the SV40 poly A sequences (SV40 map units 2533 to 3204) was removed from SV40 DNA and cloned into pUC19 digested with BamHI and PstI. The resulting plasmid was then digested with BclI (corresponds to SV40 map unit 2770). The ends were treated with the Klenow enzyme and dNTPs to create blunt ends. Unphosphorylated PvuII linkers (New England Biolabs) were ligated to the blunted ends and the plasmid was circularized to create pUCSSD. The SV40 poly A sequences can be removed from pUCSSD as a BamHI/PvuII fragment.

pSSD5 was constructed by ligating together the following three fragments:
1) the 1873 bp SspI/PvuII fragment from pUC19; this provides the plasmid backbone;
2) the 796 bp fragment containing the SV40 enhancer/promoter and 16S splice junction and the polylinker from pSSD; this fragment was obtained by digestion of pSSD with SspI and partial digestion with BamHI followed by isolation on low melting agarose and recovery as described above; and 3) the 245 bp BamHI/PvuII fragment from pUCSSD (this fragment contains the SV40 poly A sequences). The three fragments were mixed together and ligated using T4 DNA ligase to create pSSD5. The polylinker of pSSD5 contains the following restriction sites: XbaI, NotI, SfiI, SacII and EcoRI.

b) Construction Of pHEF-B70

A plasmid, pHEF-B70, in which the EF1α enhancer/promoter is used to drive the expression of the human B7-2 gene was constructed as follows. The B7-2 gene was removed from pLCTSNB70 (described below) by digestion with BamHI and the isolated B7-2 fragment was ligated into BamHI-digested pHEF1αBSD5 to generate pHEF-B70.

pLCTSNB70 was constructed by ligating the B7-2 gene released from pT7T318U-B7-2 (Ex. 1) by BamHI digestion into BamHI-digested pLCTSN (ATCC No. 97802; Robinson et al., supra).

c) Construction Of pHEF-IL-12

In the plasmid pHEF-IL-12, the IL-12A and IL-12B genes are under the transcriptional control of the EF1α enhancer/promoter.

i) Cloning Of The Human IL-12 cDNA

RNA was isolated from activated NC37 B cells (ATCC CCL 214) and the IL-12A and IL-12B cDNAs were isolated by RT-PCR as described in Ex. 1. The following primers were employed for the amplification of the IL-12A cDNA: 5'-GAA GATCTGCGGCCG <u>CCACCATG</u>TGGCCCCCTGGGTCAGC-3' (SEQ ID NO:19; optimized initiation sequence underlined) and 5'-CCTCTCGAGTTAGGAAGCATTCA GATAGC-3' (SEQ ID NO:20). The PCR product was cloned directly into EcoRV-digested pBluescript KS(−) to generate pKS-IL-12A. The IL-12A coding region is provided in SEQ ID NO:21.

The following primers were employed for the amplification of the IL-12B cDNA: 5'-AAAGAGCT CCACCATGTGTCACCAGCAGTTGGTC-3' (SEQ ID NO:22; optimized initiation sequence underlined) and 5'-AAGGATCCTAACTGCAGG GCACAGATGC-3' (SEQ ID NO:23). The PCR product was cloned directly into EcoRV-digested pBluescript KS(−) to generate pKS-IL-12B; the IL-12B coding region is provided in SEQ ID NO:24. Proper construction of both IL-12 constructs was verified by restriction enzyme digestion.

ii) Construction Of pLSN-IL-12 pLSN-12 is a retroviral vector containing a IL-12A-IRES-IL-12B bi-cistron. To construct pLSN-IL-12, the following four fragments were gel purified: the IL-12A gene released from pKS-IL-12A by digestion with ClaI and PspAI; the IL-12B gene released from pKS-IL-12B by digestion with NotI and XhoI; the EMCV IRES was released from pGEM-IRES8 by digestion with XhoI and ClaI; and a pLSN vector backbone containing a PspAI site generated by removing the HIV vpr gene from pLSNvpr (described below) by digestion with MluI and PspAI. These four fragments were combined and ligated with NotI- and MluI-digested pLSNvpr to generate pLSN-IL-12.

pLSNvpr was constructed by digestion of pBS-vpr with NotI and XhoI and the vpr gene fragment was ligated with NotI- and XhoI-digested pLSN. The vpr gene was PCR amplified from pNL4-3 [Adachi et al. (1986) J. Virol. 59:284] and inserted into pBluescript KS(−) to generate pBS-vpr.

iii) Construction Of pHEF-IL-12

To construct pHEF-IL-12, the following three fragments were isolated: the IL-12A gene was released from pKS-12A by digestion with ClaI and PspAI; the IL-12B gene released from pKS-IL-12B by digestion with NotI and XhoI; the EMCV IRES was released from pGEM-IRES8 by digestion with XhoI and ClaI. These fragments were cloned into NotI- and PspAI-digested pHEFvpr. pHEFvpr was constructed by ligation of a 360 bp BamHI fragment isolated from pLSNvpr with pHEF1αBSD5 that had been digested with BamHI and treated with alkaline phosphatase.

d) Construction Of pHEF-IL-12-GM-CSF pHEF-IL-12-GM-CSF contains a IL-12A-EMCV IRES-IL-12B-poliovirus IRES-GM-CSF tri-cistron under the transcriptional control of the EF1α enhancer/promoter. To construct pHEF-IL-12-GM-CSF, the following four fragments were gel purified: a 2373 bp NdeI-PspAI fragment containing the IL-12B-EMCV IRES-IL-12A cistron isolated from pHEF-IL12; a 1320 bp NdeI-SphI fragment containing the EF1α intron isolated from pHEF-IL-12; a 735 bp PspAI-XhoI fragment containing the poliovirus IRES from pKS-P2 (an equivalent DNA fragment is generated by PCR amplification of the IRES located within the first ~730 bp of the poliovirus genome [LaMonica et al. (1986) J. Virol. 57:515] using primers that will generate PspAI and XhoI sites).

e) Construction Of pHEF-GM-CSF pHEF-GM-CSF was derived from pHEF-IL-12-GM-CSF by complete digestion with SmaI and partial digestion with HincII. The resulting approximately 4409 bp fragment was gel purified and self-ligated to produce pHEF-GM-CSF.

f) Construction Of pHEF-BG

A plasmid, pHEF-BG, in which the 1.442 kb EF1α enhancer/promoter is used to drive the expression of both the human B7-2 and GM-CSF cDNAs (a bi-cistronic construct) is constructed as follows. The B7-2-IRES-GM-CSF bi-cistronic fragment was removed from pLSN-BG9 (Ex. 1) by digestion with NotI and BamHI and the gel purified fragment was inserted into NotI- and BamHI-digested pHEF1αBSD5 to generate pHEF-BG.

g) Construction Of The pLSN-IL-12-GM-CSF Retroviral Vector pLSN-IL-12-GM-CSF provides a retroviral vector in which the MoMLV LTR is used to drive the expression of both the human IL-12 gene and GM-CSF cDNAs. pLSN-IL-12-GM-CSF was constructed by ligation of the following four fragments into BamHI-digested pLSN-GFP: the 1489 bp MoMLV vector fragment derived from SacII-XbaI-digested PLSN-GFP; the 1680 bp IL-12B-IRES containing fragment from XbaI-NotI-digested pHEF-IL-12; the 760 bp IL-12A containing fragment from NotI-PspAI digested pHEF-IL-12; and the 1252 bp GM-CSF containing fragment from PspAI-BamHI digested pHEF-IL-12-GM-CSF.

h) Construction Of The pLCTSN-pA-BG-EF Retroviral Vector pLCTSN-pA-BG-EF contains a cistron comprising the EF1α enhancer/promoter, B7-2 and GM-CSF cDNAs and SV40 polyadenylation signal inserted in an inverted orientation (relative to transcription from the 5' LTR). This vector was constructed by ligation of the following three fragments with HindIII and SalI digested pLCTSN vector: EF1α enhancer/promoter from SalI-NotI digested pHEF, B7-2/IRES/GM-CSF cistron from SalI-NotI digested pLCTSN-BG, and SV40 polyA signal from BglII-HindIII digested pSP72SVpA.

pLCTSN-BG was constructed by gel-purifying the following three DNA fragments: the B7-2 cDNA from pLSNB70 cut with NotI-XhoI, the EMCV IRES from pGEM-IRES8 cut with XhoI-HindIII (HindIII partial), and the GM-CSF cDNA from PCR amplified and HindIII-BamHI digested DNA (Ex. 1). The purified fragment were then ligated with NotI-BamHI digested pLCTSN to create pLCTSN-BG.

i) Construction Of The pLCT-pA-BG-EF Retroviral Vector pLCT-pA-BG-EF contains a cistron comprising the EF1α enhancer/promoter, B7-2 and GM-CSF cDNAs and SV40 polyadenylation signal inserted in an inverted orientation (relative to transcription from the 5' LTR) but lacks the the neo gene found in pLCTSN-pA-BG-EF vector. pLCT-pA-BG-EF was constructed by ligation of the following three fragments with HindIII-SalI digested pLCTSN: EF1α enhancer/promoter from SalI-NotI digested pHEF, the B7-2/IRES/GM-CSF cistron from NotI-BamHI digested pLCTSN-BG, and the SV40 polyA signal from NotI-HindIII digested pSP72SVpA.

pSP72SVpA was made by PCR amplification of the SV40 polyA signal from pBlueBac-His B (Invitrogen) with primers containing HindIII and EcoRI sites and cloned into HindIII-EcoRI digested pSP72 (Promega).

The plasmids described above are introduced into tumor cells, including freshly explanted tumor cells as well as tumor cells in a patient, using injection of naked plasmid DNA, liposome mediated gene transfer or through the use of a gene gun (biolistics). The retroviral vectors described above are used to generate recombinant virus which is used to transduce the encoded IMGs into tumor cells (primary and established) in culture as described in Exs. 1 and 2.

j) Demonstration of Biologically Active GM-CSF From the GM-CSF Cistron

To demonstrate that the GM-CSF cDNA sequences isolated by PCR amplification and used to generate mono- and multi-cistronic constructs are capable of expressing active GM-CSF, the following GM-CSF bioactivity assay was performed using the GM-CSF-dependent Mo7e cell line [Genetics Institute, Cambridge, Mass.; Avanzi el al. (1990) Cellular Phyisol. 145:458].

Mo7e cells were maintained in DMEM supplemented with 10% FBS, 2 mM L-glutamine, 100 U/ml penicillin-streptomycin, and 100 U/ml GM-CSF at 37° C., 10% $CO_2$.

When the cells were at exponential growth phase (viability >90%), they were washed twice with DMEM, and cultured for 48 hours in the absence of GM-CSF. After two days of GM-CSF starvation, the Mo7e cells, with around 20% viability, were washed once with DMEM and seeded into V-bottomed 96-well plates at $1 \times 10^4$ cells/well in a total volume of 200 µl with serial dilutions of a standard GM-CSF solution of known concentration or supernatant harvested from HeLa cells transfected with either pHEF-GM-CSF or pHEF-IL-12-GM-CSF plasmid DNA (a 1:2000 dilution of the culture supernatant was employed). After two days of culturing at 37° C., 10% $CO_2$, to each well, 20 µl of MTT (3-[4,5-dimethylthiazol-2-yl]-2,5-diphenyltetrazolium bromide) (5 mg/ml in PBS) was added and the plates were incubated for another 6 hours. The purple crystals were then collected at the bottom the well by brief centrifugation and the supernatant was aspirated. The pellets were dissolved in 100 µl of acidified isopropanol. The optical density at 570 nm ($OD_{570}$) of each well was obtained using a microplate reader. A standard curve was constructed by plotting the known GM-CSF concentrations against the $OD_{570}$ reading. GM-CSF concentration in the harvested supernatant was obtained by comparing its OD with the standard curve. The results are summarized in Table 7.

TABLE 7

Determination Of GM-CSF Concentration In Cell Culture Supernatants Of Transfected HeLa Cells

| Samples | GM-CSF Bioactivity (U/ml) | GM-CSF Protein Content (pg/ml) | $OD_{570}$ |
| --- | --- | --- | --- |
| Standard 1 | 0 | 0 | 0.2 |
| Standard 2 | 0.01 | 1 | 0.203 |
| Standard 3 | 0.05 | 5 | 0.233 |
| Standard 4 | 0.2 | 20 | 0.343 |
| Standard 5 | 0.5 | 50 | 0.60 |
| Standard 6 | 1 | 100 | 0.65 |
| pHEF-GM-CSF (1:2000) | 0.29 | 29 | 0.365 |
| pHEF-IL-12-GM-CSF (1:2000) | 0.03 | 3 | 0.235 |

The results shown in Table 7 demonstrate that the PCR amplified GM-CSF sequences encode biologically active GM-CSF. In addition these results demonstrate that placing the GM-CSF cistron downstream of another cistron (i.e., pHEF-IL-12-GM-CSF) reduces the amount of GM-CSF expressed (relative to a mono-cistronic expression vector). While the level of GM-CSF is reduced when G-CSF is the second or downstream cistron, the amount of GM-CSF produced in multi-cistronic GM-CSF construct is sufficient to provoke a biological response as demonstrated by the ability of tumor cells transduced with a bi-cistronic retrovirus (i.e., pLSNBG9) to induce systemic immunity against unmodified tumor cells (Ex. 5).

EXAMPLE 11

Human Tumor And PBL Engraftment In SCID/beige Mice

An in vivo hu-PBL-SCID mouse/human tumor model was established to study the combined effects of B7-2 and GM-CSF expression in human tumor cells. C.B-17 scid/scid mice [Boussiotis et al. (1993) Proc. Natl. Acad. Sci. USA 90:11059] lack both T- and B-cell function but do maintain normal myeloid cell, natural killer (NK) cell, macrophage and dendritic cell functions [Shpitz et al. (1994) J. Immunol. Meth. 169:1]. To also avoid the NK activity of the SCID mouse, a new SCID mouse strain, SCID/bg, which has the NK cell function deleted was employed (C.B-17-scid-beige Inbred, Taconic).

To investigate the ability of SCID/bg mice to support the growth of human tumor cells, several established human tumor cell lines and 5 primary tumors were transplanted into the SCID/bg mice and the mice were monitored for tumor growth for up to 5 months. Primary tumors were treated as follows. Tumor samples were obtained in the operating room at the time of resection under sterile conditions. One to three grams of tumor were harvested for immediate processing. Fresh tumor biopsies were dissected to remove necrotic debris and connective tissue and were minced into 1–2 mm pieces. The pieces were then treated with the following enzymatic solutions in HBSS to provide cell suspensions:

for glioblastomas: 0.025% collagenase, 0.04% DNase and 0.05% Pronase with shaking for 30 min at 37° C. and a further 30 min at 4° C. DMEM/F12 was used as the basis of the growth medium for primary glioblastoma cultures;

for hepatomas: 1 mg/ml collagenase type IV, 300 U/ml DNase type IV and 10 µg/ml gentamycin sulfate at 37° C. with shaking for 30 min. RMPI 1640 or DMEM/F12 was used as the basis of the growth medium for primary hepatoma cultures;

for colon adenocarcinomas: tumors were processed by physical dissociation (cutting) or by enzymatic treatment using 1 mg/ml collagenase type V, 10 µg/ml hyaluronidase type V, 300 U/ml DNase type IV and 10 µg/ml gentamycin sulfate. The cells suspension was then incubated at 37° C. with shaking for 60 min. DMEM was used as the basis of the growth medium for primary adenocarcinoma cultures.

for melanomas: tumor cells were treated using the enzyme solution described above for adenocarcinomas. RPMI 1640 was used as the basis of the growth medium for primary melanoma cultures.

The resulting cell suspensions were then filtered through a fine mesh and layered onto a Ficoll-hypaque density gradient medium (Sigma) and centrifuged at 400×g for 30 min at room temp. The cells at the interface were removed and washed twice with HBSS (centrifuged at 100×g for 10 min) and counted. The cells were then seeded into the appropriate medium [e.g., RPMI 1640, DMEM, DMEM/F12 (all available from Sigma), etc. containing 10% FCS and antibiotics if desired] for culturing, resuspended into freezing medium for storage or used directly for injection into mice or for gene transfection applications.

Three to four million primary tumor cells and 2 to 6 million cells from established tumor cell lines were injected SC per flank of SCID/bg mice (both flanks were injected if a large enough cell sample was available). The mice were monitored for the presence of palpable tumors. The results are summarized in Table 8.

TABLE 8

Establishment Of Solid Human Tumors In SCID/bg Mice

| Tumor Inoculation | No. Of Cells Injected | No. Of Mice | Palpable Tumor Established (Days Post-Inoculation) | Success Rate (%) |
|---|---|---|---|---|
| Cell Lines | | | | |
| Melanoma | | | | |
| A375 | 2–5 × 10$^6$ | 30 | 5–8 | 100 |
| SK-MEL-1 | 4 × 10$^6$ | 12 | 20–30 | 100 |
| Hepatoma | | | | |
| HepG2 | 3 × 10$^6$ | 5 | 10–15 | 100 |
| Breast Cancer | | | | |
| MDA468 | 2–5 × 10$^6$ | 35 | 5–7 | 100 |
| MCF7 | 4–6 × 10$^6$ | 7 | 8–14 | 100 |
| Glioblastoma | | | | |
| D54MG | 2 × 10$^6$ | 5 | 5–6 | 100 |
| Primary Tumors | | | | |
| Melanoma | | | | |
| Mel DD | 4 × 10$^6$ | 8 | 30–40 | 100 |
| Mel DJ | 3 × 10$^6$ | 4 | 30–40 | 100 |
| Mel TM | 3 × 10$^6$ | 5 | 30–40 | 100 |

The results shown in Table 8 demonstrate that the SCID/bg mice can support growth of the established human tumor lines very efficiently and they support the growth of some primary tumor cells (e.g., melanoma cells), albeit with a lower efficiency relative to the use of established tumor cell lines. Injection of 3×10$^6$ primary glioblastoma cells (Ed 86 and Ed 120) as well as injection of primary heptatoma cells (single donor) did not give rise to palpable tumors within 3 months in SCID/bg mice.

T-cell mediated allograft rejection has been demonstrated in SCID mice (scid/scid) engrafted with human PBLs [Malkovska et al. (1994) Clin. Exp. Immunol. 96:158] or human splenocytes [Alegre et al. (1994) J. Immunol. 153:2738]. However, the SCID/bg mouse strain has not previously been used in hu-PBL reconstitution studies. To determine whether the SCID/bg mouse could be reconstituted with human PBLs to provide an animal model for in vivo cancer gene therapy, SICD/bg mice were reconstituted with human PBLs by injecting 2×10$^7$ freshly isolated human PBLs into the peritoneal cavity. After 4–8 weeks, the PBL-injected mice were sacrificed and cells harvested from the peritoneal cavity, spleen, and peripheral blood were analyzed by FACS using antibodies against mouse or human cell markers. Isotype-matched mouse Igs were used for control staining. The results are summarized in Table 9. The following antibodies were used in these experiments: human markers: anti-CD45 (anti-HLe-1, Becton Dickinson), anti-CD3 (Leu-4, Becton Dickinson), anti-CD4 (Becton Dickinson), anti-CD8 (Becton Dickinson) and mouse marker: anti-mouse-H-2K$^d$ (Pharmingen).

TABLE 9

| | % Human CD45 |
|---|---|
| Spleen | 1–59% |
| PBL | 0.1–17% |
| Peritoneal Cavity | 5–69% |

The results shown in Table 9 demonstrate that SCID/bg mice were efficiently reconstituted with human lymphocytes, with CD45+ human cells constituting up to ~60% of splenocytes, up to 17% of PBLs and up to ~70% of cells obtained by peritoneal lavage in the reconstituted mice.

The percentage of different human lymphocyte subsets in the CD45+ population present in the reconstituted SCID/bg mice was examined by FACS as follows. SCID/bg mice were reconstituted with PBLs isolated from three healthy human donors as described in Ex. 3. After 4–8 weeks, the PBL-injected mice were sacrificed and lymphoid organs, PBLs and peritoneal exudates were harvested and were analyzed by FACS. The percentage of T lymphocyte subsets was also determined within the CD45+ population in the peripheral blood of human donors A and B. The following markers were examined: CD45RO (anti-CD45RO, Becton Dickinson), CD45RA (anti-CD45RA, Becton Dickinson), HLA-DR (MG2600, Caltag), CD4 and CD8. The results are summarized in Table 10. In Table 10, the following abbreviations are used: RA+ (CD45RA positive); RO+ (CD45RO positive); RO+DR+ (CD45RO and HLA-DR positive).

TABLE 10

Percentage Of T Lymphocyte Subsets In The CD45+ Population In Hu-PBL-SCID/bg Mice

| Donor/Mouse | CD4+ | CD8+ | CD4+8+ | RO+ | RA+ | RO+DR+ |
|---|---|---|---|---|---|---|
| Donor A | 53 | 23 | 1.5 | 58 | 37 | 9.9 |
| SCID/bg-A | 72 | 42 | 17 | 99 | 1 | 67 |
| Donor B | 63 | 25 | 1.6 | 58 | 37 | 9.4 |
| SCID/bg-B | 41 | 48 | 12 | 92 | 8 | 67 |
| SCID/bg-C | 51 | 44 | 21 | 76 | 24 | 35 |

The results shown in Table 10 demonstrate that the peripheral blood of the Hu-PBL-SCID/bg mice contain high numbers of immature or progenitor T cells (i.e., CD4+8+ cells and CD45RA+ cells). These results are in contrast to the results obtained by reconstitution of C.B-17scid/scid mice (Hu-PBL-SCID). In human PBL-reconstituted C.B-17 scid/scid mice most human lymphocytes exhibit activated cell phenotypes (HLA-DR+ and CD25+ or CD69+) soon after reconstitution, and almost all (>99%) human T cells exhibit mature memory phenotypes (CD45RO+) in a state of reversible anergy [Rizza el al. (1996), supra; Tarry-Lehmann and Saxon, supra; Tarry-Lehmann et al., supra]. Therefore, the lack of sufficient numbers of immature naive T cells after reconstitution renders the Hu-PBL-SCID model unsuitable for the evaluation of anti-tumor immunity. In contrast, the Hu-PBL-SCID/bg mice show evident levels of CD45RA+ and CD4+8+ cells 4–6 weeks after reconstitution. Thus, the Hu-PBL-SCID/bg mice of the present invention provide a suitable model for the evaluation of anti-tumor immunity.

EXAMPLE 12

Autologous Hu-PBL-SCID/bg/Human Tumor Model

To provide an autologous Hu-PBL-SCID/bg/human tumor model, primary human tumor cells are prepared and injected SC into the flanks of SCID/bg mice as described in Ex. 11. The primary tumor cells are first transduced with vectors encoding one or more therapeutic proteins (e.g., B7-2, GM-CSF, IL-12A, IL-12B, etc.) and mice are injected with the transduced tumor cells (after selection) as well as non-transduced tumor cells. Once palpable tumors are established (1–2 months), the mice are reconstituted with autologous PBLs (i.e., PBLs isolated from the same patient that provided the tumor cells). For each tumor, a minimum of 10 SCID/bg mice are injected with tumor cells and the rate of establishment of palpable tumors is determined. Tumors that grow with a success rate of >40% in the injected mice will receive autologous PBLs and 1 week later will receive IMG-transduced tumor cells. The tumor size (mm$^3$) is measured every 3–4 days and the mice are monitored for survival. These mice are used to determine which combinations of therapeutic or immune-modulating genes (IMGs) result in the regression of tumor size and prolonged mouse survival.

Mice from each group are sacrificed at various intervals and spleen cells and draining lymph node cells are assayed for immune reactivity (i.e., anti-tumor cellular immunity) (e.g., $^{51}$Cr release assays, proliferation and cytokine production) to determine whether any of the assays of immune reactivity correlate with observed tumor rejection.

Proliferation Assays And In Vitro Priming

Splenocytes and lymph node cells isolated from the reconstituted mice are co-cultured with lethally irradiated tumor cells transduced with IMGs for various lengths of time (minimum of 5 days) and assayed for proliferation by pulsing the cultures with $^3$H-thymidine, e.g., on day 4 of culture and determining $^3$H-thymidine incorporation into cellular DNA 18–24 hr later.

Responding lymphocytes may be restimulated repeatedly (weekly) with untransduced or transduced tumor cells to increase the frequency of T cell precursors specific to the tumor. The tumor-responsive immune cells are then transferred into mice carrying the parental tumor to determine if in vitro priming generates cells which can cause tumor regression.

Cytokine Production

Interferon γ (IFNγ), tumor necrosis factor α (TNFα), and IL-2 are cytokines associated with cell-mediated immune responses that direct the expansion and activation of NK cells and lymphokine activated killer (LAK) cells and the expansion of CD8+ CTL. Such effector cells are likely to have particular relevance to the elimination of tumors since animals lacking these effector cell types do not efficiently eliminate tumors or metastases [Whiteside et al. (1994) Clin. Immunother. 1:56].

Lymphocytes isolated from the PBL and tumor reconstituted mice are co-cultured with autologous untransduced or mock-transduced and IMG expressing tumor cells are assayed for the production of cytokines associated with cell-mediated immunity. Secretion of IFNγ, TNFα and IL-2 into the culture supernatants at various times during co-culture are assayed by sandwich ELISA [Sad et al. (1995) Immunity 2:271].

In Vitro CTL Assay

Viable cells are harvested and enumerated from co-cultures of lymphocytes with autologous tumor cells (mock transduced or expressing IMGs) after 5 days of culture or after multiple weekly stimulations (as described above). Untransduced autologous tumor cells are labelled with $^{51}$NaChromate and standard 5 hour $^{51}$Cr-release assays are performed. Lysis of autologous and allogenic tumor targets are compared to the original stimulating cells. Lysis of tumor cells matching those used as the original stimulus, but not of other tumor cells, indicates the lysis is likely antigen specific. Proof of antigen specific lysis is made by the ability to block lysis using antibodies to class I MHC molecules and the ability to eliminate the effector cell responsible for lysis through the use of anti-CD8 and complement. non-MHC restricted lysis may indicate the induction of LAK cells.

In Vitro NK/LAK Assay

Some tumor cells escape immune T cell recognition and elimination in vivo by down-regulating the expression of MHC molecules, particularly class I MHC proteins [Rivoltini et al. (1995) Cancer Res. 55:3149]. However, unlike CD8+ CTL, fresh NK cells and IL-2 expanded NK cells (LAK) do not require MHC molecules for their recognition and lysis of target cells [Lanier and Phillips (1988) ISI Atlas of Science, pp. 15–29]. NK/LAK cells may therefore serve to eliminate cells expressing altered or reduced levels of class I molecules that normally escape CD8+ T cell surveillance.

Five hour $^{51}$Cr release assays are used to determine which primary (or established) tumors are NK sensitive. Co-culture of autologous PBLs or immune cells isolated from PBL and tumor reconstituted SCID/bg mice are conducted using mock transduced or IMG expressing tumors to determine whether this results in augmented NK/LAK (non MHC) restricted cytolytic activity that includes the stimulating tumor target if initially observed, or the induction of substantial NK/LAK activity when none was present (against the tumor target) in the initial assay.

EXAMPLE 13

Delivery Of Immune-Modulating Genes To Human Tumors

Immune-modulating genes may be delivered to human tumor cells in vivo and ex vivo by a variety of means.

a) Retroviral Transduction

Retroviral vectors encoding immune-modulating proteins may be used to introduce IMGs into established or primary tumor cells as described in Exs. 2, 6 and 7. The transfer of IMGs using retroviruses may be made more efficient by increasing the titer of the virus encoding the IMG(s) and increasing the transduction efficiency. To increase the virus titer, single cell clones from the producer PA317 cells are be selected by growth in the presence of G418 (or selective medium suitable for the selectable marker carried on the retroviral construct) and clones producing the highest titers of virus are be expanded. To increase the titer of the producer cell line further, the PA317 cells can be reinfected with ecotropic virus [e.g., virus produced in GPE-86 packaging cells] and the best producer cell clones can be selected. To improve the transduction efficiency, retrovirus are used in combination with liposomes or poly-L-ornithine or polylysine to enhance virus uptake.

Another way to improve gene transfer efficiency using retroviruses is to increase the targeting efficiency. Many tumor cells including glioblastomas and melanomas express excess levels of the transferrin receptor. Transferrin has been used to increase the transduction efficiency of adenovirus in combination with polylysine [Lozier et al. (1994) Human Gene Ther. 5:313]. Several recent reports demonstrated that replacing the SU (surface) domain of the env gene of a retrovirus can increase receptor-mediated transduction efficiency [Kasahara et al. (1994) Science 266:1373; Cosset et al. (1995) J. Virol. 69:6314; Dong et al. (1992) J. Virol. 66:7374; and Chu and Dornburg (1995) J. Virol. 69:2659]. The human transferrin gene is 2097 bp long (coding region provided in SEQ ID NO:25). Insertion of such a long sequence into the SU domain of the env gene of MLV vector may not produce a stable Env product.

However, earlier studies have suggested that the modified Env fusion protein requires the native Env for stable assembly and efficient entry. Thus, the transferrin-env fusion gene is co-transfected with the native env gene to produce retrovirus particle bearing a mixture of wild type and recombinant Env. The gene transfer efficiency of the new vector is examined by transducing glioblastomas or melanomas expressing high levels of transferrin receptor.

b) Recombinant Adenoviral Vectors

Recombinant adenoviruses can accommodate relatively large segments of foreign DNA (~7 kb), and have the advantage of a broad host cell range and high titer virus production [Graham and Prevec (1991) Meth. Mol. Biol. 7:109–128]. Adenoviruses have been used in vivo in rats to efficiently deliver genes to the liver and the pancreatic islets [reviewed in Becker et al. (1994) In *Protein Expression in Animal Cells*, Roth et al. eds.] and to the central nervous system [Davidson et al. (1993) Nature Genet. 3:219]. Rat livers have also been efficiently transduced ex vivo and then re-implanted [Shaked et al. (1994) Transplantation 57:1508].

The replication defective recombinant adenoviruses are employed; these viruses contain a deletion of the key immediate early genes E1a and E1b (Graham and Prevec, supra). To generate and propagate recombinant viruses, a packaging cell line such as 293 cells which supply the E1a and E2a proteins in trans is employed. Recombinant adenoviruses are created by making use of intracellular recombination between a much larger plasmid encoding most of the viral genome and a small plasmid containing the gene of interest (e.g., a cytokine) bracketed by regions of homology with the viral integration site. Recombinant adenoviruses expressing mouse IL-4 and IL-10, both under the control of a CMV immediate early enhancer promoter, have been constructed. Recombinant adenoviruses expressing human B7-2 and GM-CSF as well as a second virus expressing both the IL-12A and IL-12B subunits are constructed. The DNA constructs are cloned as bi-cistronic units with IRES as described in Ex. 1.

Standard methods are used to construct the recombinant adenoviruses (Graham and Prevec, supra and Becker et al., supra). Briefly, each plasmid is co-transfected together with pJM17 (Microbix Systems, Toronto) into sub-confluent monolayers of 293 cells (ATCC CRL 1573) using calcium phosphate precipitation and a glycerol shock. Initial recombinant viral stocks are titered on monolayers of 293 cells, and isolated single plaques are obtained and tested for cytokine expression using an ELISA. Viral stocks are amplified and titered on 293 cells, and stored in aliquots at −70° C.; if necessary, stocks are concentrated by centrifugation on density gradients. To infect tumor cells with recombinant adenoviruses, freshly isolated tumor cells are mixed with adenoviral stocks in a minimal volume. Titers of stocks are typically $10^5$–$10^8$/ml. Medium is replaced after several hours and the cells are followed for expression of the recombinant adenoviral-encoded IMGs and/or reporter genes.

A potential drawback of using a adenoviral delivery system is that the transduced cells may retain or express small quantities of adenoviral antigens on their surface [Yang et al. (1994) Nature Genet. 7:362]. "Second generation" adenoviral vectors which contain deletions in the E2a gene are available and are associated with less inflammation in the recipient and a longer period of expression of the gene of interest [Yang et al., supra and Engelhardt et al. (1994) Proc. Natl. Acad. Sci. USA 91:6196]. If necessary, IMGs are inserted into second generation adenoviral vectors. However, since the transduced tumor cells are lethally irradiated before injection into the recipient and since other manipulations are undertaken to induce the tumor cells to secrete immune-stimulating cytokines and to express surface signalling molecules, the expression of small quantities of adenoviral proteins (when first generation vectors are employed) may provide a desirable adjuvant effect. Furthermore, the recipient is subsequently boosted with retrovirally transduced tumor cells (which express the cytokines and tumor antigens, but not the adenoviral antigens). The recipient is monitored for tumor-specific immune responses at a secondary distant site where non-transduced tumor is implanted; the generation of such a response indicates that the desired tumor-specific immunity has been achieved.

c) Targeted Cationic Liposomes

Cationic liposomes have proven to be a safe and effective means for inducing the transient expression of DNA in target cells [Ledley (1995) Human Gene Ther. 6:1129; Feigner (1990) Adv. Drug Delivery Rev. 5:167; Feigner et al. (1987) Proc. Natl. Acad. Sci. USA 84:7413; and Smith et al. (1993) Biochim. Biophys. Acta 1154:327]. Clinical trails are underway using cationic liposomes to introduce the CFTR gene into the lungs of cystic fibrosis patients [Caplen et al. (1994) Gene Ther. 1:139 and Alton et al. (1993) Nature Genet. 5:135] or to introduce, by direct intra-tumor injection, the T cell costimulator B7-1 into malignant melanoma lesions in order to induce a cell-mediated immune response [Nabel et al. (1993) Proc. Natl. Acad. Sci. USA 90:11307].

Cationic liposomes (e.g., DOTAP/DOPE) and ligand-targeted cationic liposomes are employed for the delivery of IMGs to tumor cells. Ligand-targeted liposomes are made by covalently attaching ligands or antibodies to the surface of the cationic liposome. When glioblastoma cells are to be targeted, transferrin is used as the ligand as glioblastoma cells express high levels of the transferrin receptor on their surface. When melanoma cells are to be targeted, internalizing receptors, monoclonal antibodies directed against melanoma-specific surface antigens (e.g., mAb HMSA5) are employed as the ligand.

Plasmid DNA encoding IMGs (e.g., B7-2, GM-CSF and IL-12) is formed into a complex with preformed cationic liposomes using standard methodology or alternatively the DNA is encapsulated into the liposome interior. The DNA-containing liposomes are then used to transfer the DNA to tumor cells in vivo by direct intra-tumor injection or in vitro (using freshly explanted tumor cells) followed by return of the transduced cells to the recipient (e.g., a patient).

d) Gene Transfer Using Biolistics

Biolistics (microballistics) is a method of delivery DNA into cells by projection of DNA-coated particles into cells or tissues. DNA is coated onto the surface of tiny (~1–3 μm diameter) gold or tungsten microparticles and these particles are accelerated to high velocity and are impacted onto the target cells. The particles burst through the cell membrane and lodge within the target cell. The cell membrane quickly reseals and the passenger DNA elutes off of the particle and is expressed. The biolistic method has been used to transfect mammalian cells [Williams et al. (1991) Proc. Natl. Acad. Sci. USA 88:2726; Tang et al. (1992) Nature 356:152; Sanford et al. (1993) Methods Enzymol. 217:483].

A hand-held biolistic apparatus (BioRad) is used to transfer DNA into tumor cells or isolated tumor fragments. This device uses compressed helium to drive a disc-shaped macroprojectile which carries on its surface microparticles of gold (1–5 μm) of gold which have been coated with purified plasmid DNA (coprecipitated with spermine) (Williams et al., supra). This apparatus has been used to successfully transfect primary tissues.

Plasmid DNA encoding the IMGs is coated onto the surface of gold microparticles according to the manufacturer's instructions (BioRad) and the biolistic apparatus is used to transfer the DNA into freshly explanted tumor cells or directly into exposed tumors (e.g., metastatic nodules on the surface of the liver, melanoma lesions on the skin).

EXAMPLE 14

Further Characterization of Human PBL Reconstituted SCID/beige And SCID/nod Mice This example provides additional characterization of the reconstituted SCID/nod and SCID/beige mice described in Examples 3 and 11 above.

To study the efficiency of human immune cell reconstitution in scid mice, SCID/nod and SCID/beige mice were reconstituted with PBLs of different donors as described in Ex. 3. Analyses of human Ig levels at 2, or 4–7 weeks after reconstitution showed that both of these strains of mice were capable of producing human Igs at levels averaging 500–600 µg/ml; Ig levels were assessed by ELISA (Ex. 3). Approximately half of the SCID/nod mice used in the reconstitution study did not produce detectable amount of human Igs.

The percentages of human lymphocytes present in different organ compartments of the reconstituted mice were determined two months after reconstitution. As described in Ex. 11, cells were harvested from peritoneal cavity (P.W. or peritoneal wash), spleen (Splenocytes or S.P.), and peripheral blood (PBL), and analyzed by flow cytometry using antibodies against the human leukocyte surface marker CD45. The results are summarized in FIGS. 6A and 6B.

Figure 6A:
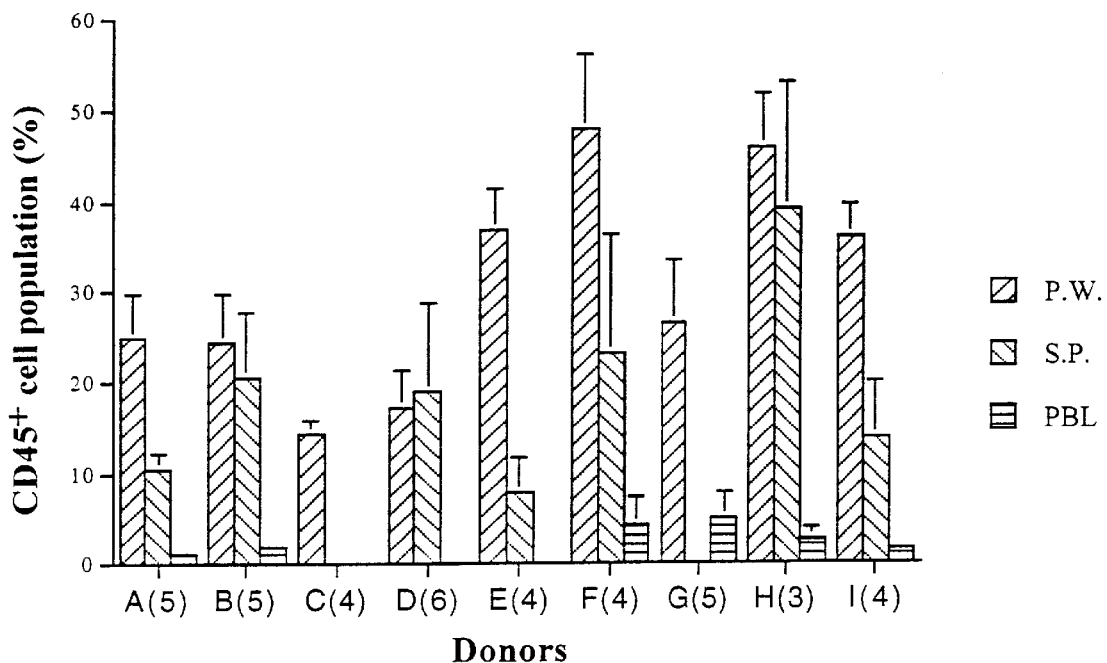
FIGS. 6A and 6B show the percentage of CD45+ lymphocytes in reconstituted SCID/bg and SCID/nod mice, respectively.
Figure 6B:
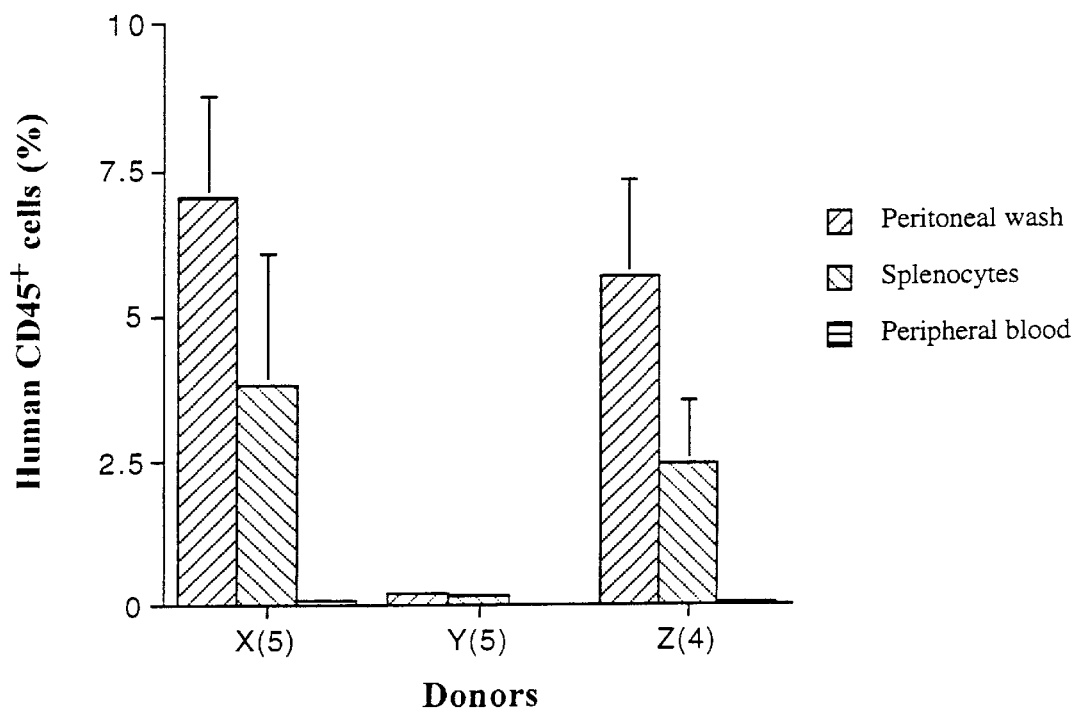

The results shown in FIG. 6A indicated that SCID/beige mice were consistently reconstituted with human PBLs in all three organ compartments with little variation among donors (donors A–I; the numbers in the brackets by the donor designation indicates the number of animals reconstituted with donor PBLs). In contrast, the overall reconstitution efficiency in the SCId/nod mice was low, i.e., <10% in the peritoneal cavity, <5% in the spleen, and almost undetectable in the peripheral blood (FIG. 6B; donors X–Z). Donor-to-donor variation was also more pronounced in the SCID/nod mice. For this reason, as well as the reasons discussed in Ex. 3, reconstituted SCID/bg mice are preferred for vaccination/challenge experiments (i.e., evaluation of candidate vaccines).

EXAMPLE 15

Anti-HIV Immunity Cannot Be Assessed By In Vitro Assays

The time course of disease progression after HIV infection varies depending on a number of factors including viral strains and host immune responses. While the majority of HIV-infected subjects develop AIDS at a median of ≈10 years, up to 5–10% of infected individuals do not appear to have clinical symptoms even after 10 years [Haynes et al. (1996) Science 271:324 and Baltimore (1995) N. Engl. J. Med. 332:259]. Indeed, epidemiological evidence suggests that some individuals may be resistant to infection by HIV; despite multiple high-risk exposures, these individuals remain HIV negative [Detels et al. (1994) J. Acquired Immune Defic. Syndr. 7:1263 and Taylor (1994) J. NIH Res. 6:29].

Both host genetic factors and the infection-immunization process following HIV exposure may play roles in the development of protective immunity. The mechanism of resistance to HIV infection in the HIV-exposed but uninfected individuals may be associated with HIV-specific cytotoxic T cell activity, a switch from Th2 to Th1 cytokine response, genetic loci linked to HLA, transporter associated with antigen processing (TAP), and HIV coreceptors, or development of anti-HLA antibodies. While strong indirect evidence supports the hypothesis that these exposed but uninfected individuals have protective immunity against HIV infection, direct in vivo experiments attesting to this hypothesis are still lacking. Understanding the mechanism of such protective immunity is necessary for to the design and testing of effective prophylactic vaccines and immunotherapeutic regimens.

a) The PBLs from High Risk Individuals Are Susceptible to HIV Infection In Tissue Culture To determine if lymphocytes from high risk (HR) individuals were susceptible to HIV-1 infection, their PBLs were collected, activated with PHA in culture and then incubated with T cell or macrophage tropic HIV-1. Infection was scored on the basis of HIV-1 RT activity and immunohistochemical staining with AIDS patients' sera.

i) Study Subjects

Two individuals were identified who have engaged in regular unprotected heterosexual or homosexual intercourse with HIV-positive partners over a period of up to 10 years, but have remained HIV negative as determined by repeated serological assay, polymerase chain reaction (PCR) and PBL cocultivation. High-risk (HR) donor 1 is the heterosexual partner of a bisexual individual who had a CD4 count of 400–500/µl at the time of positive HIV diagnosis in July 1992. An estimated 144 episodes of vaginal intercourse between the HR donor 1 and the partner took place before his diagnosis, and the HIV-positive partner's CD4 count has decreased to 30/µl at the time of study. HR donor 2 is the homosexual partner of an individual known to be HIV-1 positive since 1986 and whose CD4 count remained in the 300–400/µl range. It was estimated that unprotected anal sex took place ≈225 times before this study, and unprotected sexual contact has "continued" since diagnosis. Infectious virus had been isolated from phytohemagglutinin (PHA)-blasted PBLs of both HIV-positive partners. These two HR subjects who participated in the hu-PBL-SCID mouse challenge study described below do not share common HLA haplotypes. Additional multiply exposed, uninfected individuals who fit into the above criteria were also included in the in vitro studies. Blood provided by Canadian Red Cross and volunteers in the laboratory with no prior HR exposures to HIV were the source of control PBLs.

ii) Virus Preparation

HIV-1 strains used in this study include laboratory-established T cell tropic ($HIV_{NL4-3}$) and macrophage tropic HIV-1 ($HIV_{NLADS}$ also referred to as $HIV_{ADA}$) [Adachi et al. (1986) J. Virol. 59:284]. $HIV_{NL4-3}$ and $HIV_{NLADS}$ are available as catalog no. 78 and no. 416, respectively from the NIH AIDS Research and Reference Reagent Program of National Institutes of Health, Bethesda, Md. and the sequence of pNL4-3, a plasmid containing a proviral form of $HIV_{NL4-3}$ is available in the GenBank database under accession number M19921. Virus stocks were prepared from infected peripheral blood mononuclear cells or macrophages as described [Chang and Zhang (1995) Virol. 211:157]. Briefly, macrophage cultures were prepared from HIV-seronegative donors by adherence of PBLs to plastic flasks as described previously with minor modifications [Hassan et al. (1986) J. Immunol. Methods 95:273]. PBLs were prepared by density gradient separation using lymphocyte separation medium (Organon Teknika Corp., Durham, N.C.). The PBLs were resuspended in RPMI 1640 medium supplemented with 20% heat-inactivated human serum. Approximately $5 \times 10^7$ PBLs were attached to a T-75 flask and incubated overnight at 37° C. The next day cells were washed three times with PBS and the attached cells were incubated with 0.02% EDTA in PBS for 5–10 min. The cells were collected with a cell scraper and plated onto a 48-well plate at 5×10⁴ cells per well. The viability approached 100% as determined by trypan blue staining. The initial monocytes were characterized by Wright's staining and the mature macrophages by both Wright's staining and microscopic examination.

HIV virus stocks were prepared by transfecting HeLa cells or by infecting human PBLs, CD4+ lymphocytes (T cell or macrophage tropic viruses) or macrophages (macrophage tropic viruses); infections may be performed using an moi of about 0.2. After transfection, culture media was collected 48 hr later and frozen in aliquots at −80° C. After infection, HIV RT kinetics were followed and virus was harvested at the peak of RT production. Virus aliquots were examined by RT assay and TCID50 assay.

The same virus stocks were used for both in vitro and in vivo experiments. The multiplicity of infection (moi) or tissue culture infectious dose ($TCID_{50}$) was determined by serial dilution of virus stock on HIV-1 negative, PHA-stimulated PBLs as described previously [Chang and Zhang, supra and Ho et al. (1989) N. Engl. J. Med. 321:1621]. Briefly, PBLs from HIV-seronegative donors were stimulated with 0.25 μg/ml PHA for 3 days prior to infection and then maintained in RPMI 1640 supplemented with 10% FBS and 10% interleukin-2 (Pharmacia). PBLs were plated in 48 well plates at 0.5 million per well and infected with serially diluted virus supernatants in duplicate. Culture supernatants were harvested every 3–4 days. At approximately 3–4 weeks of time, infection kinetics was determined. The dilution point that gave 50% of positive infection (one out of two wells) was considered to be the TCID50 point.

iii) In Vitro HIV-1 Infection

Heparinized peripheral blood was collected from HR and low-risk (LR) HIV-negative donors. PBLs were separated by gradient centrifugation with Histopaque (Sigma). Infection was performed as described previously (Chang and Zhang, supra). Briefly, PBLs were treated with PHA (5 μg/ml, Sigma) and infected with T cell or macrophage tropic HIV-1 at 0.2 moi. The culture was split at a 1:3 ratio every 3–4 days. The supernatant was harvested for reverse transcriptase (RT) assay, and infections were also confirmed by immunohistochemical staining as described (Chang and Zhang, supra). Briefly, adherent cells were washed with PBS three times, fixed in cold acetone and methanol (1:1) for 2 min, washed three times in PBS, and incubated in blocking solution (20% FBS, 0.1% TritonX100 in PBS) for 30 min. Non-adherent cells were attached to the surface of a 24-well plate which had been pretreated with poly-D-lysine (1 mg/ml, Sigma) at room temperature for 10 min. An HIV patient serum which was diluted at 1:2000 in a blocking solution containing 20% FBS, 0.1% TritonX100 and 2% dry milk in PBS was used as the first antibody and the incubation was done at room temperature for 1 hr or at 4° C. overnight with constant shaking. After being washed in PBS for 5 min 4 times, the cells were incubated with a 1:200 dilution of normal sheep antisera at room temperature for 30 min to block non-specific signals. The secondary antibody was a biotinylated sheep anti-human antibody (Amersham) which was used at 1:2000 dilution and incubated at room temperature for 1 hr. The cells were washed four times in PBS-Tween 20 (0.3%) and incubated in the ultra-sensitive ABC staining solution (containing avidin and biotinylated horseradish peroxidase, Pierce Chemical Co.) at room temperature for 30 min. After four more washes in PBS-Tween 20, the cells were incubated in 3, 3'-Diaminobenzidine tetrahydrochloride (DAB) solution (Sigma) containing 0.3% $NiCl_2$ for 2–3 min. The reaction was stopped by washing cells with tap water for 1–2 min. Cell staining was scored under an inverted microscope and photographed. To reduce background staining, both the primary and the secondary antisera were preabsorbed with fixed human PBLs. Pretreatment of fixed cells with 0.01% $H_2O_2$ at room temperature for 5 min essentially eliminated all nonspecific background signals. The percentages of positive cells were determined by taking the average of more than three representative counts of 1,000 or 10,000 cells.

iv) RT Assay

Reverse transcriptase levels were measured as follows. A 10 μl sample of culture medium (supernatant) was incubated with 50 μl of a reaction cocktail containing 50 mM Tris-HCl, pH 8.3, 20 mM DTT, 0.6 mM $MnCl_2$, 60 mM NaCl, 0.05% NP40, 5 μg/ml of oligodeoxythymidilic acid, 10 μg/ml of polyriboadenylic acid and 10 μM of [α-$^{32}$P]dTTP (DuPont NEN, specific activity 800 Ci/mmol). The reaction was incubated at 37° C. for 1 hr. A 3 μl aliquot was then spotted onto DE-81 paper (Whatman), and air dried. The DE-81 paper was washed 3 times in 2×SSC (20×SSC comprises: 3 M NaCl, 0.3 M sodium citrate, pH 7.0) and autoradiographed.

v) Immunohistochemical Staining and Fluorescence-Activated Cell Sorter (FACS) Analysis Immunohistochemical staining was performed as described in section iii above. For FACS analysis, red blood cells were lysed with ammonium chloride solution [containing 9 ml of 0.16 M $NH_4Cl$ and 1 ml of 0.17 M Tris (pH 7.62 to final pH 7.2)]. The cells were stained with PE-anti-mouse-H-2K$^d$ (Pharmingen), fluorescein isothiocyanate (FITC)-anti-human-CD45 (anti-HLe-1, Becton Dickinson), phycoerythrin-anti-human-CD4 or FITC-anti-human CD8 (Becton Dickinson) for 30 min on ice followed by three washes with immunostaining buffer (PBS containing 0.1% FBS, 0.02% $NaN_3$). Isotype-matched PE- and FITC-mouse Igs were used for control staining. The samples were analyzed using the LYSIS II program on a FACScan (Becton Dickinson).

vi) PBLs From High Risk Donors Are Susceptible To HIV Infection In Vitro

Figure 7A:
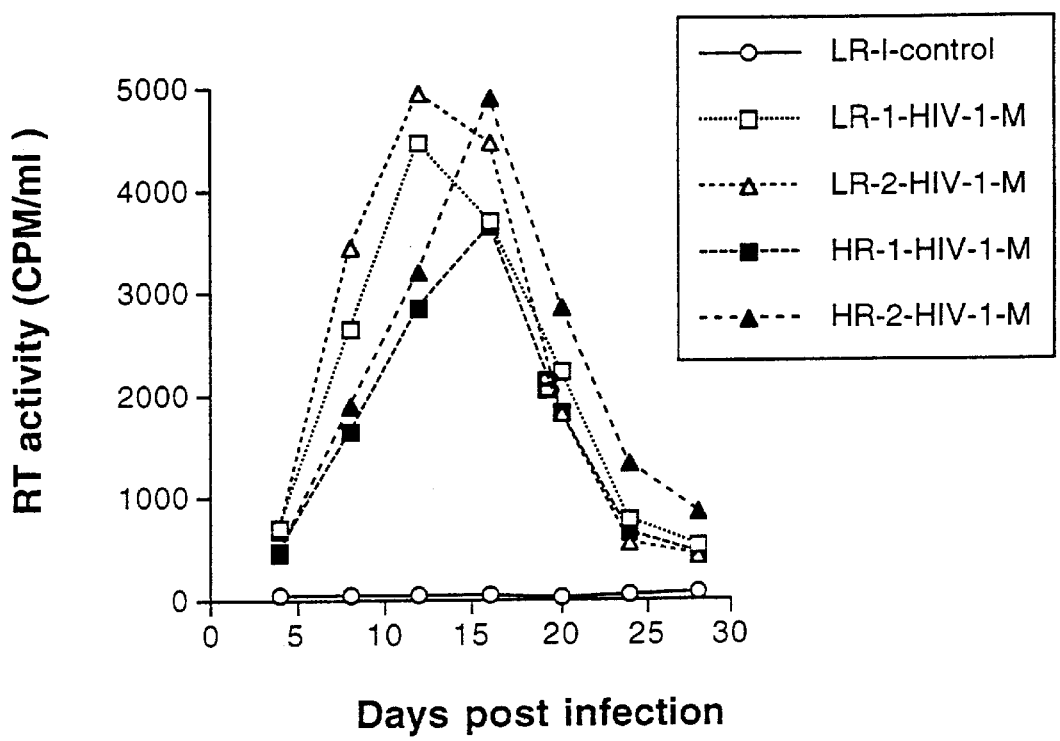
FIGS. 7A and 7B show RT activity in infected PBLs from LR and HR seronegative individuals using a macrophage tropic HIV at an moi of 0.2 (7A) or at an moi of 0.001–0.0001 (7B), respectively.

As shown in FIG. 7a, the RT assay demonstrated that PBLs from these two HR, HIV-1-seronegative individuals were as susceptible as PBLs from normal LR donors to HIV-1 infection in tissue culture (FIG. 7a). In FIG. 7a, the RT activity (CPM/μl) is plotted against days post infection. The RT activity in PBLs from two LR individuals (LR-1 and LR-2) infected with the macrophage tropic HIV$_{NLADS}$ ("HIV-1-M") at 0.2 moi is shown using open squares and triangles, respectively; RT activity in uninfected PBLs from LR-1 is shown using the open circles ("LR-1-control"). The RT activity in PBLs from two HR individuals (HR-1 and HR-2) infected with HIV$_{NLADS}$ at 0.2 moi is shown using solid squares and triangles, respectively. Similar results were obtained with the T-cell tropic strain HIV-1$_{NL4-3}$. The immunostaining results confirmed the RT assay results.

Figure 7B:
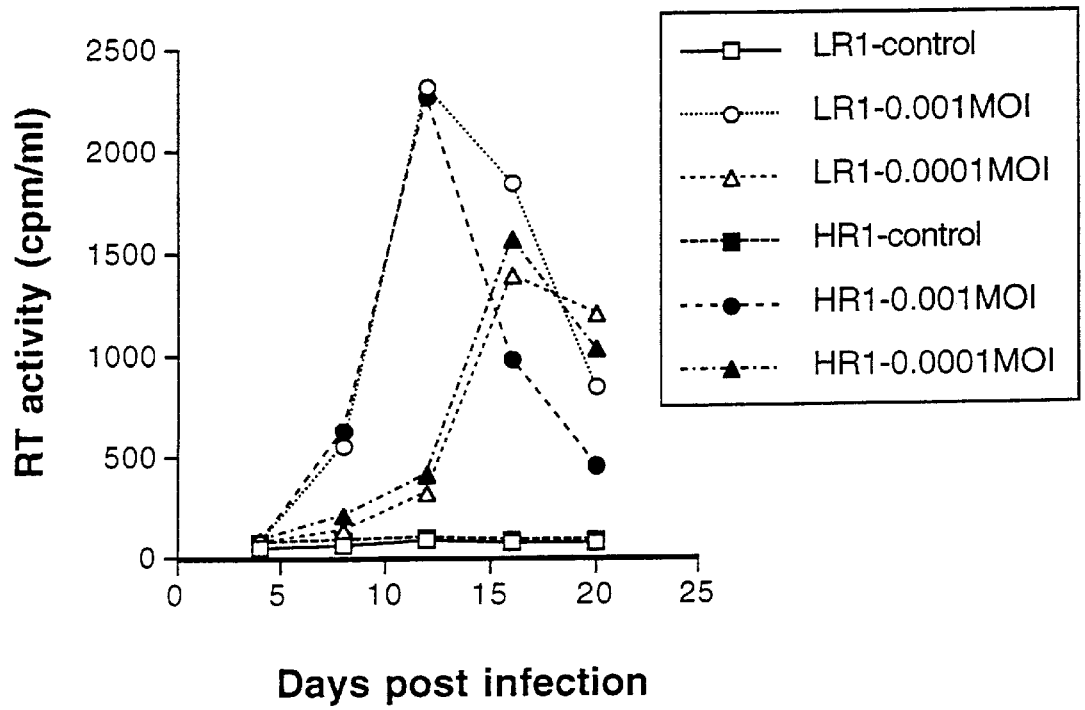

To further examine whether the HR individuals' PBLs were somewhat resistant to HIV-1 infection, the tissue culture infection was performed using a series of diluted virus preparations (from moi of 10$^{-1}$ to 10$^{-4}$). The results are summarized in FIG. 7b. In FIG. 7b, the RT activity (CPM/μl) is plotted against days post infection. The open circles show RT activity in uninfected PBLs from LR-1; the open squares and triangles show RT activity in PBLs from LR-1 infected with HIV-1$_{NL4-3}$ at a moi of 0.001 and 0.0001, respectively. The solid circles show RT activity in uninfected PBLs from HR-1; the solid squares and triangles show RT activity in PBLs from HR-1 infected with HIV-1$_{NL4-3}$ at a moi of 0.001 and 0.0001, respectively. These results showed that even with a moi of $10^{-4}$, the HR donors' PBLs were still infected. A comparable dose-dependent kinetics of infection with different concentrations of virus was observed between LR and HR individuals. Similar results have been reported for HR, HIV-1-seronegative hemophiliacs [Lederman et al. (1995) J. Inf. Dis. 172:228]. However, little is known about the possible nature of the protective immunity in these individuals.

EXAMPLE 16

HIV-1 Exposed-but-Uninfected Individuals Are Resistant to HIV-1 Infection In Vivo To overcome the problem of the lack of an existing in vivo HIV-1 infection model, the human PBL-reconstituted severe combined immunodeficiency mouse model (hu-PBL-SCID) described in Exs. 3, 11 and 14 was used to investigate the nature of the protective immunity in the HIV-exposed but uninfected individuals. This in vivo model was used to test the susceptibility of the two HR, HIV-negative individuals to HIV-1 infection. PBLs were isolated and cells from each donor were used to reconstitute 6–7 SCID/bg mice each time as described in Ex. 3. Two weeks after reconstitution, the hu-PBL-SCID/bg mice were challenged with T cell or macrophage tropic HIV-1 using a $TCID_{50}$ of 100 by IP injection under metofane-induced anesthesia. Two weeks after HIV-1 challenge, mice were killed, and single cell suspensions were prepared from peritoneal lavage, spleen, and peripheral blood and processed for immunostaining, flow cytometry analysis, and PCR. All experiments were performed in a biosafety level 3 facility and protocols were approved by the Biosafety Committee, Research Ethics Board, and Health Sciences Animal Welfare Committee at the University of Alberta.

Figure 8A:
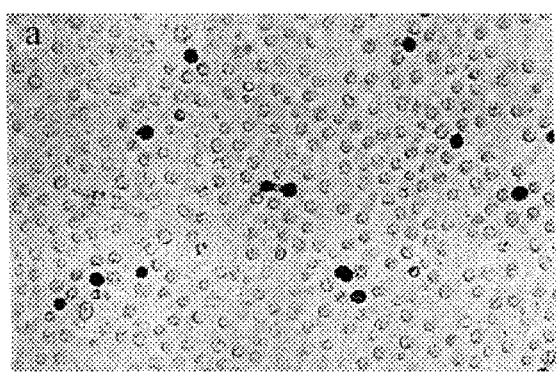
FIGS. 8A–8E demonstrate the in vivo infection of hu-PBL-SCID/bg mice.
Figure 8B:
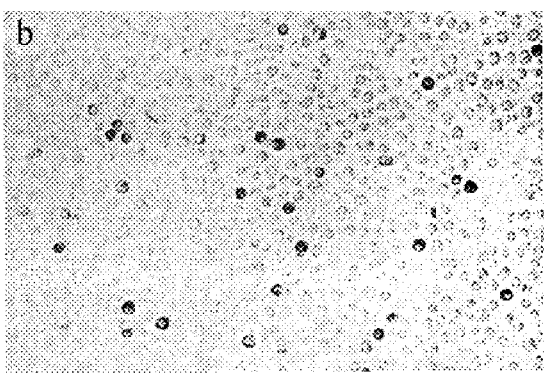
Figure 8C:
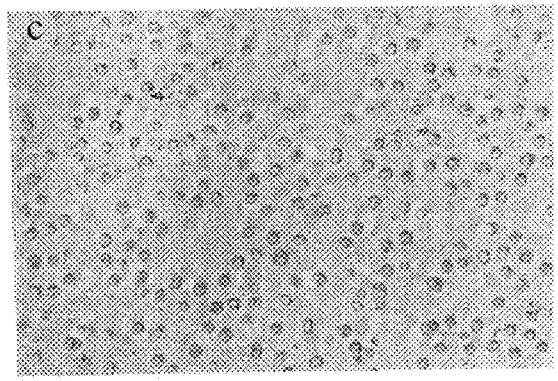
Figure 8D:
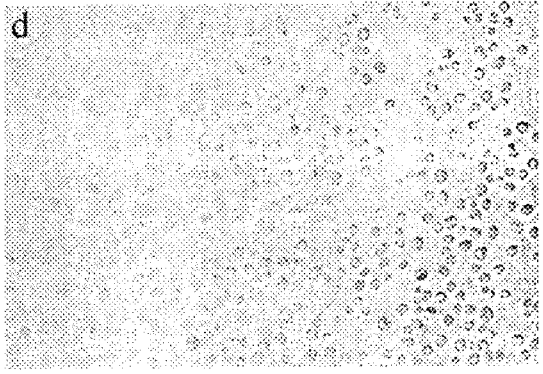

The cells harvested from the infected reconstituted mice were analyzed by flow cytometry using anti-mouse major histocompatibility complex class I antibody ($H-2K^d$) and anti-human CD45, CD3, CD4, and CD8 antibodies as described in Ex. 11. At the same time, HIV-1 infection was examined by a sensitive single-cell immunohistochemical staining method using either HIV-positive patients' sera or a monoclonal anti-p24 antibody as described in Ex. 15. Representative immunostaining results are shown in FIG. 8. For the results shown in FIG. 8, all mice were killed 4 weeks after reconstitution and single cell suspensions were prepared from the three different organ compartments for immunostaining. FIGS. 8a and 8b show HIV-1-positive immunostaining of peritoneal lavage and splenocytes, respectively, of mice reconstituted from a LR individual. FIGS. 8c and 8d show HIV-1-negative immunostaining of peritoneal lavage and splenocytes, respectively, of mice reconstituted from a HR individual.

Figure 8E:
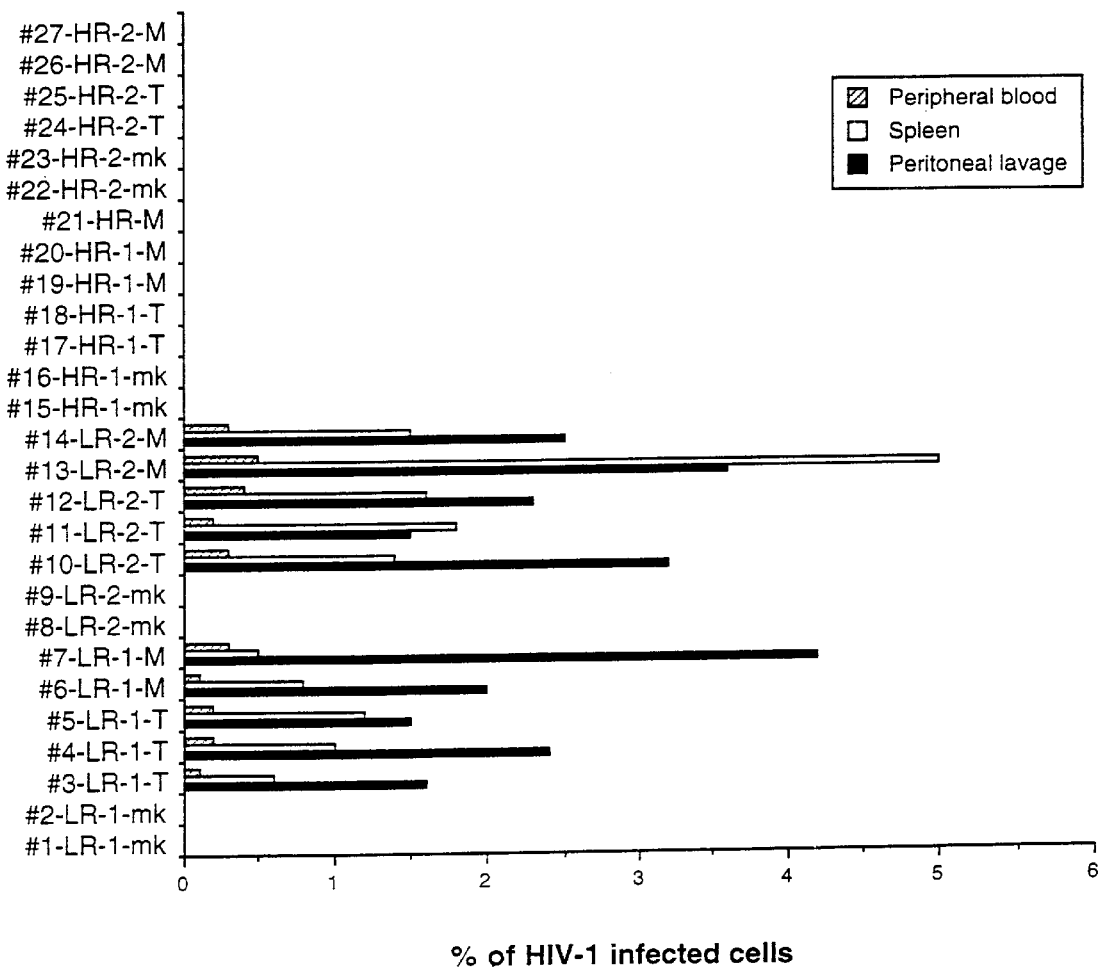

The results of immunostaining demonstrated that all of the 10 hu-PBL-SCID/bg mice reconstituted with PBLs from control individuals were infected by either T cell or macrophage tropic HIV-1, at frequencies of about 1–4% of cells from the peritoneal lavage (FIG. 8a), 0.8–5% of splenocytes (FIG. 8b), and 0.1–0.5% of peripheral blood mononuclear cells. In contrast, all nine mice reconstituted with PBLs from the two HR, HIV-uninfected individuals were negative for the HIV immunostaining (FIG. 8c and 8d, peritoneal lavage and spleen, respectively), but one of the negative mice was positive in the spleen for HIV-1 DNA sequences by PCR analysis, suggesting that infection was established at the time of challenge. These results are summarized in FIG. 8e. In FIG. 8e, the solid, hatched and shaded bars represent cells from peritoneal lavage, spleen and peripheral blood, respectively. Reconstitution of mice with PBLs from the LR-1 donor (#1–7), the LR-2 donor (#8–14), the HR-1 donor (#15–21) and the HR-2 donor (#22–27) were confirmed by ELISA for human Ig and FACS analysis for the human CD45 leuckocyte marker. In FIG. 8e, "M-tropic" indicates infection with the macrophage tropic $HIV_{NLADB}$ and "T-tropic" indicates infection with the T-cell tropic $HIV_{NL4-3}$. The in vivo challenge experiments were repeated once with eight mice reconstituted for each donors' PBLs and similar results were obtained.

EXAMPLE 17

Cell-Mediated Immune Responses In HR Individuals

To investigate if the in vivo protection is due at least in part to HIV-1-specific, cell-mediated immune responses in the HR, seronegative individuals, a convenient and very sensitive ELISPOT assay was modified to determine the fraction of IFN-γ producing cells after HIV antigen presentation. IFN-γ is produced by T cells and natural killer cells activated by antigens and is the key mediator of $CD4^+$ Th1 cell development [Wenner et al (1996) J. Immunol. 156:1442].

a) ELISPOT Analysis of IFN-γ Production

ELISPOT was performed as described [Miyahira et al. (1995) J. Immunol. Methods 181:45] with the following modifications. To quantify the IFN-γ producing cells, a 96-well nitrocellulose-bottomed plate (Multiscreen-HA, Millipore) was coated with 75 μl per well mouse anti-human IFN-γ (10 μg/ml, Pharmingen) at room temperature overnight. HIV-1-infected PBLs were used as stimulators in the ELISPOT assay. Infection was confirmed by RT assay and by immunohistochemical staining (ranged 3–5% of HIV-1-positive). No difference was observed between HR and LR individuals in either RT or HIV antigen expression in the infected PBLs. HIV-1-infected PBLs were treated with mitomycin C (5 μg/ml) for 2.5 hr, washed, and resuspended in RPMI medium 1640 containing 10% FBS and 20 units/ml interleukin 2 (Boehringer Mannheim), and seeded in the anti-IFN-γ-coated 96-well plate at $1 \times 10^5$ per well as target cells (T). Frozen unstimulated autologous PBLs, which were thawed and used as effector cells (E), were added to the wells at E/T ratio of 0.4:1, 2:1, and 10:1 in triplicates, and incubated in RPMI medium 1640 containing 10% FBS and 20 units/ml IL-2 at 37° C., 95% $O_2$/5% $CO_2$ for 24 hr.

After overnight incubation, the wells were washed four times using PBS-Tween 20 (PBS-T, 0.05%), blocked with 20% FBS in PBS-T at room temperature for 15 min, and incubated with 100 μl of biotinylated-mouse-anti-human IFN-γ (Pharmingen, 2.5 μg/ml in PBS-T) at 4° C. overnight. Each well was then washed four times using PBS-T and incubated with peroxidase-labeled streptavidin (Caltag, South San Francisco, Calif.) in PBS/T at room temperature for 1 hr. IFN-γ-producing cells were detected as purple brown spouts after DAB (Sigma) and 0.3% $NiCl_2$ staining. The wells washed four times with double distilled $H_2O$ and air-dried, and were the number of IFN-γ producing cells was counted using a video-imaging (Appligene, Strasbourg, France), and computer analysis system. Control samples were prepared using the same effector cells plus autologous PBLs that were not infected with HIV-1.

b) PBLs From HR Donors, But Not LR Donors, Contain HIV-Specific Responders

Figure 9:
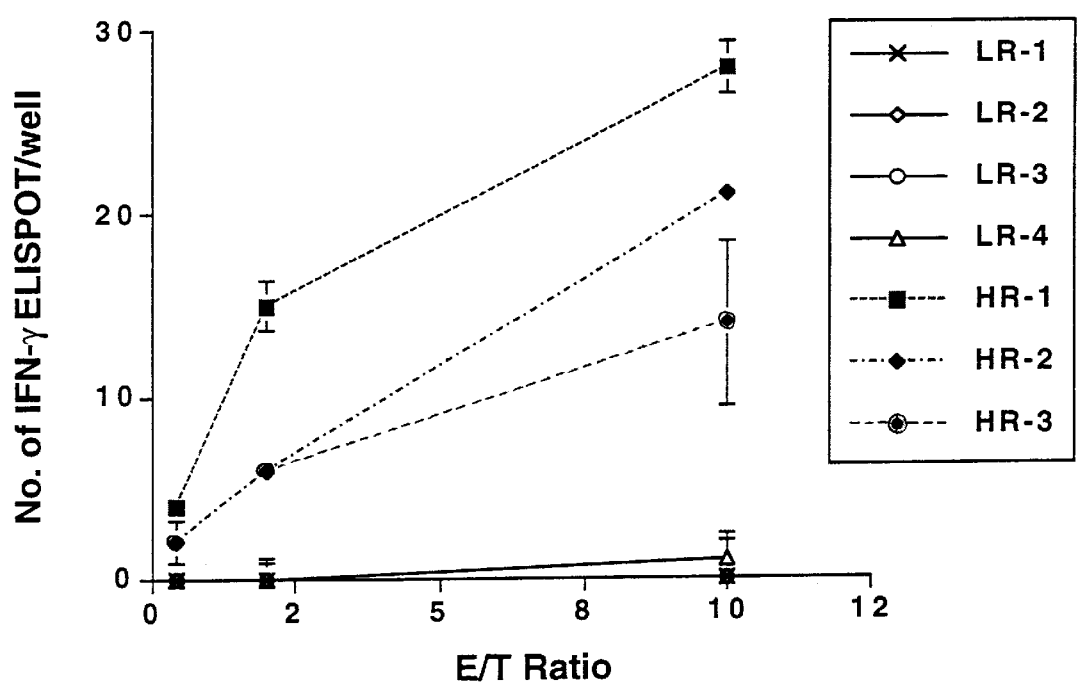
FIG. 9 shows an ELISPOT analysis of HIV-1-specific IFN-γ production in PBLs of HR and LR uninfected individuals.

Four LR and three HR donors' PBLs, unstimulated, were incubated with mitomycin C-treated, HIV-infected autologous PBLs in a 96-well nitrocellulose-bottomed plate that had been coated with an anti-IFN-γ antibody. Production of IFN-γ was detected 24 hr later using a secondary horseradish peroxidase-conjugated anti-IFN-γ antibody. The results are summarized in FIG. 9. In FIG. 9, the number of IFN-γ ELISPOT/well is plotted against the E/T ratio. The Xs, open diamonds, open circles and open triangles show the results using PBLs from donors LR-1, LR-2, LR-3 and LR-4, respectively. The solid squares, solid diamonds and solid circles show the results using PBLs from donors HR-1, HR-2 and HR-3, respectively. HIV-1-specific-ELISPOT are shown as the mean ±SE in triplicate wells after subtracting the background from controls.

As shown in FIG. 9, no HIV-specific IFN-γ producing responders were observed in PBLs of four LR donors except for donor 4, who showed a frequency of IFN-γ producing cells at one in $1 \times 10^6$ PBLs at the highest E/T ratio. In contrast, the existence of HIV-specific responders in the PBLs of HR seronegative donors were easily detected; at the E/T ratio of 10:1, the frequencies of HIV-specific IFN-γ producing cells were 14, 21, and 28 per $10^6$ cells for the three HR donors, which was significantly different (P <0.05, t test) from that of the LR donors. Even at an E/T ratio of 0.4:1, HIV-specific IFN-γ-producing cells were still detectable in all three HR donors.

The contribution of the individual subset of immune effector cells in this HIV-specific reaction was further studied by depleting CD4, CD8, or CD56 cells from PBLs of two of these HR donors prior to the in vitro ELISPOT assay. In vitro lymphocyte depletion was conducted as follows. For the depletion of CD4, CD8, and CD56 cells, thawed PBLs were incubated with mouse anti-human CD4-, CD8-, CD56-, or mouse $IgG_1$-labeled BioMag magnetic beads (PerSeptive Diagnostics, Cambridge, Mass.) at 50 beads per cell on ice for 30 min. The depletion was carried out by sorting the cells on a magnet for 5 min two times using mouse $IgG_1$ sorting as control. After depletion, cells were washed with culture medium and seeded in triplicates with the HIV-1-infected autologous PBLs as target cells in an anti-IFN-γ-coated 96-well plate for 24 h as described above. To evaluate the contribution of individual subpopulation of lymphocytes in the IFN-γ production, comparison was based on the initial number of PBL used. Thus, the E/T ratio (10:1) was based on the starting PBL number before depletion. Results of this quantitative analysis indicated that CD8 T cells contributed significantly to the production of IFN-γ (48-71%).

EXAMPLE 18

In Vivo Resistance to HIV-1 Infection Is CD8 T Cell-Dependent

The above information was used to further delineate the mechanism of in vivo protection from HIV-1 in the reconstituted SCID/bg mice. SCID/bg mice were reconstituted with PBLs from LR and HR donors which were either depleted of CD8 T cells or untreated. The reconstituted mice were then inoculated with the macrophage-tropic HIV-$1_{NLAD8}$ and the ability to infect the human PBLs in vivo was examined. PBLs from HR donor 1 were employed in this study. As CD4 cells are the targets of HIV-1 infection, they were not depleted in this study.

a) Depletion of CD8 T Cells in hu-PBL-SCID/bg Mice

CD8 T cells were depleted as described [Baskar et al. (1993) Proc. Natl. Acad. Sci. USA 90:5687] with the following modification. Anti-human CD8 antibody was purified from ascites of OKT8 hybridoma (ATCC CRL 8014) using protein A affinity column (ImmunoPure Plus, Pierce).

Mice were injected IP with 20 μg of the purified antibody five times in total: 2 days before PBL reconstitution, at the time of PBL injection, and at 1, 2, and 3 weeks after PBL injection. To confirm the depletion of CD8 T cells, hu-PBL-SCID/bg mice were killed, and the lymphocytes were analyzed by FACS analysis as described in Ex. 11. The cells were stained with PE-anti-mouse-H-$2K^d$ (Pharmingen) and FITC-anti-human-CD45 (Anti-HLe-1, Becton Dickinson) or with PE-anti-human-CD4 and FITC-anti-human CD8 (Becton Dickinson) for 30 min on ice followed by three washes with immunostaining buffer (PBS containing 0.1% FBS and 0.02% $NaN_3$). Isotype-matched PE-mouse-Ig and FITC-mouse Ig were used as controls.

b) In Vivo Resistance To HIV Infection is Dependent Upon CD8 T Cells

Figure 10B:
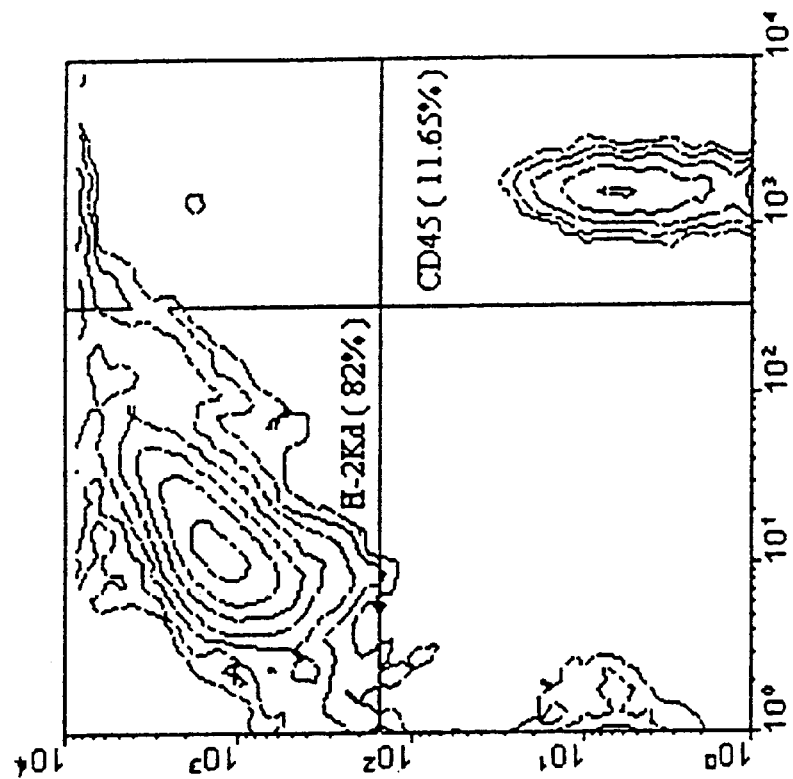
FIGS. 10A–10E demonstrate the HIV-1 infection of human PBLs in hu-PBL-SCID/bg mice treated or untreated with anti-CD8 antibodies.
Figure 10A:
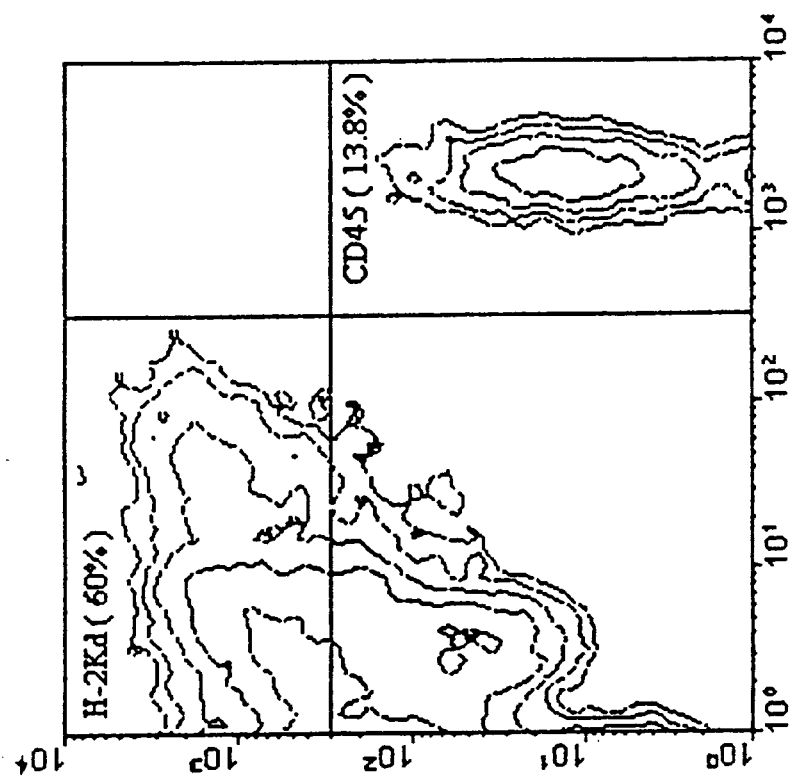
Figure 10D:
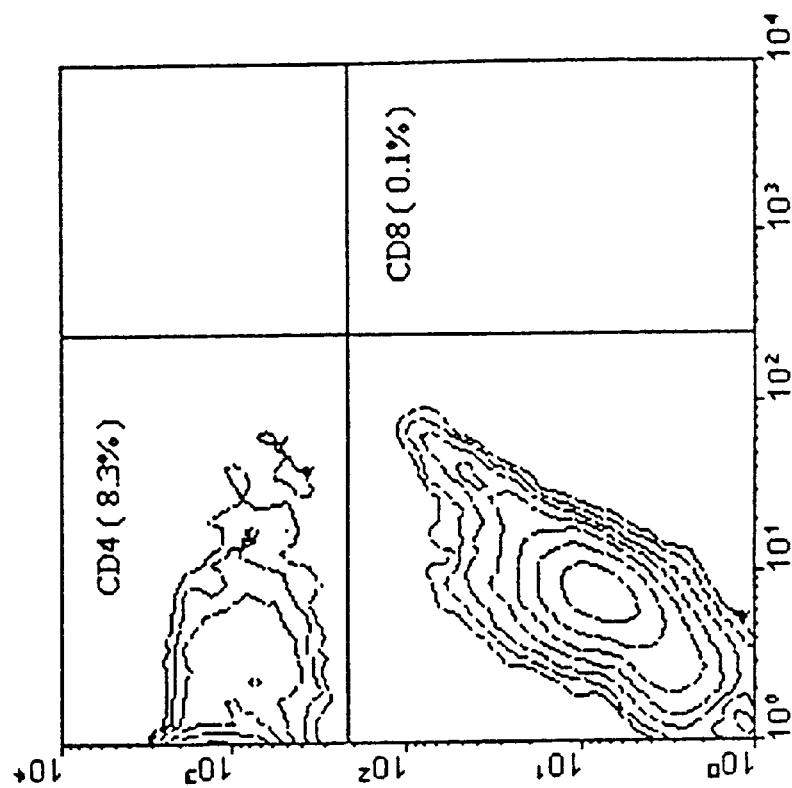
Figure 10C:
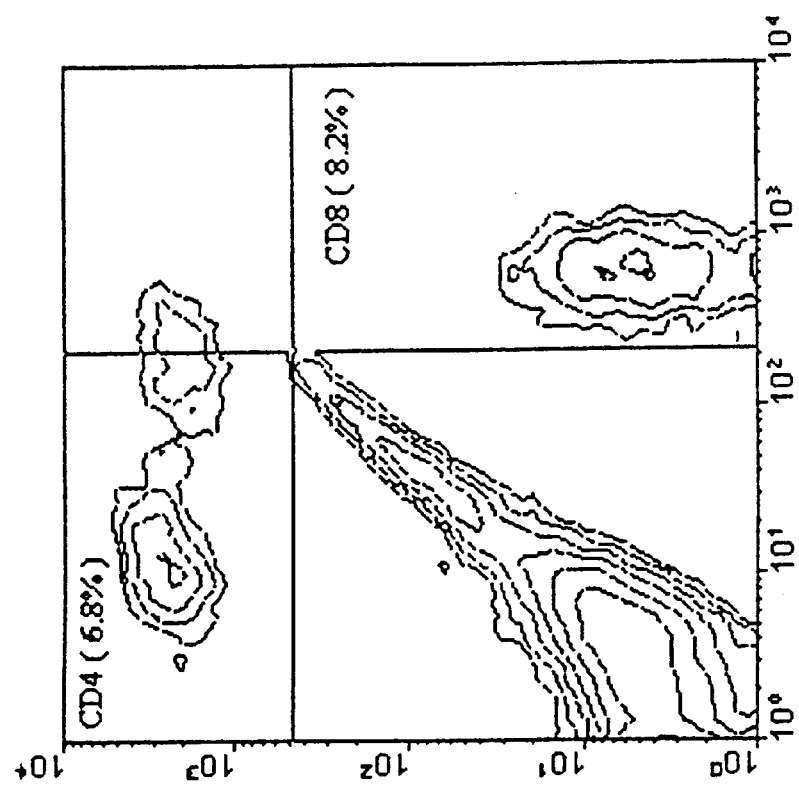

Reconstitution and CD8 depletion were confirmed by FACS analysis 4 weeks later. Representative FACS analysis are shown in FIG. 10. FIGS. 10a and 10c show FACS analysis of splenocytes from the reconstituted hu-PBL-SCID/bg mouse #11 immunostained with anti-mouse H-2Kd, anti-human CD45, anti-human CD4 or anti-human CD8 as depicted. FIGS. 10b and 10d show FACS analysis of splenocytes derived from the reconstituted hu-PBL-SCID/bg mouse #14, after anti-CD8 antibody treatment.

As shown in FIG. 10, in mice receiving no antibody, the following percentages of human lymphocyte subsets were observed: 14% human CD45 cells (FIG. 10a), 7% human CD4 cells, and 8% human CD8 cells (FIG. 10c) in spleens 4 weeks after reconstitution. In mice treated with anti-CD8 antibody, there were similar numbers of CD45 cells in the spleen (12%, FIG. 10b), but the CD8 cells were virtually absent (0.1%, FIG. 10d). These mice were inoculated with the macrophage-tropic HIV-$1_{NLAD8}$ on day 14 after reconstitution and killed 14 days later for analysis as described above. Results of this study are summarized in FIG. 10e.

Figure 10E:
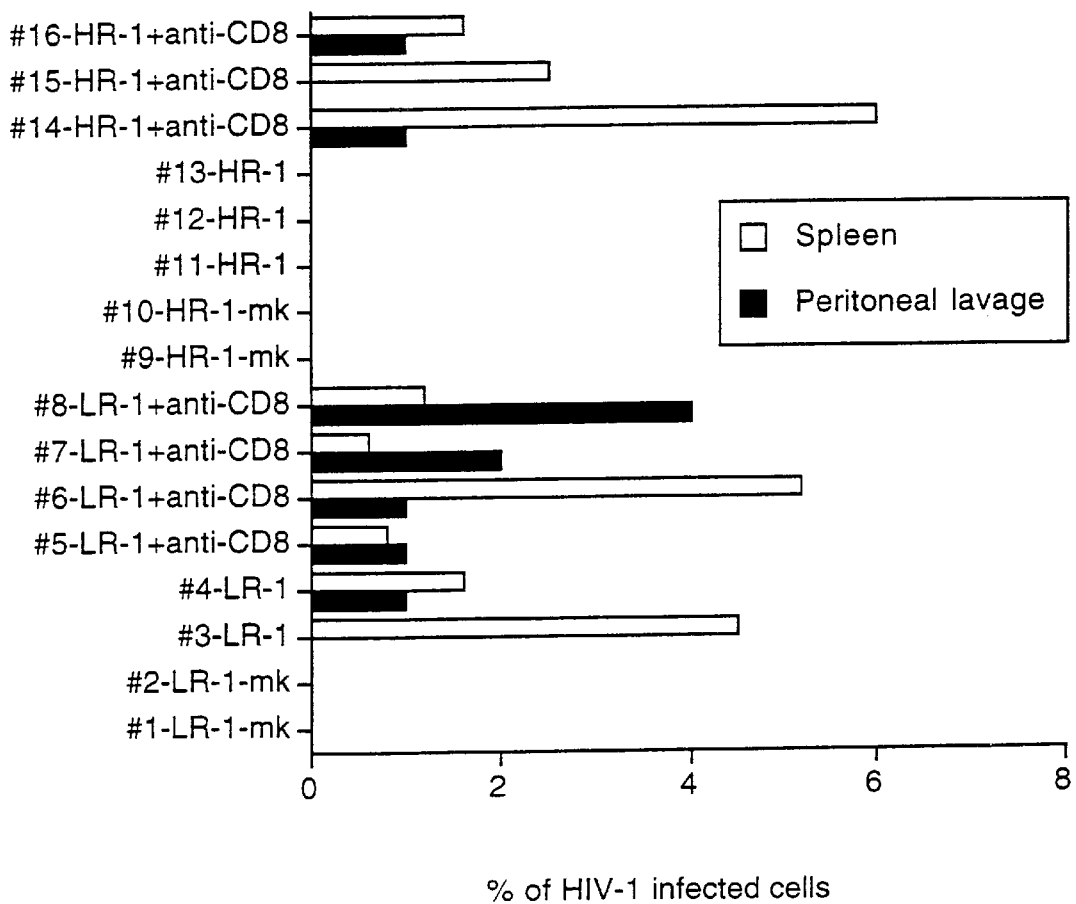

In FIG. 10e, the percentage of HIV-1 infected cells in the spleen (open bars) and in the peritoneal lavage (solid bars) 2 weeks after virus challenge is shown. The mock infected (mk) mice were not treated with anti-CD8 antibody.

The results shown in FIG. 10e demonstrate that mice reconstituted with PBLs from HR donor 1 (HR-1) continued to be resistant to HIV-1 infection as long as CD8 cells were present. However, after CD8 cell depletion, similarly reconstituted mice became susceptible to HIV-1 infection (FIG. 10e, hu-PBL-SCID/bg mice #14, #15, and #16). These results demonstrate that in vivo protection from HIV-1 infection in the reconstituted mice is mediated by human CD8 lymphocytes.

The difference observed between the in vivo shown in this example and the in vitro studies (Ex. 16) indicates that anti-HIV-1 protective immunity cannot be properly assessed by tissue culture infection studies or by the in vitro assays for cell-mediated immunity alone. The hu-PBL-SCID/bg model of the present invention provides a suitable model for the assessment of anti-HIV-1 protective immunity. Results of the in vivo HIV-1 challenge suggest that the cell-mediated immunity developed in these HR subjects also protects against alternative strains of HIV-1 since the challenge strains used in this study, T cell and macrophage tropic HIV-1, are unrelated to the endogenous HIV-1 strains in the corresponding partners of these HR individuals under investigation.

Other studies have demonstrated the development of cell-mediated immune responses in HIV-1 exposed humans [Rowland-Jones el al. (1995) Nat. Med. 1:59; Taylor (1994), supra; Clerici et al. (1992) J. Infect. Dis. 165:1012; Rowland-Jones el al. (1993) Lancet 341:860; Pinto et al. J.

Clin. Invest. 96:867; Clerici et al. (1994) J. Am. Med. Assoc. 271:42 and Shearer and Clerici (1996) Immunol. Today 17:21]. Studies of the simian AIDS models have also suggested that cell-mediated immune responses play an important role in protection against simian immunodeficiency virus infection [Salvato et al. (1994) J. Med. Primatol. 23:125]. It is possible that some genetic factors including HLA haplotype may also contribute to the development of resistance to HIV-1 infection [Haynes et al., supra; Kaslow et al. (1996) Nat. Med. 2:405 and Detels et al. (1996) AIDS 10:102]. However, the two HR subjects who participated in the above hu-PBL-SCID/bg mouse challenge study do not share common HLA haplotypes.

In vivo protective immunity against HIV-1 has also been hypothesized to involve the functions of CD8 T cells that secret anti-HIV chemokines [Cocchi et al. (1995) Science 270:1811]. In addition, CD4 T cells from 2 of 25 frequently exposed but uninfected individuals have recently been shown to have relative resistance to HIV-1 infection [Paxton et al. (1996) Nat. Med. 2:412]; subsequent genotype analysis of these two individuals by PCR and sequencing indicates that they have homozygous defects in the CCR-5 loci that encode the macrophage-tropic HIV-1 coreceptor [Liu et al. (1996) Cell 86:367]. Results of PCR analysis of six multiply-exposed, uninfected individuals including the two HR subjects in our in vivo study showed that one is heterozygous and five are wild type. Both of the HR subjects participating in the in vivo studies have homozygous wild-type CCR-5 loci. This is consistent with the result that PBLs of these two HR subjects were susceptible to macrophage-tropic HIV-1 infection in vitro.

While the in vitro ELISPOT analysis for the HIV-1-reactive effector functions showed that when exposed to autologous HIV-1-infected cells, the Th1-associated, HIV-1 antigen-specific IFN-γ production was higher from CD8 cells than from CD4 or natural killer cells in the HR donors, the possible contribution of CD4 cells to resistance due to the loss of double positive cells ($CD4^+$ $CD8^+$) in the depletion assay cannot be excluded. Thus, it is possible that these two HR, HIV-seronegative individuals participating in the in vivo SCID/beige mouse challenge study may also have protective immunity developed in their CD4 T cell population. Further studies are necessary to characterize the possible mechanisms of CD4 or natural killer cell-mediated resistance.

The above results demonstrate the usefulness of the in vivo hu-PBL-SCID/bg mouse model for evaluating the protective immunity of individuals exposed to HIV-1. The SCID/bg mice can be reconstituted with human PBLs and infected with HIV-1 at a near 100% success rate. In addition, this model is useful for the assessment of the immune status of HIV-1 vaccinees.

EXAMPLE 19

Attenuated Leishmania Cell Vaccines

The biggest frustration in the search for recombinant proteins which might serve as vaccine against a variety of diseases is the fact that recombinant proteins expressed in *Escherichia coli* trigger immune response which are not protective to mammals against the parent eukaryotic and viral pathogens. A major drawback of the bacterial expression system is the inability of bacteria to carry out post-translational modifications such as glycosylation and phosphorylation which eukaryotic proteins require in order to assume their natural configuration and become biologically active [Zhang et al. (1995) Nuc. Acids Res. 23:4073].

Immunization based on proteins expressed in *E. coli* fail to trigger protective immune response because such proteins do not assume the configuration of the wild type protein. In search for a new vaccine, one must always look at the history of vaccinology. The most successful vaccinations have been performed by the use of attenuated or inactivated pathogens. Although safety concerns make such an approach unsuitable for HIV vaccines, it is important to understand why vaccines comprising attenuated pathogens work: these vaccines work because they contain proteins whose configuration are identical with that of the expected pathogens.

Even if a protein has received proper post-translational modifications (e.g., glycosylation and phosphorylation), it will still fail to trigger a protective immune response if the mode of processing and presentation of the vaccine protein to the immune system is not appropriate. This is due to the fact that the mode of processing and presentation of a protein by antigen presenting cell (APC) plays a decisive role in the specific recruitment of distinct T Cell subsets into an immune response [Schirmbeck et al. (1994) J. Immunol. 152:1110]. Two alternative antigen processing pathways are now known [Schirmbeck et al., supra and McDonnell and Askari (1996) New Engl. J. Med. 334:42]. The first alternative is the exogenous pathway through which antigen-presenting cells take up extracellular proteins by either endocytosis or phagocytosis. MHC class II molecules in the endoplasmic reticulum pass through the Golgi apparatus and enter acidified endosomes in which the foreign protein has been fragmented into peptides. The MHC-peptide complex is then brought to the cell surface, where it can be recognized by helper T cells ($CD4^+$). The second alternative is the endogenous pathway by which intracellular proteins in the cytosol are cleaved into short peptides (composing 8 to 10 amino acids). The peptides enter the endoplasmic reticulum with transport-associated proteins (TAP1 and TAP2) and bind there to MHC class I molecules. After binding, the complex is transported through the Golgi apparatus to the cell surface, where it can be recognized by cytotoxic T cells ($CD8^+$). Hence, immunization with soluble protein antigens stimulates $CD4^+$ T cells which are not protective in HIV. In fact, the development of HIV vaccines has been unsuccessful because most of the vaccines are composed of viral subunits expressed in *E. coli* and are presented through exogenous antigen presentation pathway. The route of immunization (oral, rectal, vaginal, etc.) and the pathway of antigen presentation (intracellular vs. extracellular) may hold the key to success in HIV vaccination [Miller and McGhee (1996) Nat. Med. 2:751 and Bloom (1996) Science 272:1888].

In Ex. 17–18 above, it was shown that in vivo protective immunity against HIV in multiple-exposed, seronegative individuals is cell-mediated rather than antibody-mediated. Therefore, the vaccination strategy for induction of immunity against HIV should be directed toward the production of cytotoxic T lymphocytes (CTL) vaccines which are capable of providing heterologous protection against different strains [McDonnell and Askari, supra and Ulmer (1993) Science 259:1745]. $CD8^+$ CTL which are protective in HIV infection can only be triggered if the immunogenic protein is generated within the antigen presenting cell like the macrophages (McDonnell and Askari, supra). The feasibility of using direct DNA injection technology that elicits immune responses similar to those induce by live attenuated vaccines has been demonstrated in animals models (Ulmer, supra), but clinical applications of this form of technology remain elusive (McDonnell and Askari, supra).

To provide a HIV vaccine capable of presenting HIV proteins in their native conformation and in the context of an APC, cysteine protease and HIV proteins were expressed in Leishmania cells to generate an attenuated Leishmania cell capable of acting a vector to transfer HIV proteins to macrophages. Biologically active cysteine protease was produced using this system. Other investigators have reported the production of biologically active human p53, murine INF-γ, Leishmania gp63 and *Plasmodium yoelii* circumsporozoite proteins in Leishmania [Zhang, et al., supra; Tobin et al. (1993) J. Immunol. 150:5059; Liu and Chang (1992) Proc. Natl. Acad. Sci. 89:4991; and Wang et al. (1995) Mol. Biochem. Parasitol. 69:139]. Therefore, it is possible to produce eukaryotic proteins which assume natural configuration in this system.

The impact of over-expressing cysteine proteases in Leishmania pathogenesis was examined. When Leishmania cells over-producing cysteine proteases were injected into susceptible BALB/c mice as a vaccine, the parasite failed to infect mice subsequently challenged with Leishmania; thus, the modified Leishmania cells functioned as an attenuated vaccine. This data suggests that cysteine proteases are powerful immunogens which provide protection against a variety of species of Leishmania. Since Leishmania infects macrophages only, this system provides a unique opportunity to generate proteins of interest (i.e., from pathogens) within the macrophages (APC) without causing disease. This system is used to provide a vector for delivering vaccines against HIV so that immunogenic proteins whose configuration is identical with that of the expected pathogens (e.g., wild type HIV strains) can be delivered and be delivered within the APC to humans. Such a protein would be processed and presented to the immune system through the endogenous pathway resulting in the production of cytotoxic T lymphocytes which are protective against HIV.

To provide Leishmania cell vaccines expressing HIV proteins, sequences of HIV gag-pol/env, env and/or gag genes are cloned downstream of the Leishmania cysteine protease gene as bi- or tri-cistronic constructs using pX or pALT-Neo vectors (kindly provided by Drs. Steven Beverely and Dyann Wirth, respectively; both located at Harvard Medical School, Boston, Mass.). pALT-Neo contains the neo gene inserted between two α-tubulin intergenic sequences and permits the stable expression of the neo gene in Leishmania cells. Expression of such bi- or tri-cistronic constructs have been successfully demonstrated (see Exs. 2, 9 and 10). Expression of gag-pol and env proteins from a replication defective gag-pol-env construct (e.g., pHP-1) has been successfully demonstrated (Ex. 20). Plasmids comprising the gene(s) of interest are used to transfect Leishmania major cells as described [Laban et al. (1990) Nature 343:572]. Briefly, plasmid DNA is linearized and introduced into the promastigote forms of Leishmania cells by electroporation. The electroporated cells are then grown in selective medium (e.g., in medium containing 200 μg/ml G418 when the plasmid employed contains the neo gene).

The transformed Leishmania major cells are examined for their ability to confer protection against HIV. Scid/bg mice reconstituted with human PBLs (i.e., hu-PBL-SCID/bg mice) are infected with Leishmania cells transformed with a cysteine protease-HIV-1 gag-pol/env construct. Two to four weeks later, mice are challenged with HIV-1. Evaluation of protection against infection is conducted two weeks after HIV-1 challenge. Splenocytes from the reconstituted mice are isolated and HIV-specific CMI (cell-mediated immunity) is analyzed using a modified ELISPOT method Ex. 17). The cysteine protease gene will provide protection against Leishmania while the gag-pol/env gene will provide protection against HIV. Attenuated Leishmania vaccines which demonstrate the ability to reduce and/or prevent HIV infection and/or which induce CMI directed against HIV in the animal model of the present invention are then employed for the vaccination of humans.

EXAMPLE 20

Construction of HIV-1 DNA Vaccines

Historically, the most effective vaccines have been live attenuated or inactivated pathogens. Attenuated viruses also have shown promise in AIDS research; the most potent protection of an AIDS-like virus (SIV) in a primate has been observed using attenuated SIV in macaques [Daniels et al. (1992) Science 258:1938]. Therefore, attenuated HIV vaccines may provide effective HIV immunity in humans. In this example, DNA constructs capable of generating viral particles containing an attenuated HIV genome are provided. In addition, DNA constructs comprising a replication-defective HIV provirus which are employed as DNA vaccines are provided.

a) Attenuated Replication-Competent Proviral DNA Vaccines

Several HIV clones containing mutations in the tat and nef genes were constructed to provide live attenuated HIV vaccines; these tat- nef-HIV clones are replication-competent. These HIV constructs may be employed as proviral DNA vaccines (i.e., naked DNA) or employed as a vaccine comprising viral particles. FIGS. 11A–E provide schematics showing the organization of the HIV-1 genome (11A) and the organization of the $HIV_{NL4-3}$, (11B) $HIV_{NL43/AD8/tat-B/nef-B}$ (11C), $HIV_{NL43/nef-B/tat-B}$ (11D), $HIV_{CMV/nef-B/tat-B}$ (11E) and $HIV_{CMV/AD8/nef-B/tat-B}$ (11F) clones. In FIG. 11, the open boxes indicate sequences derived from $HIV_{NL4-3}$, the solid boxes indicate sequences derived from $HIV_{CMV/tat-B}$, the shaded boxes indicate sequences derived from $HIV_{NL43/AD8}$ and the striped boxes indicate sequences derived from $HIV_{NL43/nef-B}$.

Before discussing the construction of specific tat- nef-HIV clones, a number of precursor HIV clones are described. The proviral HIV-1 clone $HIV_{NL4-3}$ provides a full-length HIV-1 genome. $HIV_{ADA}$ is a virus that shows macrophage tropism which localizes to the gp120 domain of the envelope protein. Sequences encoding the envelope protein of $HIV_{ADA}$ were cloned into $HIV_{NL4-3}$ to yield $HIV_{AD8}$, a virus which has demonstrated macrophage tropism (the sequence of the env gene from $HIV_{ADA}$ is available from the GenBank database under accession number M60472). $HIV_{CMV/tatB}$ is an $HIV_{NL4-3}$ derivative containing two alterations (Chang and Zhang, supra). The first alteration consists of the insertion of the CMV-IE enhancer into the 3' and 5' LTR regions of HIV and a deletion of the Sp1 element from the HIV LTR. The second mutation consists of the integration of three stop codons between nt 5851 and 5851 of the tat gene [numbered according to the system of Myers et al. (1992) *Human Retroviruses and AIDS*, Los Alamos National Laboratory, Los Alamos, N.Mex.]. This tat-HIV clone has been shown to be efficiently expressed in several cell lines (Chang and Zhang, supra). $HIV_{NL43/nef-B}$ is an $HIV_{NL4-3}$ derivative in which three stop codons were introduced in the nef gene between nt 8781 and 9031. In addition to the introduction of the three stop codons, this clone contains an engineered HindIII site at nt 8784 and two engineered XbaI sites at nt 9019 and nt 9025. FIGS. 12A–B provide schematics showing a portion of the wild type HIV-1 sequence as well as the tat-B (FIG. 12A; wild-type sequence provided in SEQ ID NO:26) and nef-B mutations (FIG. 12B; wild-type sequence provided in SEQ ID NOS:27 and 28). $HIV_{NL43/AD8/tat-B}$, a Tat-virus, was constructed by ligation of the following three fragments: 1) a ~5.7 kb BamHI-EcoRI fragment isolated from $HIV_{NL43}$ which provides the env-vector backbone-gag-pol region (nt 8465 to 5743) and 2) a ~0.6 kb EcoRI-Asp718 fragment isolated from $HIV_{CMV/tat-B}$ which provides the tat gene (nt 5743 to 6343) and 3) a ~2.1 kb Asp718-BamHI fragment isolated from $HIV_{AD8}$ which provides the env gene (nt 6343 to 8465).

i) Construction of $HIV_{NL43/AD8/tat-B/nef-B}$ $HIV_{NL43/AD8/tat-B/nef-B}$ was constructed by ligation of the following two fragments: 1) a ~5.7 kb BamHI-EcoRI fragment isolated from $HIV_{NL43/nef-B}$ which provides the env-vector backbone-gag-pol region (nt 8465 to 5743) and 2) a ~2.7 kb EcoRI-BamHI fragment isolated from $HIV_{NL43/AD8/tat-B}$ which provides the tat-env region. $HIV_{NL43/AD8/tat-B/nef-B}$ does not produce functional Tat or Nef proteins and is macrophage tropic (AD8 env gene).

ii) Construction of $HIV_{NL43/nef-B/tat-B}$ $HIV_{NL43/nef-B/tat-B}$ was constructed by ligation of the following two fragments: 1) a ~5.7 kb BamHI-EcoRI fragment isolated from $HIV_{NL43/nef-B}$ which provides the env-vector backbone-gag-pol region (nt 8465 to 5743) and 2) a ~2.7 kb EcoRI-BamHI fragment isolated from $HIV_{CMV/tat-B}$ which provides the tat-env region. $HIV_{NL43/nef-B/tat-B}$ does not produce functional Tat or Nef proteins and is T cell tropic (NL4-3 env gene).

iii) Construction of $HIV_{CMV/nef-B/tat-B}$ $HIV_{CMV/nef-B/tat-B}$ was constructed by ligation of the following three fragments: 1) a ~5.7 kb NgoMI-SalI fragment isolated from $HIV_{CMV/tat-B}$ which provides the vector backbone-U3-gag-pol-tat region (nt 10349 to 5785), 2) a ~3.6 kb SalI-BbrPI fragment isolated from $HIV_{NL43/nef-B/tat-B}$ which provides the tat-env-nef region (nt 5785 to 9365) and 3) a ~0.98 kb BbrPI-NgoMI fragment isolated from $HIV_{CMV/tat-B}$ which provides U5 (nt 9365 to 10349). $HIV_{CMV/nef-B/tat-B}$ does not produce functional Tat or Nef proteins and is T cell tropic (NL4-3 env gene).

iv) Construction of $HIV_{CMV/AD8/nef-B/tat-B}$ $HIV_{CMV/AD8/nef-B/tat-B}$ was constructed by ligation of the following three fragments: 1) a ~5.7 kb NgoMI-SalI fragment isolated from $HIV_{CMV/tat-B}$ which provides the vector backbone-U3-gag-pol-tat region (nt 10349 to 5785), 2) a ~3.6 kb SalI-BbrPI fragment isolated from $HIV_{CMV/tat-B}$ which provides the tat-env-nef region (nt 5785 to 9365) and 3) a ~0.98 kb BbrPI-NgoMI fragment isolated from $HIV_{CMV/tat-B}$ which provides U5 (nt 9365 to 10349). $HIV_{CMV/AD8/nef-B/tat-B}$ does not produce functional Tat or Nef proteins and is macrophage tropic (AD8 env gene).

The tat- nef- HIV clones described in sections i–iv above may be employed as naked DNA vaccines or alternatively, these DNA constructs may be transfected into either PBLs ($HIV_{NL43/nef-B/tat-B}$ and $HIV_{CMV/nef-B/tat-B}$) or macrophages ($HIV_{NL43/AD8/tat-B/nef-B}$ and $HIV_{CMV/AD8/nef-B/tat-B}$) and virus may be isolated as described in Ex. 15 and the attenuated viruses may be employed as vaccines. The tat- nef-HIV clones described above will establish an infection in the host and induce both humoral and cell-mediated immune responses which will then control or limit the infection induced by these viruses. Ex. 21 below provide protocols for the evaluation of these attenuated viruses and proviral DNA vaccines in hu-PBL-SCID/bg mice.

b) Replication-Defective HIV-1 Packaging Vector Vaccines

Expression vectors useful for the packaging of HIV-derived vectors are provide useful HIV-1 DNA vaccines as these constructs express viral structural genes but lack the ability to generate viral RNA capable of being packaged into viral particles.

i) Construction of Expression Vectors Capable of Synthesis of All Viral Structural Genes But Lacking Packaging Signals pHP-1 lacks the primer binding site (PBS), polypurine tract (PPT), 3' LTR and most of the untranslated 5' leader sequences including the conventional retroviral packaging signal (Ψ) and the major HIV-1 splice donor (SD) site. pHP-1 contains all HIV structural genes except for the nef gene and thus is capable of expressing the vast majority of the viral proteins. pHP-1 provides a provirus capable of mimicking HIV-1 infection in term of the viral proteins expressed yet this virus cannot be packaged into viral particles. Further the mutations introduced into the pHP-1 provirus greatly reduce the possibility that wild-type HIV virus will be produced by recombination. Thus, pHP-1 provides an excellent HIV DNA vaccine.

pHP-1 was constructed as follows. First, the Tat-responsive enhancer promoter CMV-TATA-TAR fragment (approximately 400 bp) was isolated from d1.kB/Sp1-CMV-TATA-TAR HIV [Chang et al. (1993) J. Virol. 67:743] by BrpI-HindIII digestion, and cloned into EcoRV-BamHI digested pSP72 (Promega) via a linker providing HindIII and BamHI cohesive sites which contains a modified gag AUG with Kozak translation initiation context and a major splice donor site of Rous sarcoma virus. This linker was formed by annealing the following oligonucleotides: 5'-AGCTTGGTCGCCCGGTGGATCAAGACCGGTAG CCGTCATAAAGGTGAT TTCGTCG-3' (SEQ ID NO:29) and 5'-GATCCGACGAAATCACCTTTATGACG GCTACCGGTCTTGATCCACCGGGCGACCA-3' (SEQ ID NO:30). This first subclone was called pSP-CMV-TAR-SD.

Secondly, the gag coding sequence was obtained by PCR from pNL4-3 (a full-length HIV-1 plasmid) using a 5' primer [5'-CGGGATCCACCATGGGTGCGAGAG CGTC-3' (SEQ ID NO:31)] and a 3' primer downstream of the SphI site in the gag gene [5'-ATCCTATTTGTTCCTGAAGG-3' (SEQ ID NO:32)]. The PCR product was digested with BamHI-SphI (~660 bp) and this fragment was ligated with BamHI-SphI digested pSP-CMV-TAR-SD to obtain pSP-CMV-TAR-SD-dl.gag.

Next the poly-A minus subclone pHP-dl.pA was constructed by ligating the following three fragments: a 1112 bp HpaI-SphI fragment isolated from pSP-CMV-TAR-SD-dl.gag (contains the promoter-TAR-SD-dl.gag), a 7922 bp SphI-XhoI fragment (dl.gag-pol-env-gpt) of pNLgpt, and a plasmid vector backbone provided by EcoRV-XhoI digested pBS-KS(–) (Stratagene).

Lastly, pHP-1 was made by the following ligation: NotI-XhoI (9059 bp) of pHP-dl.pA containing dl.CMV-TATA-TAR-SD-gag-pol-env-gpt, a 422 bp poly-A site from XhoI-PstI digested pREP9 (Invitrogen), and NotI-PstI digested pBS-KS(–). The sequence of pHP-1 (12.494 kb) is provided in SEQ ID NO:33; this sequence begins at the promoter at the half-BbrPI site.

To see whether an replication-competent HIV (RC-HIV) recombinant could be generated, human TE671 cells (ATCC CRL 8805) were transfected with pHP-1 DNA and the transfected cells were cocultured with the human lymphoma cell line MT4 for 7 days. MT4 cells (NIH AIDS Research and Reference Reagent Program of National Institutes of Health, Bethesda, MD) are an HTLV-I transformed human CD4+ lymphoma cell line, which are very sensitive to HIV-1 infection. No infectious HIV-1 was detected after a 2 month coculture indicating the absence of RC-HIV production in cells containing pHP-1. To detect the synthesis of HIV-1 proteins, cell lysates were prepared and analyzed by Western blotting in comparison with a wild type HIV-1 construct, pNL4-3. Results of this study showed that the level of viral proteins synthesized by pHP-1 was similar to that of the wild type pNL4-3.

Analysis of reverse transcriptase (RT) activity in the transfected culture supernatants indicated that the level of active RT production was reduced 40% for pHP-1 compared with the wild type construct pNL4-3. The expression of Gag-Pol function indicates that tat and rev are functional. Thus, the artificially engineered splice donor (SD) site in the pHP-1 construct, which is unrelated to HIV sequences, works like the wild type SD site (i.e., allowing partition of spliced and unspliced mRNAs into the cytoplasm).

pHP-1 contains the bacterial gpt gene and lacks the HIV nef gene. The gpt gene is removed from pHP-1 to create pHP-2 as follows. pHP-1 is digested with BamHI and SphI and the ~7 kb BamHI (nt 8870 of pHP-1)-SphI (nt 1842 of pHP-1) fragment is isolated. pHP-1 is digested with BamHI and HindIII and the 322 bp BamHI (nt 8870 of pHP-1)-HindIII (nt 9192 of pHP-1) fragment is isolated. pHP-1 is digested with XhoI and EcoRI and the 431 bp XhoI (nt 9764 of pHP-1)-EcoRI (nt 10195 of pHP-1) fragment is isolated. pHP-1 is digested with EcoRI and SphI and the ~1.8 kb EcoRI (nt 10195 of pHP-1)-SphI (nt 1842 of pHP-1) fragment is isolated. These four fragments are ligated together along with an HindIII-XhoI adapter to generate pHP-2. pHP-2 lacks the gpt gene of pHP-1 and also lacks the HIV nef gene.

The nef gene is inserted into pHP-2 to generate pHP-3. pHP-3 contains all HIV structural genes and like pHP-1 and pHP-2 is replication-defective. The nef gene is isolated by PCR amplification using primers having a HindIII (5' primer) or a XhoI site (3' primer) in addition to sequences complementary to the nef gene. The amplified PCR product is digested with HindIII and XhoI and ligated with the four fragments derived from pHP-1 used to generate pHP-2 (described above) to generate pHP-3. The nef PCR product is thus used in place of the HindIII-XhoI adapter used to generate pHP-2 in the construction of pHP-3.

The proviruses contained on pHP-1, pHP-2 and pHP-3 can be placed on vector backbone having a kanamycin-resistance gene rather than an ampicillin-resistance gene using standard techniques in order to satisfy requirements for FDA approval of DNA vaccines.

The ability of pHP-1, pHP-2 and/or pHP-3 DNA (or kanamycin-resistant derivatives) to function as effective HIV vaccines is evaluated in the hu-PBL-SCID/bg mice as described in Ex. 21 below.

EXAMPLE 21

Evaluation of Candidate Vaccines In Hu-PBL-SCID/beige Mice

This example describes the use of hu-PBL-SCID/bg mice for the evaluation of vaccines designed to induce immunity against human pathogens. When working with mice exposed to attenuated or wild type HIV, extreme caution is taken to avoid exposure to HIV. Double gloves are worn and mice are handled (prior to anaesthesia) using long forceps. All procedures related to HIV are conducted in a Bio-safety level 3 facility; all blood and tissue samples transferred out of the level 3 facility are kept in a bio-safety container.
a) Reconstitution Of Hu-PBL-SCID/bg Mice Hu-PBL-SCID/bg mice are prepared as described in Ex. 3 or as follows. Human PBLs are isolated by density gradient centrifugation on Ficoll-Hypaque (Ex. 15). The separated PBL are resuspended in PBS at a concentration of $4\times10^7$/ml. Freshly isolated PBLs (i.e., within 2 hr of isolation) are preferred for the reconstitution of SCID/bg mice. Frozen PBLs and buffy coat preparations (as provided by blood banks) permitted to stand at room temperature for ~24 hr demonstrate a reduced efficiency of reconstitution compared to freshly isolated PBLs.

SCID/bg mice are injected i.p. with $2\times10^7$ human PBLs in 0.5 ml PBS. The injected animals are placed in clean cages on a folded piece of paper towel (on the cage bottom) to avoid inhalation of the bedding and are checked daily.
b) Confirmation Of Reconstitution By ELISA Three to four weeks after the injection of human PBLs, blood is collected from the mouse tail using a microtainer (Beckton Dickinson). The blood sample is tested for human immunoglobulin (hu-Ig) by ELISA. Animals with hu-Ig levels >100 μg/ml are considered successfully reconstituted. Animals with hu-Ig levels >100 μg/ml at the time they are to be vaccinated (i.e., injected with a preparation comprising a candidate vaccine such as an attenuated HIV or a HIV DNA preparation) may be employed for the evaluation of vaccines. Typically, animals receive the first dose of vaccine 1–2 weeks after injection of human PBLs.
c) Immunization of Hu-PBL-SCID/bg Mice With Heterologous DNA Vaccines Hu-PBL-SCID/beige mice are generated as described in section a) above. One week after injection of the human PBLs, the reconstituted mice are anesthetized with metofane. Once the surgical plane of anesthesia is reached, the animal is placed in a restraint device and immunized with either 1) 0.5 ml of attenuated HIV (e.g., $HIV_{NL43/AD8/tat-B/nef-B}$) (TCID50=50 to 100, in AIM-V serum-free medium) by i.p. injection, or 2) 0.2 ml (containing approximately 30 μg DNA in saline) of naked proviral DNA (e.g., pHP-1) via intramuscular injection. After the first injection, the same immunization process is be repeated twice, with three days between immunizations.

One week after the last injection of the attenuated live or DNA HIV vaccine, the animal is challenged with wild type HIV isolates by i.p. injection (0.5 ml, TCID50=100) under anesthesia with metofane. Following immunization and challenge with wild type HIV-1, blood samples (0.1 ml) are collected weekly from the mouse tail to monitor HIV-1 infection by immunohistochemical staining using an anti-p24 monoclonal antibody (prepared from hybridoma 183-H12-5C; available from the NIH AIDS Research and Reference Reagent Program of National Institutes of Health); the staining is carried out as described in Ex. 15. At various time points, the animals are sacrificed by cervical dislocation after induction of anesthesia. At the time of sacrifice, the blood, peritoneal lavage and spleen are collected for examination of HIV-1 infection. The splenocytes are also used to investigate HIV-1-specific CMI responses by ELISPOT (Ex. 17).
d) Evaluation of Attenuated HIV Vaccines and Anti-HIV Gene Therapy Vectors in Humanized SCID/beige Mice Human immune function in established in SCID/beige mice using human fetal hematopoietic tissues (liver, thymus, lymph node or bone marrow). These humanized animals provide models for the evaluation of HIV vaccines and anti-HIV gene therapy strategies.
  i) Establishment of Humanized SCID/beige Mice Human fetal tissue is prepared for transplantation as follows. Human fetal tissue (HIV-negative), 17–24 gestational weeks, is obtained from Advanced Bioscience Resources, Inc. (Alameda, Calif.), and placed in a sterile 50 ml tube containing RPMI 1640 medium supplemented with 10% fetal calf serum (FCS), 50 units/ml penicillin and 50

μg/ml streptomycin. The samples are shipped on wet ice and received within 36 hours. Tissue and blood is tested for the presence of HIV using a PCR assay. In addition, for future use, the organ fragments or dissociated cells are frozen in 10% DMSO and 40% FCS.

SCID/bg mice are anesthetized with metofane. A 1.5 cm$^2$ area on the back of each mouse is shaved using a #22 blade and this area is swabbed with povidone iodine. A 1-cm flank incision is made to expose the right or/and left kidneys.

Human fetal liver and thymus are cut with a sharp blade into small pieces (1 mm$^3$). About 10 pieces of each tissue are implanted under the kidney capsule using a 16 or 18-gauge trocar. The wound is sutured and metal clips are secured over the wound to ensure the healing.

Blood samples (0.1 ml) are collected from mouse tails monthly to confirm the presence of human immune cells (as described in Ex. 11; additional markers such as CD25 may also be employed) and human Ig in the peripheral blood (by ELISA) in the transplanted SCID/bg mice. Once the immune system of the SCID/beige mice is successfully humanized, they are used for vaccine evaluation. Alternatively, transduced human hematopoietic stem cells (CD34+ cells) carrying anti-HIV genes can be injected i.p. into the humanized SCID/beige mice. Hematopoietic stem cells are transduced (i.e., infected) using Moloney murine leukemia virus (MoMLV)-based vectors or HIV-based vectors comprising anti-HIV genes (e.g., anti-HIV ribozymes and intracellular single chain antibody genes). Examples of MoMLV-based vectors comprising anti-HIV genes are provided in co-pending application Ser. No. 08/336,132 the disclosure of which is herein incorporated by reference.

ii) Evaluation of Attenuated HIV Vaccine and Anti-HIV Gene Therapy Vectors in the Humanized SCID/beige Mice The humanized (i.e., transplanted) SCID/bg mice are anesthetized with metofane and placed in a restraint device and injected with attenuated HIV vaccines as described above (virus in AIM-V medium or DNA in saline). After three injections of the attenuated HIV vaccines (spaced 3–7 days apart), the animals are challenged with wild type HIV-1 by i.p. injection (0.5 ml, TCID50=100) under the anesthesia with metofane. Following wild type HIV injection, blood samples are collected weekly from the tail under the anesthesia with metofane to check for HIV infection.

At various time points (before death), the animals are sacrificed by cervical dislocation post-anesthesia. At the same time, the blood, peritoneal lavage and spleen are collected for the examination of HIV infection and in vitro CMI by ELISPOT as described in Ex. 17.

It is clear from the above that the present invention provides animal models suitable for the evaluation of HIV vaccines and anti-HIV immunity. In addition, the present invention provides attenuated live HIV vaccines and DNA vaccines for the induction of anti-HIV immunity.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

I claim:

1. A method for evaluating a response of human immune cells to a human immunodeficiency virus, said method comprising:
   a) providing:
      i) a SCID/beige mouse reconstituted with said human immune cells;
      ii) an injectable preparation comprising one or more components from said human immunodeficiency virus;
      iii) a composition comprising non-attenuated human immunodeficiency virus;
   b) injecting said mouse with said injectable preparation to produce an injected mouse;
   c) exposing said injected mouse to said composition; and
   d) monitoring said exposed mouse for an immune response of said human immune cells to said non-attenuated human immunodeficiency virus;
wherein said component of said human immunodeficiency virus comprises DNA, said DNA comprising proviral DNA encoding a human immunodeficiency virus genome capable of expressing viral structural genes but incapable of being packaged into viral particles, and wherein said DNA comprises plasmid DNA selected from the group consisting of pHP-1, pHP-2 and pHP-3.

2. The method of claim 1, wherein said injecting of step b) is repeated at least once prior to exposing said mouse to said composition.

3. The method of claim 1, wherein said injectable preparation comprises an attenuated replication-competent human immunodeficiency virus.

4. The method of claim 3, wherein the genome of said attenuated virus comprises a tat gene comprising a mutation wherein functional Tat protein is not expressed.

5. The method of claim 4, wherein said genome of said attenuated virus further comprises a nef gene comprising a mutation wherein functional Nef protein is not expressed.

\* \* \* \* \*

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
      (A) LENGTH: 6145 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO: 1:

```
GAATTCATAC CAGATCACCG AAAACTGTCC TCCAAATGTG TCCCCCTCAC ACTCCCAAAT        60

TCGCGGGCTT CTGCCTCTTA GACCACTCTA CCCTATTCCC CACACTCACC GGAGCCAAAG       120

CCGCGGCCCT TCCGTTTCTT TGCTTTTGAA AGACCCCACC CGTAGGTGGC AAGCTAGCTT       180

AAGTAACGCC ACTTTGCAAG GCATGGAAAA ATACATAACT GAGAATAGAA AAGTTCAGAT       240

CAAGGTCAGG AACAAAGAAA CAGCTGAATA CCAAACAGGA TATCTGTGGT AAGCGGTTCC       300

TGCCCCGGCT CAGGGCCAAG AACAGATGAG ACAGCTGAGT GATGGGCCAA ACAGGATATC       360

TGTGGTAAGC AGTTCCTGCC CCGGCTCGGG GCCAAGAACA GATGGTCCCC AGATGCGGTC       420

CAGCCCTCAG CAGTTTCTAG TGAATCATCA GATGTTTCCA GGGTGCCCCA AGGACCTGAA       480

AATGACCCTG TACCTTATTT GAACTAACCA ATCAGTTCGC TTCTCGCTTC TGTTCGCGCG       540
```

| | |
|---|---|
| CTTCCGCTCT CCGAGCTCAA TAAAAGAGCC CACAACCCCT CACTCGGCGC GCCAGTCTTC | 600 |
| CGATAGACTG CGTCGCCCGG GTACCCGTAT TCCCAATAAA GCCTCTTGCT GTTTGCATCC | 660 |
| GAATCGTGGT CTCGCTGTTC CTTGGGAGGG TCTCCTCTGA GTGATTGACT ACCCACGACG | 720 |
| GGGGTCTTTC ATTTGGGGGC TCGTCCGGGA TTTGGAGACC CCTGCCCAGG GACCACCGAC | 780 |
| CCACCACCGG GAGGTAAGCT GGCCAGCAAC TTATCTGTGT CTGTCCGATT GTCTAGTGTC | 840 |
| TATGTTTGAT GTTATGCGCC TGCGTCTGTA CTAGTTAGCT AACTAGCTCT GTATCTGGCG | 900 |
| GACCCGTGGT GGAACTGACG AGTTCTGAAC ACCCGGCCGC AACCCTGGGA GACGTCCCAG | 960 |
| GGACTTTGGG GGCCGTTTTT GTGGCCCGAC CTGAGGAAGG GAGTCGATGT GGAATCCGAC | 1020 |
| CCCGTCAGGA TATGTGGTTC TGGTAGGAGA CGAGAACCTA AAACAGTTCC CGCCTCCGTC | 1080 |
| TGAATTTTTG CTTTCGGTTT GGAACCGAAG CCGCGCGTCT TGTCTGCTGC AGCGCTGCAG | 1140 |
| CATCGTTCTG TGTTGTCTCT GTCTGACTGT GTTTCTGTAT TTGTCTGAAA ATTAGGGCCA | 1200 |
| GACTGTTACC ACTCCCTTAA GTTTGACCTT AGGTCACTGG AAAGATGTCG AGCGGATCGC | 1260 |
| TCACAACCAG TCGGTAGATG TCAAGAAGAG ACGTTGGGTT ACCTTCTGCT CTGCAGAATG | 1320 |
| GCCAACCTTT AACGTCGGAT GGCCGCGAGA CGGCACCTTT AACCGAGACC TCATCACCCA | 1380 |
| GGTTAAGATC AAGGTCTTTT CACCTGGCCC GCATGGACAC CCAGACCAGG TCCCCTACAT | 1440 |
| CGTGACCTGG GAAGCCTTGG CTTTTGACCC CCCTCCCTGG GTCAAGCCCT TTGTACACCC | 1500 |
| TAAGCCTCCG CCTCCTCTTC CTCCATCCGC CCCGTCTCTC CCCCTTGAAC CTCCTCGTTC | 1560 |
| GACCCCGCCT CGATCCTCCC TTTATCCAGC CCTCACTCCT TCTCTAGGCG CCGGAATTCC | 1620 |
| GATCTGATCA AGAGACAGGA TGAGGATCGT TTCGCATGAT TGAACAAGAT GGATTGCACG | 1680 |
| CAGGTTCTCC GGCCGCTTGG GTGGAGAGGC TATTCGGCTA TGACTGGGCA ACAGACAA | 1740 |
| TCGGCTGCTC TGATGCCGCC GTGTTCCGGC TGTCAGCGCA GGGGCGCCCG GTTCTTTTTG | 1800 |
| TCAAGACCGA CCTGTCCGGT GCCCTGAATG AACTGCAGGA CGAGGCAGCG CGGCTATCGT | 1860 |
| GGCTGGCCAC GACGGGCGTT CCTTGCGCAG CTGTGCTCGA CGTTGTCACT GAAGCGGGAA | 1920 |
| GGGACTGGCT GCTATTGGGC GAAGTGCCGG GGCAGGATCT CCTGTCATCT CACCTTGCTC | 1980 |
| CTGCCGAGAA AGTATCCATC ATGGCTGATG CAATGCGGCG GCTGCATACG CTTGATCCGG | 2040 |
| CTACCTGCCC ATTCGACCAC CAAGCGAAAC ATCGCATCGA GCGAGCACGT ACTCGGATGG | 2100 |
| AAGCCGGTCT TGTCGATCAG GATGATCTGG ACGAAGAGCA TCAGGGGCTC GCGCCAGCCG | 2160 |
| AACTGTTCGC CAGGCTCAAG GCGCGCATGC CCGACGGCGA GGATCTCGTC GTGACCCATG | 2220 |
| GCGATGCCTG CTTGCCGAAT ATCATGGTGG AAAATGGCCG CTTTTCTGGA TTCATCGACT | 2280 |
| GTGGCCGGCT GGGTGTGGCG GACCGCTATC AGGACATAGC GTTGGCTACC CGTGATATTG | 2340 |
| CTGAAGAGCT TGGCGGCGAA TGGGCTGACC GCTTCCTCGT GCTTTACGGT ATCGCCGCTC | 2400 |
| CCGATTCGCA GCGCATCGCC TTCTATCGCC TTCTTGACGA GTTCTTCTGA GCGGACTCT | 2460 |
| GGGGTTCGAA ATGACCGACC AAGCGACGCC CAACCTGCCA TCACGAGATT TCGATTCCAC | 2520 |
| CGCCGCCTTC TATGAAAGGT TGGGCTTCGG AATCGTTTTC CGGGACGCCG GCTGGATGAT | 2580 |
| CCTCCAGCGC GGGGATCTCA TGCTGGAGTT CTTCGCCCAC CCCGGGCTCG ATCCCCTCGC | 2640 |
| GAGTTGGTTC AGCTGCTGCC TGAGGCTGGA CGACCTCGCG GAGTTCTACC GGCAGTGCAA | 2700 |
| ATCCGTCGGC ATCCAGGAAA CCAGCAGCGG CTATCCGCGC ATCCATGCCC CGAACTGCA | 2760 |
| GGAGTGGGGA GGCACGATGG CCGCTTTGGT CGACCCGGAC GGGACGCTCC TGCGCCTGAT | 2820 |
| ACAGAACGAA TTGCTTGCAG GCATCTCATG AGTGTGTCTT CCCGTTTTCC GCCTGAGGTC | 2880 |

-continued

| | | | | |
|---|---|---|---|---|
| ACTGCGTGGA | TGGAGCGCTG | GCGCCTGCTG | CGCGACGGCG | AGCTGCTCAC CACCCACTCG 2940 |
| AGGGCGTGCA | GCGCTGCAGA | GGCCGAGTGC | AGAACTGCTC | CAAAGGGACC TCAAGGCTTT 3000 |
| CCGAGGGACA | CTAGGCTGAC | TCCATCGAGC | CAGTGTAGAG | ATAAGCTTAT CGATTAGTCC 3060 |
| AATTTGTTAA | AGACAGGATA | TCAGTGGTCC | AGGCTCTAGT | TTTGACTCAA CAATATCACC 3120 |
| AGCTGAAGCC | TATAGAGTAC | GAGCCATAGA | TAAAATAAAA | GATTTTATTT AGTCTCCAGA 3180 |
| AAAAGGGGGG | AATGAAAGAC | CCCACCTGTA | GGTTTGGCAA | GCTAGCTTAA GTAACGCCAT 3240 |
| TTTGCAAGGC | ATGGAAAAAT | ACATAACTGA | GAATAGAGAA | GTTCAGATCA AGGTCAGGAA 3300 |
| CAGATGGAAC | AGCTGAATAT | GGGCCAAACA | GGATATCTGT | GGTAAGCAGT TCCTGCCCCG 3360 |
| GCTCAGGGCC | AAGAACAGAT | GGAACAGCTG | AATATGGGCC | AAACAGGATA TCTGTGGTAA 3420 |
| GCAGTTCCTG | CCCCGGCTCA | GGGCCAAGAA | CAGATGGTCC | CCAGATGCGG TCCAGCCCTC 3480 |
| AGCAGTTTCT | AGAGAACCAT | CAGATGTTTC | CAGGGTGCCC | CAAGGACCTG AAATGACCCT 3540 |
| GTGCCTTATT | TGAACTAACC | AATCAGTTCG | CTTCTCGCTT | CTGTTCGCGC GCTTCTGCTC 3600 |
| CCCGAGCTCA | ATAAAAGAGC | CCACAACCCC | TCACTCGGGG | CGCCAGTCCT CCGATTGACT 3660 |
| GAGTCGCCCG | GGTACCCGTG | TATCCAATAA | ACCCTCTTGC | AGTTGCATCC GACTTGTGGT 3720 |
| CTCGCTGTTC | CTTGGGAGGG | TCTCCTCTGA | GTGATTGACT | ACCCGTCAGC GGGGGTCTTT 3780 |
| CATTTGGGGG | CTCGTCCGGG | ATCGGAGAC | CCCTGCCCAG | GGACCACCGA CCCACCACCG 3840 |
| GGAGGTAAGC | TGGCTGCCTC | GCGCGTTTCG | GTGATGACGG | TGAAAACCTC TGACACATGC 3900 |
| AGCTCCCGGA | GACGGTCACA | GCTTGTCTGT | AAGCGGATGC | CGGGAGCAGA CAAGCCCGTC 3960 |
| AGGGCGCGTC | AGCGGGTGTT | GGCGGGTGTC | GGGGCGCAGC | CATGACCCAG TCACGTAGCG 4020 |
| ATAGCGGAGT | GTATACTGGC | TTAACTATGC | GGCATCAGAG | CAGATTGTAC TGAGAGTGCA 4080 |
| CCATATGCGG | TGTGAAATAC | CGCACAGATG | CGTAAGGAGA | AAATACCGCA TCAGGCGCTC 4140 |
| TTCCGCTTCC | TCGCTCACTG | ACTCGCTGCG | CTCGGTCGTT | CGGCTGCGGC GAGCGGTATC 4200 |
| AGCTCACTCA | AAGGCGGTAA | TACGGTTATC | CACAGAATCA | GGGGATAACG CAGGAAAGAA 4260 |
| CATGTGAGCA | AAAGGCCAGC | AAAAGGCCAG | GAACCGTAAA | AAGGCCGCGT TGCTGGCGTT 4320 |
| TTTCCATAGG | CTCCGCCCCC | CTGACGAGCA | TCACAAAAAT | CGACGCTCAA GTCAGAGGTG 4380 |
| GCGAAACCCG | ACAGGACTAT | AAAGATACCA | GGCGTTTCCC | CCTGGAAGCT CCCTCGTGCG 4440 |
| CTCTCCTGTT | CCGACCCTGC | CGCTTACCGG | ATACCTGTCC | GCCTTTCTCC CTTCGGAAG 4500 |
| CGTGGCGCTT | TCTCATAGCT | CACGCTGTAG | GTATCTCAGT | TCGGTGTAGG TCGTTCGCTC 4560 |
| CAAGCTGGGC | TGTGTGCACG | AACCCCCCGT | TCAGCCCGAC CGCTGCGCCT | TATCCGGTAA 4620 |
| CTATCGTCTT | GAGTCCAACC | CGGTAAGACA | CGACTTATCG | CCACTGGCAG CAGCCACTGG 4680 |
| TAACAGGATT | AGCAGAGCGA | GGTATGTAGG | CGGTGCTACA | GAGTTCTTGA AGTGGTGGCC 4740 |
| TAACTACGGC | TACACTAGAA | GGACAGTATT | TGGTATCTGC | GCTCTGCTGA AGCCAGTTAC 4800 |
| CTTCGGAAAA | AGAGTTGGTA | GCTCTTGATC | CGGCAAACAA | ACCACCGCTG GTAGCGGTGG 4860 |
| TTTTTTTGTT | TGCAAGCAGC | AGATTACGCG | CAGAAAAAAA | GGATCTCAAG AAGATCCTTT 4920 |
| GATCTTTTCT | ACGGGGTCTG | ACGCTCAGTG | GAACGAAAAC | TCACGTTAAG GGATTTTGGT 4980 |
| CATGAGATTA | TCAAAAAGGA | TCTTCACCTA | GATCCTTTTA | AATTAAAAAT GAAGTTTTAA 5040 |
| ATCAATCTAA | AGTATATATG | AGTAAACTTG | GTCTGACAGT | TACCAATGCT TAATCAGTGA 5100 |
| GGCACCTATC | TCAGCGATCT | GTCTATTTCG | TTCATCCATA | GTTGCCTGAC TCCCCGTCGT 5160 |
| GTAGATAACT | ACGATACGGG | AGGGCTTACC | ATCTGGCCCC | AGTGCTGCAA TGATACCGCG 5220 |
| AGACCCACGC | TCACCGGCTC | CAGATTTATC | AGCAATAAAC | CAGCCAGCCG GAAGGGCCGA 5280 |

```
GCGCAGAAGT GGTCCTGCAA CTTTATCCGC CTCCATCCAG TCTATTAATT GTTGCCGGGA      5340

AGCTAGAGTA AGTAGTTCGC CAGTTAATAG TTTGCGCAAC GTTGTTGCCA TTGCTGCAGG      5400

CATCGTGGTG TCACGCTCGT CGTTTGGTAT GGCTTCATTC AGCTCCGGTT CCCAACGATC      5460

AAGGCGAGTT ACATGATCCC CCATGTTGTG CAAAAAAGCG GTTAGCTCCT TCGGTCCTCC      5520

GATCGTTGTC AGAAGTAAGT TGGCCGCAGT GTTATCACTC ATGGTTATGG CAGCACTGCA      5580

TAATTCTCTT ACTGTCATGC CATCCGTAAG ATGCTTTTCT GTGACTGGTG AGTACTCAAC      5640

CAAGTCATTC TGAGAATAGT GTATGCGGCG ACCGAGTTGC TCTTGCCCGG CGTCAACACG      5700

GGATAATACC GCGCCACATA GCAGAACTTT AAAAGTGCTC ATCATTGGAA AACGTTCTTC      5760

GGGGCGAAAA CTCTCAAGGA TCTTACCGCT GTTGAGATCC AGTTCGATGT AACCCACTCG      5820

TGCACCCAAC TGATCTTCAG CATCTTTTAC TTTCACCAGC GTTTCTGGGT GAGCAAAAAC      5880

AGGAAGGCAA AATGCCGCAA AAAAGGGAAT AAGGGCGACA CGGAAATGTT GAATACTCAT      5940

ACTCTTCCTT TTTCAATATT ATTGAAGCAT TTATCAGGGT TATTGTCTCA TGAGCGGATA      6000

CATATTTGAA TGTATTTAGA AAAATAAACA AATAGGGGTT CCGCGCACAT TTCCCCGAAA      6060

AGTGCCACCT GACGTCTAAG AAACCATTAT TATCATGACA TTAACCTATA AAAATAGGCG      6120

TATCACGAGG CCCTTTCGTC TTCAA                                           6145

(2) INFORMATION FOR SEQ ID NO: 2:

(i) SEQUENCE CHARACTERISTICS:
         (A) LENGTH: 67 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO: 2:

GATCTAAGCT TGCGGCCGCA GATCTCGAGC CATGGATCCT AGGCCTGATC ACGCGTCGAC       60

TCGCGAT                                                                67

(2) INFORMATION FOR SEQ ID NO: 3:

(i) SEQUENCE CHARACTERISTICS:
         (A) LENGTH: 65 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO: 3:

CGATCGCGAG TCGACGCGTG ATCAGGCCTA GGATCCATGG CTCGAGATCT GCGGCCGCAA       60

GCTTA                                                                  65

(2) INFORMATION FOR SEQ ID NO: 4:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"
```

(xi) SEQUENCE DESCRIPTION: SEQ ID NO: 4:

AAGCTTGATC ACCACCATGA TTGAACAAGA TGG                                33

(2) INFORMATION FOR SEQ ID NO: 5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 5:

CCGGATCCGT CGACCCCAGA GTCCCGCTCA GAAG                               34

(2) INFORMATION FOR SEQ ID NO: 6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 6:

CCCGGGAAGC TTCCACCATG TGGCTGCAGA GCCTG                              35

(2) INFORMATION FOR SEQ ID NO: 7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 7:

AATGGATCCT ATCACTCCTG GACTGGCTC                                     29

(2) INFORMATION FOR SEQ ID NO: 8:

(i) SEQUENCE CHARACTERISTICS:
        (A) LENGTH: 435 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 8:

ATGTGGCTGC AGAGCCTGCT GCTCTTGGGC ACTGTGGCCT GCAGCATCTC TGCACCCGCC     60

CGCTCGCCCA GCCCCAGCAC GCAGCCCTGG GAGCATGTGA ATGCCATCCA GGAGGCCCGG    120

CGTCTCCTGA ACCTGAGTAG AGACACTGCT GCTGAGATGA ATGAAACAGT AGAAGTCATC    180

TCAGAAATGT TTGACCTCCA GGAGCCGACC TGCCTACAGA CCCGCCTGGA GCTGTACAAG    240

CAGGGCCTGC GGGGCAGCCT CACCAAGCTC AAGGGCCCCT TGACCATGAT GGCCAGCCAC    300

TACAAGCAGC ACTGCCCTCC AACCCCGGAA ACTTCCTGTG CAACCCAGAT TATCACCTTT    360

GAAAGTTTCA AGAGAACCT GAAGGACTTT CTGCTTGTCA TCCCCTTTGA CTGCTGGGAG    420

```
CCAGTCCAGG AGTGA                                                         435
```

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 9:

```
TGTGGATCCA CCATGGGACT GAGTAACATT                                          30
```

(2) INFORMATION FOR SEQ ID NO: 10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 10:

```
TTTGGATCCT TAAAAACATG TATCACTTTT GTCGC                                    35
```

(2) INFORMATION FOR SEQ ID NO: 11:

(i) SEQUENCE CHARACTERISTICS:
        (A) LENGTH: 972 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 11:

```
ATGGGACTGA GTAACATTCT CTTTGTGATG GCCTTCCTGC TCTCTGGTGC TGCTCCTCTG          60

AAGATTCAAG CTTATTTCAA TGAGACTGCA GACCTGCCAT GCCAATTTGC AAACTCTCAA         120

AACCAAAGCC TGAGTGAGCT AGTAGTATTT TGGCAGGACC AGGAAAACTT GGTTCTGAAT         180

GAGGTATACT TAGGCAAAGA GAAATTTGAC AGTGTTCATT CCAAGTATAT GGGCCGCACA         240

AGTTTTGATT CGGACAGTTG GACCCTGAGA CTTCACAATC TTCAGATCAA GGACAAGGGC         300

TTGTATCAAT GTATCATCCA TCACAAAAAG CCCACAGGAA TGATTCGCAT CCACCAGATG         360

AATTCTGAAC TGTCAGTGCT TGCTAACTTC AGTCAACCTG AAATAGTACC AATTTCTAAT         420

ATAACAGAAA ATGTGTACAT AAATTTGACC TGCTCATCTA TACACGGTTA CCCAGAACCT         480

AAGAAGATGA GTGTTTTGCT AAGAACCAAG AATTCAACTA TCGAGTATGA TGGTATTATG         540

CAGAAATCTC AAGATAATGT CACAGAACTG TACGACGTTT CCATCAGCTT GTCTGTTTCA         600

TTCCCTGATG TTACGAGCAA TATGACCATC TTCTGTATTC TGGAAACTGA CAAGACGCGG         660

CTTTTATCTT CACCTTTCTC TATAGAGCTT GAGGACCCTC AGCCTCCCCC AGACCACATT         720

CCTTGGATTA CAGCTGTACT TCCAACAGTT ATTATATGTG TGATGGTTTT CTGTCTAATT         780

CTATGGAAAT GGAAGAAGAA GAAGCGGCCT CGCAACTCTT ATAAATGTGG AACCAACACA         840

ATGGAGAGGG AAGAGAGTGA ACAGACCAAG AAAAGAGAAA AAATCCATAT ACCTGAAAGA         900
```

```
TCTGATGAAG CCCAGCGTGT TTTTAAAAGT TCGAAGACAT CTTCATGCGA CAAAAGTGAT    960

ACATGTTTTT AA                                                        972
```

(2) INFORMATION FOR SEQ ID NO: 12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 12:

```
AAAAGCTTGG ATCCACCATG AGTAAAGGA                                       29
```

(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 13:

```
AATCTAGATT ACTATTTGTA TAGTTCATCC                                      30
```

(2) INFORMATION FOR SEQ ID NO: 14:

(i) SEQUENCE CHARACTERISTICS:
        (A) LENGTH: 1451 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

```
AAGCTTTGGA GCTAAGCCAG CAATGGTAGA GGGAAGATTC TGCACGTCCC TTCCAGGCGG     60

CCTCCCCGTC ACCACCCCCC CCAACCCGCC CCGACCGGAG CTGAGAGTAA TTCATACAAA    120

AGGACTCGCC CCTGCCTTGG GGAATCCCAG GGACCGTCGT TAAACTCCCA CTAACGTAGA    180

ACCCAGAGAT CGCTGCGTTC CCGCCCCCTC ACCCGCCCGC TCTCGTCATC ACTGAGGTGG    240

AGAAGAGCCA TGCGTGAGGC TCCGGTGCCC GTCAGTGGGC AGAGCGCACA TCGCCCACAG    300

TCCCCGAGAA GTTGGGGGGA GGGGTCGGCA ATTGAACCGG TGCCTAGAGA AGGTGGCGCG    360

GGGTAAACTG GGAAAGTGAT GTCGTGTACT GGCTCCGCCT TTTTCCCGAG GGTGGGGGAG    420

AACCCGTATA TAAGTGCAGT AGTCGCCGTG AACGTTCTTT TTCGCAACGG GTTTGCCGCC    480

AGAACACAGG TAAGTGCCGT GTGTGGTTCC CGCGGGCCTG GCCTCTTTAC GGGTTATGGC    540

CCTTGCGTGC CTTGAATTAC TTCCACGCCC CTGGCTGCAG TACGTGATTC TTGATCCCGA    600

GCTTCGGGTT GGAAGTGGGT GGGAGAGTTC GAGGCCTTGC GCTTAAGGAG CCCCTTCGCC    660

TCGTGCTTGA GTTGAGGCCT GGCCTGGGCG CTGGGGCCCC CGCGTGCGAA TCTGGTGGCA    720

CCTTCGCGCC TGTCTCGCTG CTTTCGATAA GTCTCTAGCC ATTTAAAATT TTTGATGACC    780

TGCTGCGACG CTTTTTTTCT GGCAAGATAG TCTTGTAAAT GCGGGCCAAG ATCTGCACAC    840

TGGTATTTCG GTTTTTGGGG CCGCGGGCGG CGACGGGCC CGTGCGTCCC AGCGCACATG    900
```

```
TTCGGCGAGG CGGGGCCTGC GAGCGCGGCC ACCGAGAATC GGACGGGGGT AGTCTCAAGC      960

TGGCCGGCCT GCTCTGGTGC CTGGCCTCGC GCCGCCGTGT ATCGCCCCGC CCTGGGCGGC     1020

AAGGCTGGCC CGGTCGGCAC CAGTTGCGTG AGCGGAAAGA TGGCCGCTTC CCGGCCCTGC     1080

TGCAGGGAGC TCAAAATGGA GGACGCGGCG CTCGGGAGAG CGGGCGGGTG AGTCACCCAC     1140

ACAAAGGAAA AGGGCCTTTC CGTCCTCAGC CGTCGCTTCA TGTGACTCCA CGGAGTACCG     1200

GGCGCCGTCC AGGCACCTCG ATTAGTTCTC GAGCTTTTGG AGTACGTCGT CTTTAGGTTG     1260

GGGGGAGGGG TTTTATGCGA TGGAGTTTCC CCACACTGAG TGGGTGGAGA CTGAAGTTAG     1320

GCCAGCTTGG CACTTGATGT AATTCTCCTT GGAATTTGCC CTTTTTGAGT TTGGATCTTG     1380

GTTCATTCTC AAGCCTCAGA CAGTGGTTCA AGTTTTTTT CTTCCATTTC AGGTGTCGTG     1440

AAAACTCTAG A                                                         1451

(2) INFORMATION FOR SEQ ID NO: 15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 15:

AAGCTTTGGA GCTAAGCCAG CAAT                                             24

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 16:

TCTAGAGTTT TCACGACACC TGA                                              23

(2) INFORMATION FOR SEQ ID NO: 17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 17:

TCTAGAGCGG CCGCGGAGGC CGAATTCG                                         28

(2) INFORMATION FOR SEQ ID NO: 18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"
```

(xi) SEQUENCE DESCRIPTION: SEQ ID NO: 18:

GATCCGAATT CGGCCTCCGC GGCCGCTCTA GATGCA                              36

(2) INFORMATION FOR SEQ ID NO: 19:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 19:

GAAGATCTGC GGCCGCCACC ATGTGGCCCC CTGGGTCAGC                          40

(2) INFORMATION FOR SEQ ID NO: 20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 20:

CCTCTCGAGT TAGGAAGCAT TCAGATAGC                                     29

(2) INFORMATION FOR SEQ ID NO: 21:

(i) SEQUENCE CHARACTERISTICS:
        (A) LENGTH: 762 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 21:

ATGTGGCCCC CTGGGTCAGC CTCCCAGCCA CCGCCCTCAC CTGCCGCGGC CACAGGTCTG    60

CATCCAGCGG CTCGCCCTGT GTCCCTGCAG TGCCGGCTCA GCATGTGTCC AGCGCGCAGC   120

CTCCTCCTTG TCGCTACCCT GGTCCTCCTG GACCACCTCA GTTTGGCCAG AAACCTCCCC   180

GTGGCCACTC CAGACCCAGG AATGTTCCCA TGCCTTCACC ACTCCCAAAA CCTGCTGAGG   240

GCCGTCAGCA ACATGCTCCA GAAGGCCAGA CAAACTCTAG AATTTTACCC TTGCACTTCT   300

GAAGAGATTG ATCATGAAGA TATCACAAAA GATAAAACCA GCACAGTGGA GGCCTGTTTA   360

CCATTGGAAT TAACCAAGAA TGAGAGTTGC CTAAATTCCA GAGAGACCTC TTTCATAACT   420

AATGGGAGTT GCCTGGCCTC CAGAAAGACC TCTTTTATGA TGGCCCTGTG CCTTAGTAGT   480

ATTTATGAAG ACTTGAAGAT GTACCAGGTG GAGTTCAAGA CCATGAATGC AAAGCTTCTG   540

ATGGATCCTA AGAGGCAGAT CTTTCTAGAT CAAAACATGC TGGCAGTTAT TGATGAGCTG   600

ATGCAGGCCC TGAATTTCAA CAGTGAGACT GTGCCACAAA AATCCTCCCT TGAAGAACCG   660

GATTTTTATA AAACTAAAAT CAAGCTCTGC ATACTTCTTC ATGCTTTCAG AATTCGGGCA   720

GTGACTATTG ATAGAGTGAT GAGCTATCTG AATGCTTCCT AA                     762

(2) INFORMATION FOR SEQ ID NO: 22:

```
    (i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 22:

AAAGAGCTCC ACCATGTGTC ACCAGCAGTT GGTC                                 34

(2) INFORMATION FOR SEQ ID NO: 23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 23:

AAGGATCCTA ACTGCAGGGC ACAGATGC                                        28

(2) INFORMATION FOR SEQ ID NO: 24:

(i) SEQUENCE CHARACTERISTICS:
        (A) LENGTH: 987 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 24:

ATGTGTCACC AGCAGTTGGT CATCTCTTGG TTTTCCCTGG TTTTTCTGGC ATCTCCCCTC     60

GTGGCCATAT GGGAACTGAA GAAAGATGTT TATGTCGTAG AATTGGATTG GTATCCGGAT    120

GCCCCTGGAG AAATGGTGGT CCTCACCTGT GACACCCCTG AAGAAGATGG TATCACCTGG    180

ACCTTGGACC AGAGCAGTGA GGTCTTAGGC TCTGGCAAAA CCCTGACCAT CCAAGTCAAA    240

GAGTTTGGAG ATGCTGGCCA GTACACCTGT CACAAAGGAG GCGAGGTTCT AAGCCATTCG    300

CTCCTGCTGC TTCACAAAAA GGAAGATGGA ATTTGGTCCA CTGATATTTT AAAGGACCAG    360

AAAGAACCCA AAATAAGAC CTTTCTAAGA TGCGAGGCCA GAATTATTC TGGACGTTTC      420

ACCTGCTGGT GGCTGACGAC AATCAGTACT GATTTGACAT TCAGTGTCAA AAGCAGCAGA    480

GGCTCTTCTG ACCCCCAAGG GGTGACGTGC GGAGCTGCTA CACTCTCTGC AGAGAGAGTC    540

AGAGGGACA ACAAGGAGTA TGAGTACTCA GTGGAGTGCC AGGAGGACAG TGCCTGCCCA     600

GCTGCTGAGG AGAGTCTGCC CATTGAGGTC ATGGTGGATG CCGTTCACAA GCTCAAGTAT    660

GAAAACTACA CCAGCAGCTT CTTCATCAGG GACATCATCA AACCTGACCC ACCCAACAAC    720

TTGCAGCTGA AGCCATTAAA GAATTCTCGG CAGGTGGAGG TCAGCTGGGA GTACCCTGAC    780

ACCTGGAGTA CTCCACATTC CTACTTCTCC CTGACATTCT GCGTTCAGGT CCAGGGCAAG    840

AGCAAGAGAG AAAAGAAAGA TAGAGTCTTC ACCGACAAGA CCTCAGCCAC GGTCATCTGC    900

CGCAAAAATG CCAGCATTAG CGTGCGGGCC CAGGACCGCT ACTATAGCTC ATCTTGGAGC    960

GAATGGGCAT CTGTGCCCTG CAGTTAG                                       987
```

(2) INFORMATION FOR SEQ ID NO: 25:

(i) SEQUENCE CHARACTERISTICS:
        (A) LENGTH: 2097 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 25:

```
ATGAGGCTCG CCGTGGGAGC CCTGCTGGTC TGCGCCGTCC TGGGGCTGTG TCTGGCTGTC      60
CCTGATAAAA CTGTGAGATG GTGTGCAGTG TCGGAGCATG AGGCCACTAA GTGCCAGAGT     120
TTCCGCGACC ATATGAAAAG CGTCATTCCA TCCGATGGTC CCAGTGTTGC TTGTGTGAAG     180
AAAGCCTCCT ACCTTGATTG CATCAGGGCC ATTGCGGCAA ACGAAGCGGA TGCTGTGACA     240
CTGGATGCAG GTTTGGTGTA TGATGCTTAC TTGGCTCCCA ATAACCTGAA GCCTGTGGTG     300
GCAGAGTTCT ATGGGTCAAA AGAGGATCCA CAGACTTTCT ATTATGCTGT TGCTGTGGTG     360
AAGAAGGATA GTGGCTTCCA GATGAACCAG CTTCGAGGCA AGAAGTCCTG CCACACGGGT     420
CTAGGCAGGT CCGCTGGGTG GAACATCCCC ATAGGCTTAC TTTACTGTGA CTTACCTGAG     480
CCACGTAAAC CTCTTGAGAA AGCAGTGGCC AATTTCTTCT CGGGCAGCTG TGCCCCTTGT     540
GCGGATGGGA CGGACTTCCC CCAGCTGTGT CAACTGTGTC CAGGGTGTGG CTGCTCCACC     600
CTTAACCAAT ACTTCGGCTA CTCGGGAGCC TTCAAGTGTC TGAAGGATGG TGCTGGGGAT     660
GTGGCCTTTG TCAAGCACTC GACTATATTT GAGAACTTGG CAAACAAGGC TGACAGGGAC     720
CAGTATGAGC TGCTTTGCCT AGACAACACC CGGAAGCCGG TAGATGAATA CAAGGACTGC     780
CACTTGGCCC AGGTCCCTTC TCATACCGTC GTGGCCCGAA GTATGGGCGG CAAGGAGGAC     840
TTGATCTGGG AGCTTCTCAA CCAGGCCCAG GAACATTTTG GCAAAGACAA ATCAAAAGAA     900
TTCCAACTAT TCAGCTCTCC TCATGGGAAG GACCTGCTGT TTAAGGACTC TGCCCACGGG     960
TTTTTAAAAG TCCCCCCAAG GATGGATGCC AAGATGTACC TGGGCTATGA GTATGTCACT    1020
GCCATCCGGA ATCTACGGGA AGGCACATGC CCAGAAGCCC AACAGATGA ATGCAAGCCT     1080
GTGAAGTGGT GTGCGCTGAG CCACCACGAG AGGCTCAAGT GTGATGAGTG GAGTGTTAAC    1140
AGTGTAGGGA AAATAGAGTG TGTATCAGCA GAGACCACCG AAGACTGCAT CGCCAAGATC    1200
ATGAATGGAG AAGCTGATGC CATGAGCTTG GATGGAGGGT TTGTCTACAT AGCGGGCAAG    1260
TGTGGTCTGG TGCCTGTCTT GGCAGAAAAC TACAATAAGA GCGATAATTG TGAGGATACA    1320
CCAGAGGCAG GGTATTTTGC TGTAGCAGTG GTGAAGAAAT CAGCTTCTGA CCTCACCTGG    1380
GACAATCTGA AAGGCAAGAA GTCCTGCCAT ACGGCAGTTG GCAGAACCGC TGGCTGGAAC    1440
ATCCCCATGG GCCTGCTCTA CAATAAGATC AACCACTGCA GATTTGATGA ATTTTTCAGT    1500
GAAGGTTGTG CCCCTGGGTC TAAGAAAGAC TCCAGTCTCT GTAAGCTGTG TATGGGCTCA    1560
GGCCTAAACC TGTGTGAACC CAACAACAAA GAGGGATACT ACGGCTACAC AGGCGCTTTC    1620
AGGTGTCTGG TTGAGAAGGG AGATGTGGCC TTTGTGAAAC ACCAGACTGT CCCACAGAAC    1680
ACTGGGGGAA AAAACCCTGA TCCATGGGCT AAGAATCTGA ATGAAAAGA CTATGAGTTG     1740
CTGTGCCTTG ATGGTACCAG GAAACCTGTG GAGGAGTATG CGAACTGCCA CCTGGCCAGA    1800
GCCCCGAATC ACGCTGTGGT CACACGGAAA GATAAGGAAG CTTGCGTCCA AAGATATTA     1860
CGTCAACAGC AGCACCTATT TGGAAGCAAC GTAACTGACT GCTCGGGCAA CTTTTGTTTG    1920
TTCCGGTCGG AAACCAAGGA CCTTCTGTTC AGAGATGACA CAGTATGTTT GGCCAAACTT    1980
```

```
CATGACAGAA ACACATATGA AAAATACTTA GGAGAAGAAT ATGTCAAGGC TGTTGGTAAC    2040

CTGAGAAAAT GCTCCACCTC ATCACTCCTG GAAGCCTGCA CTTTCCGTAG ACCTTAA      2097
```

(2) INFORMATION FOR SEQ ID NO: 26:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 26:

```
AGGCGTTACT CGACAGAGGA GAGCAAGAAA TGGAGCCAGT AGATCCTAGA CTAGAGCCCT    60

GGAAGCATCC AGGAAGTCAG CCTAAAACTG CTTGTACCAA TTGCTATTGT AAAAAGTGTT   120

GCTTTCATTG CCAAGTTTGT                                              140
```

(2) INFORMATION FOR SEQ ID NO: 27:

(i) SEQUENCE CHARACTERISTICS:
        (A) LENGTH: 70 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 27:

```
TATAAGATGG GTGGCAAGTG GTCAAAAAGT AGTGTGATTG GATGGCCTGC TGTAAGGGAA    60

AGAATGAGAC                                                          70
```

(2) INFORMATION FOR SEQ ID NO: 28:

(i) SEQUENCE CHARACTERISTICS:
        (A) LENGTH: 70 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 28:

```
CTCAGGTACC TTTAAGACCA ATGACTTACA AGGCAGCTGT AGATCTTAGC CACTTTTTAA    60

AAGAAAAGGG                                                          70
```

(2) INFORMATION FOR SEQ ID NO: 29:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 29:

```
AGCTTGGTCG CCCGGTGGAT CAAGACCGGT AGCCGTCATA AAGGTGATTT CGTCG         55
```

(2) INFORMATION FOR SEQ ID NO: 30:

(i) SEQUENCE CHARACTERISTICS:
    (A) LENGTH: 55 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA"

(xi) SEQUENCE DESCRIPTION: SEQ ID NO: 30:

GATCCGACGA AATCACCTTT ATGACGGCTA CCGGTCTTGA TCCACCGGGC GACCA         55

(2) INFORMATION FOR SEQ ID NO: 31:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 31:

CGGGATCCAC CATGGGTGCG AGAGCGTC                                       28

(2) INFORMATION FOR SEQ ID NO: 32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 32:

ATCCTATTTG TTCCTGAAGG                                                20

(2) INFORMATION FOR SEQ ID NO: 33:

(i) SEQUENCE CHARACTERISTICS:
        (A) LENGTH: 12494 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "DNA"

(xi) SEQUENCE DESCRIPTION: SEQ ID NO: 33:

CACGTGGCCC GAGAGCTGCA TCCGGAGTAT CTAGATGGAG TTCCGCGTTA CATAACTTAC    60

GGTAAATGGC CCGCCTGGCT GACCGCCCAA CGACCCCCGC CCATTGACGT CAATAATGAC   120

TGATGTTCCC ATAGTAACGC CAATAGGGAC TTTCCATTGA CGCTAATGGG AGTTTGTTTT   180

GGCACCAAAA TCAACGGGAC TTTCCAAAAT GTCGTAATAA CCCCGCCCCG TTGACGCAAA   240

TGGGCGGTAG GCGTGTACTC TAGAAGGTCT ATATAAGCAG AGCTCGTTTA GTGAACCGTT   300

TATACTACTT ATCTGGTCTC TCTGGTTAGA CCAGATCTGA GCCTGGGAGC TCTCTGGCTA   360

ACTAGGGAAC CCACTGCTTA AGCCTCAATA AAGCTTTGGT CGCCCGGTGG ATCAAGACCG   420

GTAGCCGTCA TAAAGGTGAT TCGTCGGAT CCACCGAGAG ATGGGTGCGA GAGCGTCGGT   480

ATTAAGCGGG GGAGAATTAG ATAAATGGGA AAAAATTCGG TTAAGGCCAG GGGGAAAGAA   540

ACAATATAAA CTAAAACATA TAGTATGGGC AAGCAGGGAG CTAGAACGAT TCGCAGTTAA   600

-continued

```
TCCTGGCCTT TTAGAGACAT CAGAAGGCTG TAGACAAATA CTGGGACAGC TACAACCATC    660

CCTTCAGACA GGATCAGAAG AACTTAGATC ATTATATAAT ACAATAGCAG TCCTCTATTG    720

TGTGCATCAA AGGATAGATG TAAAAGACAC CAAGGAAGCC TTAGATAAGA TAGAGGAAGA    780

GCAAAACAAA AGTAAGAAAA AGGCACAGCA AGCAGCAGCT GACACAGGAA ACAACAGCCA    840

GGTCAGCCAA AATTACCCTA TAGTGCAGAA CCTCCAGGGG CAAATGGTAC ATCAGGCCAT    900

ATCACCTAGA ACTTTAAATG CATGGGTAAA AGTAGTAGAA GAGAAGGCTT TCAGCCCAGA    960

AGTAATACCC ATGTTTTCAG CATTATCAGA AGGAGCCACC CCACAAGATT TAAATACCAT   1020

GCTAAACACA GTGGGGGGAC ATCAAGCAGC CATGCAAATG TTAAAAGAGA CCATCAATGA   1080

GGAAGCTGCA GAATGGGATA GATTGCATCC AGTGCATGCA GGGCCTATTG CACCAGGCCA   1140

GATGAGAGAA CCAAGGGGAA GTGACATAGC AGGAACTACT AGTACCCTTC AGGAACAAAT   1200

AGGATGGATG ACACATAATC CACCTATCCC AGTAGGAGAA ATCTATAAAA GATGGATAAT   1260

CCTGGGATTA AATAAAATAG TAAGAATGTA TAGCCCTACC AGCATTCTGG ACATAAGACA   1320

AGGACCAAAG GAACCCTTTA GAGACTATGT AGACCGATTC TATAAAACTC TAAGAGCCGA   1380

GCAAGCTTCA CAAGAGGTAA AAAATTGGAT GACAGAAACC TTGTTGGTCC AAAATGCGAA   1440

CCCAGATTGT AAGACTATTT TAAAAGCATT GGGACCAGGA GCGACACTAG AAGAAATGAT   1500

GACAGCATGT CAGGGAGTGG GGGGACCCGG CCATAAAGCA AGAGTTTTGG CTGAAGCAAT   1560

GAGCCAAGTA ACAAATCCAG CTACCATAAT GATACAGAAA GGCAATTTTA GGAACCAAAG   1620

AAAGACTGTT AAGTGTTTCA ATTGTGGCAA AGAAGGGCAC ATAGCCAAAA ATTGCAGGGC   1680

CCCTAGGAAA AAGGGCTGTT GGAAATGTGG AAAGGAAGGA CACCAAATGA AAGATTGTAC   1740

TGAGAGACAG GCTAATTTTT TAGGGAAGAT CTGGCCTTCC CACAAGGGAA GGCCAGGGAA   1800

TTTTCTTCAG AGCAGACCAG AGCCAACAGC CCCACCAGAA GAGAGCTTCA GGTTTGGGGA   1860

AGAGACAACA ACTCCCTCTC AGAAGCAGGA GCCGATAGAC AAGGAACTGT ATCCTTTAGC   1920

TTCCCTCAGA TCACTCTTTG GCAGCGACCC CTCGTCACAA TAAAGATAGG GGGCAATTA   1980

AAGGAAGCTC TATTAGATAC AGGAGCAGAT GATACAGTAT TAGAAGAAAT GAATTTGCCA   2040

GGAAGATGGA AACCAAAAAT GATAGGGGGA ATTGGAGGTT TTATCAAAGT AGGACAGTAT   2100

GATCAGATAC TCATAGAAAT CTGCGGACAT AAAGCTATAG GTACAGTATT AGTAGGACCT   2160

ACACCTGTCA ACATAATTGG AAGAAATCTG TTGACTCAGA TTGGCTGCAC TTTAAATTTT   2220

CCCATTAGTC CTATTGAGAC TGTACCAGTA AAATTAAAGC CAGGAATGGA TGGCCCAAAA   2280

GTTAAACAAT GGCCATTGAC AGAAGAAAAA ATAAAAGCAT TAGTAGAAAT TTGTACAGAA   2340

ATGGAAAAGG AAGGAAAAAT TTCAAAAATT GGGCCTGAAA ATCCATACAA TACTCCAGTA   2400

TTTGCCATAA AGAAAAAGA CAGTACTAAA TGGAGAAAAT TAGTAGATTT CAGAGAACTT   2460

AATAAGAGAA CTCAAGATTT CTGGGAAGTT CAATTAGGAA TACCACATCC TGCAGGGTTA   2520

AAACAGAAAA AATCAGTAAC AGTACTGGAT GTGGGCGATG CATATTTTTC AGTTCCCTTA   2580

GATAAAGACT TCAGGAAGTA TACTGCATTT ACCATACCTA GTATAAACAA TGAGACACCA   2640

GGGATTAGAT ATCAGTACAA TGTGCTTCCA CAGGGATGGA AAGGATCACC AGCAATATTC   2700

CAGTGTAGCA TGACAAAAAT CTTAGAGCCT TTTAGAAAAC AAAATCCAGA CATAGTCATC   2760

TATCAATACA TGGATGATTT GTATGTAGGA TCTGACTTAG AAATAGGGCA GCATAGAACA   2820

AAAATAGAGG AACTGAGACA ACATCTGTTG AGGTGGGGAT TTACCACACC AGACAAAAAA   2880

CATCAGAAAG AACCTCCATT CCTTTGGATG GGTTATGAAC TCCATCCTGA TAAATGGACA   2940

GTACAGCCTA TAGTGCTGCC AGAAAAGGAC AGCTGGACTG TCAATGACAT ACAGAAATTA   3000
```

```
GTGGGAAAAT TGAATTGGGC AAGTCAGATT TATGCAGGGA TTAAAGTAAG GCAATTATGT    3060

AAACTTCTTA GGGGAACCAA AGCACTAACA GAAGTAGTAC CACTAACAGA AGAAGCAGAG    3120

CTAGAACTGG CAGAAAACAG GGAGATTCTA AAAGAACCGG TACATGGAGT GTATTATGAC    3180

CCATCAAAAG ACTTAATAGC AGAAATACAG AAGCAGGGGC AAGGCCAATG GACATATCAA    3240

ATTTATCAAG AGCCATTTAA AAATCTGAAA ACAGGAAAAT ATGCAAGAAT GAAGGGTGCC    3300

CACACTAATG ATGTGAAACA ATTAACAGAG GCAGTACAAA AAATAGCCAC AGAAAGCATA    3360

GTAATATGGG GAAAGACTCC TAAATTTAAA TTACCCATAC AAAAGGAAAC ATGGGAAGCA    3420

TGGTGGACAG AGTATTGGCA AGCCACCTGG ATTCCTGAGT GGGAGTTTGT CAATACCCCT    3480

CCCTTAGTGA AGTTATGGTA CCAGTTAGAG AAAGAACCCA TAATAGGAGC AGAAACTTTC    3540

TATGTAGATG GGGCAGCCAA TAGGGAAACT AAATTAGGAA AGCAGGATA TGTAACTGAC    3600

AGAGGAAGAC AAAAAGTTGT CCCCCTAACG GACACAACAA ATCAGAAGAC TGAGTTACAA    3660

GCAATTCATC TAGCTTTGCA GGATTCGGGA TTAGAAGTAA ACATAGTGAC AGACTCACAA    3720

TATGCATTGG GAATCATTCA AGCACAACCA GATAAGAGTG AATCAGAGTT AGTCAGTCAA    3780

ATAATAGAGC AGTTAATAAA AAAGGAAAAA GTCTACCTGG CATGGGTACC AGCACACAAA    3840

GGAATTGGAG GAAATGAACA AGTAGATGGG TTGGTCAGTG CTGGAATCAG GAAAGTACTA    3900

TTTTTAGATG GAATAGATAA GGCCCAAGAA GAACATGAGA AATATCACAG TAATTGGAGA    3960

GCAATGGCTA GTGATTTTAA CCTACCACCT GTAGTAGCAA AAGAAATAGT AGCCAGCTGT    4020

GATAAATGTC AGCTAAAAGG GGAAGCCATG CATGGACAAG TAGACTGTAG CCCAGGAATA    4080

TGGCAGCTAG ATTGTACACA TTTAGAAGGA AAAGTTATCT TGGTAGCAGT TCATGTAGCC    4140

AGTGGATATA TAGAAGCAGA AGTAATTCCA GCAGAGACAG GGCAAGAAAC AGCATACTTC    4200

CTCTTAAAAT TAGCAGGAAG ATGGCCAGTA AAAACAGTAC ATACAGACAA TGGCAGCAAT    4260

TTCACCAGTA CTACAGTTAA GGCCGCCTGT TGGTGGGCGG GGATCAAGCA GGAATTTGGC    4320

ATTCCCTACA ATCCCCAAAG TCAAGGAGTA ATAGAATCTA TGAATAAAGA ATTAAAGAAA    4380

ATTATAGGAC AGGTAAGAGA TCAGGCTGAA CATCTTAAGA CAGCAGTACA AATGGCAGTA    4440

TTCATCCACA ATTTTAAAAG AAAAGGGGGG ATTGGGGGGT ACAGTGCAGG GGAAAGAATA    4500

GTAGACATAA TAGCAACAGA CATACAAACT AAAGAATTAC AAAAACAAAT TACAAAAATT    4560

CAAAATTTTC GGGTTTATTA CAGGGACAGC AGAGATCCAG TTTGGAAAGG ACCAGCAAAG    4620

CTCCTCTGGA AAGGTGAAGG GGCAGTAGTA ATACAAGATA ATAGTGACAT AAAAGTAGTG    4680

CCAAGAAGAA AAGCAAAGAT CATCAGGGAT TATGGAAAAC AGATGGCAGG TGATGATTGT    4740

GTGGCAAGTA GACAGGATGA GGATTAACAC ATGGAAAAGA TTAGTAAAAC ACCATATGTA    4800

TATTTCAAGG AAAGCTAAGG ACTGGTTTTA TAGACATCAC TATGAAAGTA CTAATCCAAA    4860

AATAAGTTCA GAAGTACACA TCCCACTAGG GGATGCTAAA TTAGTAATAA CAACATATTG    4920

GGGTCTGCAT ACAGGAGAAA GAGACTGGCA TTTGGGTCAG GGAGTCTCCA TAGAATGGAG    4980

GAAAAGAGA TATAGCACAC AAGTAGACCC TGACCTAGCA GACCAACTAA TTCATCTGCA    5040

CTATTTTGAT TGTTTTTCAG AATCTGCTAT AAGAAATACC ATATTAGGAC GTATAGTTAG    5100

TCCTAGGTGT GAATATCAAG CAGGACATAA CAAGGTAGGA TCTCTACAGT ACTTGGCACT    5160

AGCAGCATTA ATAAAACCAA AACAGATAAA GCCACCTTTG CCTAGTGTTA GGAAACTGAC    5220

AGAGGACAGA TGGAACAAGC CCCAGAAGAC CAAGGGCCAC AGAGGGAGCC ATACAATGAA    5280

TGGACACTAG AGCTTTTAGA GGAACTTAAG AGTGAAGCTG TTAGACATTT TCCTAGGATA    5340
```

-continued

```
TGGCTCCATA ACTTAGGACA ACATATCTAT GAAACTTACG GGGATACTTG GGCAGGAGTG    5400

GAAGCCATAA TAAGAATTCT GCAACAACTG CTGTTTATCC ATTTCAGAAT TGGGTGTCGA    5460

CATAGCAGAA TAGGCGTTAC TCGACAGAGG AGAGCAAGAA ATGGAGCCAG TAGATCCTAG    5520

ACTAGAGCCC TGGAAGCATC CAGGAAGTCA GCCTAAAACT GCTTGTACCA ATTGCTATTG    5580

TAAAAAGTGT TGCTTTCATT GCCAAGTTTG TTTCATGACA AAAGCCTTAG GCATCTCCTA    5640

TGGCAGGAAG AAGCGGAGAC AGCGACGAAG AGCTCATCAG AACAGTCAGA CTCATCAAGC    5700

TTCTCTATCA AAGCAGTAAG TAGTACATGT AATGCAACCT ATAATAGTAG CAATAGTAGC    5760

ATTAGTAGTA GCAATAATAA TAGCAATAGT TGTGTGGTCC ATAGTAATCA TAGAATATAG    5820

GAAAATATTA AGACAAAGAA AAATAGACAG GTTAATTGAT AGACTAATAG AAAGAGCAGA    5880

AGACAGTGGC AATGAGAGTG AAGGAGAAGT ATCAGCACTT GTGGAGATGG GGGTGGAAAT    5940

GGGGCACCAT GCTCCTTGGG ATATTGATGA TCTGTAGTGC TACAGAAAAA TTGTGGGTCA    6000

CAGTCTATTA TGGGGTACCT GTGTGGAAGG AAGCAACCAC CACTCTATTT TGTGCATCAG    6060

ATGCTAAAGC ATATGATACA GAGGTACATA ATGTTTGGGC CACACATGCC TGTGTACCCA    6120

CAGACCCCAA CCCACAAGAA GTAGTATTGG TAAATGTGAC AGAAAATTTT AACATGTGGA    6180

AAAATGACAT GGTAGAACAG ATGCATGAGG ATATAATCAG TTTATGGGAT CAAAGCCTAA    6240

AGCCATGTGT AAAATTAACC CCACTCTGTG TTAGTTTAAA GTGCACTGAT TTGAAGAATG    6300

ATACTAATAC CAATAGTAGT AGCGGGAGAA TGATAATGGA GAAGGAGAG ATAAAAAACT     6360

GCTCTTTCAA TATCAGCACA AGCATAAGAG ATAAGGTGCA GAAAGAATAT GCATTCTTTT    6420

ATAAACTTGA TATAGTACCA ATAGATAATA CCAGCTATAG GTTGATAAGT TGTAACACCT    6480

CAGTCATTAC ACAGGCCTGT CCAAAGGTAT CCTTTGAGCC AATTCCCATA CATTATTGTG    6540

CCCCGGCTGG TTTTGCGATT CTAAAATGTA ATAATAAGAC GTTCAATGGA ACAGGACCAT    6600

GTACAAATGT CAGCACAGTA CAATGTACAC ATGGAATCAG GCCAGTAGTA TCAACTCAAC    6660

TGCTGTTAAA TGGCAGTCTA GCAGAAGAAG ATGTAGTAAT TAGATCTGCC AATTTCACAG    6720

ACAATGCTAA AACCATAATA GTACAGCTGA ACACATCTGT AGAAATTAAT TGTACAAGAC    6780

CCAACAACAA TACAAGAAAA AGTATCCGTA TCCAGAGGGG ACCAGGGAGA GCATTTGTTA    6840

CAATAGGAAA AATAGGAAAT ATGAGACAAG CACATTGTAA CATTAGTAGA GCAAAATGGA    6900

ATGCCACTTT AAAACAGATA GCTAGCAAAT TAAGAGAACA ATTTGGAAAT AATAAAACAA    6960

TAATCTTTAA GCAATCCTCA GGAGGGGACC CAGAAATTGT AACGCACAGT TTTAATTGTG    7020

GAGGGGAATT TTTCTACTGT AATTCAACAC AACTGTTTAA TAGTACTTGG TTTAATAGTA    7080

CTTGGAGTAC TGAAGGGTCA AATAACACTG AAGGAAGTGA CACAATCACA CTCCCATGCA    7140

GAATAAAACA ATTTATAAAC ATGTGGCAGG AAGTAGGAAA AGCAATGTAT GCCCCTCCCA    7200

TCAGTGGACA AATTAGATGT TCATCAAATA TTACTGGGCT GCTATTAACA AGAGATGGTG    7260

GTAATAACAA CAATGGGTCC GAGATCTTCA GACCTGGAGG AGGCGATATG AGGGACAATT    7320

GGAGAAGTGA ATTATATAAA TATAAAGTAG TAAAAATTGA ACCATTAGGA GTAGCACCCA    7380

CCAAGGCAAA GAGAAGAGTG GTGCAGAGAG AAAAAAGAGC AGTGGGAATA GGAGCTTTGT    7440

TCCTTGGGTT CTTGGGAGCA GCAGGAAGCA CTATGGGCGC ACGGTCAATG ACGCTGACGG    7500

TACAGGCCAG ACAATTATTG TCTGATATAG TGCAGCAGCA GAACAATTTG CTGAGGGCTA    7560

TTGAGGCGCA ACAGCATCTG TTGCAACTCA CAGTCTGGGG CATCAAACAG CTCCAGGCAA    7620

GAATCCTGGC TGTGGAAAGA TACCTAAAGG ATCAACAGCT CCTGGGGATT TGGGGTTGCT    7680

CTGGAAAACT CATTTGCACC ACTGCTGTGC CTTGGAATGC TAGTTGGAGT AATAAATCTC    7740
```

```
                                                          -continued

TGGAACAGAT TTGGAATAAC ATGACCTGGA TGGAGTGGGA CAGAGAAATT AACAATTACA     7800

CAAGCTTAAT ACACTCCTTA ATTGAAGAAT CGCAAAACCA GCAAGAAAAG AATGAACAAG     7860

AATTATTGGA ATTAGATAAA TGGGCAAGTT TGTGGAATTG GTTTAACATA ACAAATTGGC     7920

TGTGGTATAT AAAATTATTC ATAATGATAG TAGGAGGCTT GGTAGGTTTA AGAATAGTTT     7980

TTGCTGTACT TTCTATAGTG AATAGAGTTA GGCAGGGATA TTCACCATTA TCGTTTCAGA     8040

CCCACCTCCC AATCCCGAGG GGACCCGACA GGCCCGAAGG AATAGAAGAA GAAGGTGGAG     8100

AGAGAGACAG AGACAGATCC ATTCGATTAG TGAACGGATC CTTAGCACTT ATCTGGGACG     8160

ATCTGCGGAG CCTGTGCCTC TTCAGCTACC ACCGCTTGAG AGACTTACTC TTGATTGTAA     8220

CGAGGATTGT GGAACTTCTG GGACGCAGGG GGTGGGAAGC CCTCAAATAT TGGTGGAATC     8280

TCCTACAGTA TTGGAGTCAG GAACTAAAGA ATAGTGCTGT TAACTTGCTC AATGCCACAG     8340

CCATAGCAGT AGCTGAGGGG ACAGATAGGG TTATAGAAGT ATTACAAGCA GCTTATAGAG     8400

CTATTCGCCA CATACCTAGA AGAATAAGAC AGGGCTTGGA AAGGATTTTG CTATAAGCTT     8460

TATATATAGT GTTATAGTGC GCCAGATCTC TATAATCTCG CGCAACCTAT TTTCCCCTCG     8520

AACACTTTTT AAGCCGTAGA TAAACAGGCT GGGACACTTC ACATGAGCGA AAAATACATC     8580

GTCACCTGGG ACATGTTGCA GATCCATGCA CGTAAACTCG CAAGCCGACT GATGCCTTCT     8640

GAACAATGGA AAGGCATTAT TGCCGTAAGC CGTGGCGGTC TGGTACCGGG TGCGTTACTG     8700

GCGCGTGAAC TGGGTATTCG TCATGTCGAT ACCGTTTGTA TTTCCAGCTA CGATCACGAC     8760

AACCAGCGCG AGCTTAAAGT GCTGAAACGC GCAGAAGGCG ATGGCGAAGG CTTCATCGTT     8820

ATTGATGACC TGGTGGATAC CGGTGGTACT GCGGTTGCGA TTCGTGAAAT GTATCCAAAA     8880

GCGCACTTTG TCACCATCTT CGCAAAACCG GCTGGTCGTC CGCTGGTTGA TGACTATGTT     8940

GTTGATATCC CGCAAGATAC CTGGATTGAA CAGCCGTGGG ATATGGGCGT CGTATTCGTC     9000

CCGCCAATCT CCGGTCGCTA ACTCGAGACT CGAGGCCGGC AAGGCCGGAT CCAGACATGA     9060

TAAGATACAT TGATGAGTTT GGACAAACCA CAACTAGAAT GCAGTGAAAA AAATGCTTTA     9120

TTTGTGAAAT TTGTGATGCT ATTGCTTTAT TTGTAACCAT TATAAGCTGC AATAAACAAG     9180

TTAACAACAA CAATTGCATT CATTTTATGT TTCAGGTTCA GGGGGAGGTG GGGAGGTTTT     9240

TTAAAGCAAG TAAAACCTCT ACAAATGTGG TATGGCTGAT TATGATCCGG CTGCCTCGCG     9300

CGTTTCGGTG ATGACGGTGA AAACCTCTGA CACATGCAGC TCCCGGAGAC GGTCACAGCT     9360

TGTCTGTAAG CGGATGCCGG GAGCAGACAA GCCCGTCAGG GCGCGTCAGC GGGTGTTGGC     9420

GGGTGTCGGG GCGCAGCCAT GACCGGTCGA CTGCAGTCTC TGCAGGAATT CGATATCAAG     9480

CTTATCGATA CCGTCGACCT CGAGGGGGGG CCCGGTACCC AATTCGCCCT ATAGTGAGTC     9540

GTATTACAAT TCACTGGCCG TCGTTTTACA ACGTCGTGAC TGGGAAAACC CTGGCGTTAC     9600

CCAACTTAAT CGCCTTGCAG CACATCCCCC TTTCGCCAGC TGGCGTAATA GCGAAGAGGC     9660

CCGCACCGAT CGCCCTTCCC AACAGTTGCG CAGCCTGAAT GGCGAATGGA AATTGTAAGC     9720

GTTAATATTT TGTTAAAATT CGCGTTAAAT TTTTGTTAAA TCAGCTCATT TTTTAACCAA     9780

TAGGCCGAAA TCGGCAAAAT CCCTTATAAA TCAAAAGAAT AGACCGAGAT AGGGTTGAGT     9840

GTTGTTCCAG TTTGGAACAA GAGTCCACTA TTAAAGAACG TGGACTCCAA CGTCAAAGGG     9900

CGAAAAACCG TCTATCAGGG CGATGGCCCA CTACGTGAAC CATCACCCTA ATCAAGTTTT     9960

TTGGGGTCGA GGTGCCGTAA AGCACTAAAT CGGAACCCTA AAGGGAGCCC CCGATTTAGA    10020

GCTTGACGGG GAAAGCCGGC GAACGTGGCG AGAAAGGAAG GGAAGAAAGC GAAAGGAGCG    10080
```

-continued

```
GGCGCTAGGG CGCTGGCAAG TGTAGCGGTC ACGCTGCGCG TAACCACCAC ACCCGCCGCG    10140

CTTAATGCGC CGCTACAGGG CGCGTCAGGT GGCACTTTTC GGGGAAATGT GCGCGGAACC    10200

CCTATTTGTT TATTTTTCTA AATACATTCA AATATGTATC CGCTCATGAG ACAATAACCC    10260

TGATAAATGC TTCAATAATA TTGAAAAAGG AAGAGTATGA GTATTCAACA TTTCCGTGTC    10320

GCCCTTATTC CCTTTTTTGC GGCATTTTGC CTTCCTGTTT TTGCTCACCC AGAAACGCTG    10380

GTGAAAGTAA AAGATGCTGA AGATCAGTTG GGTGCACGAG TGGGTTACAT CGAACTGGAT    10440

CTCAACAGCG GTAAGATCCT TGAGAGTTTT CGCCCCGAAG AACGTTTTCC AATGATGAGC    10500

ACTTTTAAAG TTCTGCTATG TGGCGCGGTA TTATCCCGTA TTGACGCCGG GCAAGAGCAA    10560

CTCGGTCGCC GCATACACTA TTCTCAGAAT GACTTGGTTG AGTACTCACC AGTCACAGAA    10620

AAGCATCTTA CGGATGGCAT GACAGTAAGA GAATTATGCA GTGCTGCCAT AACCATGAGT    10680

GATAACACTG CGGCCAACTT ACTTCTGACA ACGATCGGAG GACCGAAGGA GCTAACCGCT    10740

TTTTTGCACA ACATGGGGGA TCATGTAACT CGCCTTGATC GTTGGGAACC GGAGCTGAAT    10800

GAAGCCATAC CAAACGACGA GCGTGACACC ACGATGCCTG TAGCAATGGC AACAACGTTG    10860

CGCAAACTAT TAACTGGCGA ACTACTTACT CTAGCTTCCC GGCAACAATT AATAGACTGG    10920

ATGGAGGCGG ATAAAGTTGC AGGACCACTT CTGCGCTCGG CCCTTCCGGC TGGCTGGTTT    10980

ATTGCTGATA AATCTGGAGC CGGTGAGCGT GGGTCTCGCG GTATCATTGC AGCACTGGGG    11040

CCAGATGGTA AGCCCTCCCG TATCGTAGTT ATCTACACGA CGGGGAGTCA GGCAACTATG    11100

GATGAACGAA ATAGACAGAT CGCTGAGATA GGTGCCTCAC TGATTAAGCA TTGGTAACTG    11160

TCAGACCAAG TTTACTCATA TATACTTTAG ATTGATTTAA AACTTCATTT TTAATTTAAA    11220

AGGATCTAGG TGAAGATCCT TTTTGATAAT CTCATGACCA AAATCCCTTA ACGTGAGTTT    11280

TCGTTCCACT GAGCGTCAGA CCCCGTAGAA AAGATCAAAG GATCTTCTTG AGATCCTTTT    11340

TTTCTGCGCG TAATCTGCTG CTTGCAAACA AAAAAACCAC CGCTACCAGC GGTGGTTTGT    11400

TTGCCGGATC AAGAGCTACC AACTCTTTTT CCGAAGGTAA CTGGCTTCAG CAGAGCGCAG    11460

ATACCAAATA CTGTCCTTCT AGTGTAGCCG TAGTTAGGCC ACCACTTCAA GAACTCTGTA    11520

GCACCGCCTA CATACCTCGC TCTGCTAATC CTGTTACCAG TGGCTGCTGC CAGTGGCGAT    11580

AAGTCGTGTC TTACCGGGTT GGACTCAAGA CGATAGTTAC CGGATAAGGC GCAGCGGTCG    11640

GGCTGAACGG GGGGTTCGTG CACACAGCCC AGCTTGGAGC GAACGACCTA CACCGAACTG    11700

AGATACCTAC AGCGTGAGCT ATGAGAAAGC GCCACGCTTC CCGAAGGGAG AAAGGCGGAC    11760

AGGTATCCGG TAAGCGGCAG GGTCGGAACA GGAGAGCGCA CGAGGGAGCT TCCAGGGGGA    11820

AACGCCTGGT ATCTTTATAG TCCTGTCGGG TTTCGCCACC TCTGACTTGA GCGTCGATTT    11880

TTGTGATGCT CGTCAGGGGG GCGGAGCCTA TGGAAAAACG CCAGCAACGC GGCCTTTTTA    11940

CGGTTCCTGG CCTTTTGCTG GCCTTTTGCT CACATGTTCT TTCCTGCGTT ATCCCCTGAT    12000

TCTGTGGATA ACCGTATTAC CGCCTTTGAG TGAGCTGATA CCGCTCGCCG CAGCCGAACG    12060

ACCGAGCGCA GCGAGTCAGT GAGCGAGGAA GCGGAAGAGC GCCCAATACG CAAACCGCCT    12120

CTCCCCGCGC GTTGGCCGAT TCATTAATGC AGCTGGCACG ACAGGTTTCC CGACTGGAAA    12180

GCGGGCAGTG AGCGCAACGC AATTAATGTG AGTTAGCTCA CTCATTAGGC ACCCCAGGCT    12240

TTACACTTTA TGCTTCCGGC TCGTATGTTG TGTGGAATTG TGAGCGGATA ACAATTTCAC    12300

ACAGGAAACA GCTATGACCA TGATTACGCC AAGCTCGAAA TTAACCCTCA CTAAAGGGAA    12360

CAAAAGCTGG AGCTCCACCG CGGTGGCGGC CGTCTCTAGA ACTAGTGGAT CCCCCGGGCT    12420
```

-continued

```
GCAGGAATTC GATAACACAC TGGCTTATCG AAATTAATAC GACTCACTAT AGGGAGACCG    12480

GCAGATCTGA TATC                                                     12494
```